(12) United States Patent
Plourde, Jr. et al.

(10) Patent No.: US 7,749,980 B2
(45) Date of Patent: Jul. 6, 2010

(54) NON-NUCLEOTIDE COMPOSITIONS AND METHOD FOR TREATING PAIN

(75) Inventors: Robert Plourde, Jr., Chapel Hill, NC (US); Sammy R. Shaver, Chapel Hill, NC (US); Melwyn Anthony Abreo, Jamul, CA (US); Lorenzo Josue Alfaro-Lopez, San Marcos, CA (US); Yangbo Feng, Palm Beach Gardens, FL (US); Tatyana V. Khasanova, San Diego, CA (US); Mark W. Holladay, San Diego, CA (US); Christopher S. Crean, Pittsboro, NC (US)

(73) Assignee: Inspire Pharmaceuticals, Inc., Durham, NC (US)

( * ) Notice: Subject to any disclaimer, the term of this patent is extended or adjusted under 35 U.S.C. 154(b) by 727 days.

(21) Appl. No.: 10/576,859

(22) PCT Filed: Oct. 21, 2004

(86) PCT No.: PCT/US2004/035396
§ 371 (c)(1),
(2), (4) Date: Oct. 11, 2006

(87) PCT Pub. No.: WO2005/039590
PCT Pub. Date: May 6, 2005

(65) Prior Publication Data
US 2007/0123544 A1 May 31, 2007

Related U.S. Application Data

(60) Provisional application No. 60/513,844, filed on Oct. 21, 2003.

(51) Int. Cl.
*A01N 43/04* (2006.01)
*A61K 31/70* (2006.01)

(52) U.S. Cl. ............................. 514/45; 514/42; 514/43; 514/46

(58) Field of Classification Search ...................... None
See application file for complete search history.

(56) References Cited

U.S. PATENT DOCUMENTS

| | | | | |
|---|---|---|---|---|
| 4,591,596 A | * | 5/1986 | Marconi et al. | 514/375 |
| 4,794,174 A | | 12/1988 | Secrist | 536/26 |
| 5,747,496 A | | 5/1998 | Cox et al. | 514/258 |
| 7,335,648 B2 | * | 2/2008 | Plourde et al. | 514/46 |
| 7,368,438 B2 | * | 5/2008 | Plourde et al. | 514/46 |
| 7,504,497 B2 | | 3/2009 | Douglass, III et al. | |
| 7,592,445 B2 | | 9/2009 | Plourde, Jr. et al. | |
| 2006/0121086 A1 | | 6/2006 | Boyer et al. | |

FOREIGN PATENT DOCUMENTS

| | | |
|---|---|---|
| EP | 0066918 A | 12/1982 |
| EP | 1348466 A | 10/2003 |
| WO | WO 00/04021 | 1/2000 |
| WO | WO 01/36438 | 5/2001 |
| WO | WO 01/40243 | 6/2001 |
| WO | WO 01/40246 | 6/2001 |
| WO | WO 01/94368 | 12/2001 |
| WO | WO 02/096428 | 12/2002 |

OTHER PUBLICATIONS

Baraldi et al. J. Med. Chem. (1996), vol. 39, pp. 802-806.*
Dyson, Mary; Veterinary Dermatology (1997), vol. 8, pp. 227-233.*
Baraldi, et al., "Novel $N^6$-(Substituted-phenylcarbamoyl)adenosine-5'-uronamides as Potent Agonists for $A_3$ Adenosine Receptors," *Journal of Medicinal Chemistry* 39(3): 802-806 (1996).
Brown, et al., "Matrix Metalloproteinase Inhibitors Containing a (Carboxyalkyl)amino Zinc Ligand: Modification of the P1 and P2' Residues," *J. Med. Chem.* 37(5): 674-688 (1994).
Camaioni, et al., "Adenosine Receptor Agonists: Synthesis and Biological Evaluation of the Diastereoisomers of 2-(3-Hydroxy-3-phenyl-1-propyn-1-yl)NECA," *Bioorganic & Medicinal Chemistry* 5(12): 2267-2275 (1997).
Chizh and Illes, "P2X Receptors and Nociception," *Pharmacol. Rev.* 53:4, pp. 553-568, 2000.
Collier, et al., "The Abdominal Constriction Response and Its Suppression by Analgesic Drugs in the Mouse," *B.r J. Pharmacol. Chemother.* 32: 295-310, 1968.
Cristalli, et al., "2-Aralkynyl and 2-Heteroalkynyl Derivativse of Adenosine-5'-$N$-ethyluronamide as Selective $A_{2a}$ Adenosine Receptor Agonists," *Journal of Medicinal Chemistry* 38(9): 1462-1472 (1995).
Garcia-Echeverria, C., "A base labile handle for solid phase organic chemistry," *Tetrahedron Lett.*, 38: 8933-8937 (1997).
Jacobson, et al., "Structure-Activity Relationships of 9-Alkyladenine and Ribose-Modified Adenosine Derivatives at Rat $A_3$ Adenosine Receptors," *Journal of Medicinal Chemistry* 38(10): 1720-1735 (1995).
Jarvis and Kowaluk, "Pharmacological Characterization of $P2X_3$ Homomeric and Meteromeric Channels in Nociceptive Signaling and Behavior," *Drug Development Res.*, 52:220-231, 2001.
Lee, et al., "$N$-Alkoxysulfamide, $N$-Hydroxysulfamide, and Sulfamate Analogues of Methionyl and Isoleucyl Adenylates as Inhibitors of Methionyl-tRNA and Isoleucyl-tRNA Synthetases," *Bioorganic & Medicinal Chemistry Letters* 13(6): 1087-1092 (2003).
Lyga and Secrist III, "Synthesis of Chain-Extended and C-6' Functionalized Precursors of the Nucleoside Antibiotic Sinefungin," *Journal of Organic Chemistry* 48(12): 1982-1988 (1983).
Mitsunobu, O., "The Use of Diethyl Azodicarboxylate and Triphenylphosphine in Synthesis and Transformation of Natural Products," *Synthesis* 1-28 (1981).
Santosh and Balasubramanian, "A Facile and Stereoselective Synthesis of Arylethers of Vicinal Bromohydrins by Mitsunobu Reaction," *Synthetic Communications*, 24(8): 1049-1062 (1994).
Secrist III and Talekar, "5'-C-Chain-extended Adenosine Derivatives Related to Sinefungin, Synthesis and Biological Activity," *Nucleosides & Nucleotides* 9(4): 619-627 (1990).

* cited by examiner

*Primary Examiner*—Patrick T Lewis
(74) *Attorney, Agent, or Firm*—Howrey LLP; Viola T. Kung

(57) ABSTRACT

The present invention is directed to a method of treating pain. The method comprises administering to a subject a pharmaceutical composition comprising an effective amount of a P2X receptor antagonist. The methods of the present invention are useful in reducing pain, such as traumatic pain, neuropathic pain, organ pain and/or pain associated with diseases. The P2X receptor antagonists useful for this invention are non-nucleotide compounds of general Formula I. Compounds of Formula I can be used alone to treat pain. Compounds of Formula I can also be used in conjunction with other therapeutic agents or adjunctive therapies commonly used to treat pain, thus enhancing the therapeutic effect of pain reduction.

20 Claims, No Drawings

NON-NUCLEOTIDE COMPOSITIONS AND METHOD FOR TREATING PAIN

This application is a National Stage of International Application PCT/US2004/035396, filed Oct. 21, 2004, published May 6, 2005, under PCT Article 21(2) in English; which claims the priority of U.S. Provisional Application 60/513,844, filed Oct. 21, 2003.

TECHNICAL FIELD

This invention relates to a method of treating pain. More particularly, the present invention relates to a method of treating pain with non-nucleotide P2X receptor antagonists.

BACKGROUND OF THE INVENTION

The general term "pain" is defined here to represent all categories including: traumatic pain resulting from tissue injury, post-surgical pain, burn pain, inflammatory pain; pain associated with disease such as cancer, AIDS, arthritis, herpes, migraine; pain associated with nerve damage or neuropathy, such as diabetic neuropathy, causalgia, brachial plexus avulsion, occipital neuralgia, fibromyalgia, gout, and other forms of neuralgic, neuropathic and idiopathic pain syndromes; and specific organ or tissue pain, such as ocular and corneal pain, bone pain, heart pain, skin pain, visceral (kidney, gall bladder, gastrointestinal, etc.) pain, joint pain, dental pain and muscle pain. The term "pain" also includes pain of varying severity, i.e. mild, moderate and severe pain, as well as acute and chronic pain.

In traumatic or nociceptive pain, an external stimulus causes a normal sensory response to tissue damage associated with an insult or illness, and this sensation of pain is generally responsive to narcotic analgesics such as morphine; whereas in neuropathic pain, which results from injury to the nervous system, the sensation of pain is typically not responsive to narcotic analgesics. Neuropathic pain often involves neural hypersensitivity and can persist without any overt external stimulus (Goodman & Gilman's "The Pharmacologic Basis of Therapeutics", 1996, $9^{th}$ Ed., p. 529, McGraw-Hill).

The therapeutic objective of most pain therapy is to alleviate the symptoms of pain regardless of the cause. Current therapies include the use of opioid narcotic analgesics such as morphine and fentanyl, nonsteroidal anti-inflammatory drugs (NSAIDS) such as aspirin, ibuprofen and cyclooxygenase inhibitors, or ion channel blockers such as lidocaine and novacaine. However, these therapies all have limitations. Opioids, for example, can cause tolerance, dependence, constipation, respiratory depression and sedation. NSAIDS can have gastrointestinal side effects and can increase bleeding time; in general, they are not effective in treating severe pain. Central nervous system (CNS) and cardiovascular side effects (Goodman & Gilman's "The Pharmacologic Basis of Therapeutics", $9^{th}$ Ed., 1996, p. 337, McGraw-Hill), as well as corneal damage are reported for the non-selective sodium channel blockers. Given these drawbacks to current therapies, there is clearly a need for better pain treatments.

Numerous published studies have documented the involvement of P2X nucleotide receptors in nociception. Activation of P2X receptors with agonists such as ATP or benzoylbenzoyl-ATP is associated with hyperalgesic action (Chizh and Illes, Pharmacol. Rev. 53:553-568 (2000); Jarvis and Kowaluk, Drug Development Res. 52:220-231 (2001)). Antagonism of $P2X_3$ receptors by the ATP analog, ATP-TNP, has been shown to produce antinociceptive effects in rats (Jarvis and Kowaluk, 2001).

As described above, agents commonly used to treat pain may cause adverse side effects, and thus there is a continuing need for new agents that are both safe and effective in treating pain.

SUMMARY OF THE INVENTION

The present invention is directed to a method of treating pain. The method comprises administering to a subject a pharmaceutical composition comprising an effective amount of one or more non-nucleotide P2X receptor antagonist. The methods of the present invention are useful in reducing pain such as traumatic pain, neuropathic pain, organ pain and pain associated with diseases.

The non-nucleotide P2X receptor antagonists useful for this invention comprise compounds of general Formula I, and/or tautomers thereof, and/or pharmaceutically-acceptable hydrates, solvates, and/or salts thereof.

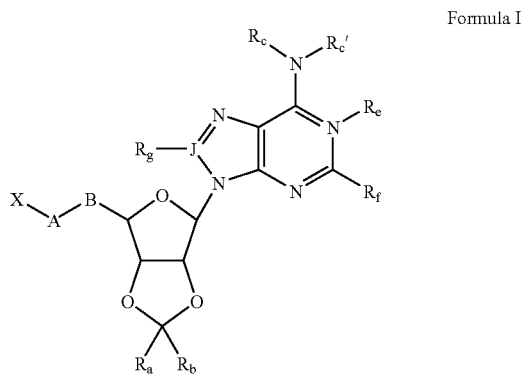

Formula I

The invention also provides novel pharmaceutical compositions comprising compounds of Formula I. The compounds of Formula I are useful in that they possess antagonist activity at P2X receptors.

The compounds of the present method can be used alone to treat pain, or the compounds of the present method can also be used in conjunction with other therapeutic agents or adjunctive therapies useful for treating pain, thus providing a beneficial therapeutic effect at lower concentrations of each pain reliever than when each is used separately.

DETAILED DESCRIPTION OF THE INVENTION

The inventors have unexpectedly discovered that by administering a non-nucleotide P2X receptor antagonist to a subject in need of pain treatment, the severity and/or incidence of pain sensation is reduced.

The present invention is directed to a method of treating pain in a subject in need of such treatment, regardless of the cause or location of the pain. The method comprises administering to a subject a pharmaceutical composition comprising an effective amount of a P2X receptor antagonist, preferably an antagonist of a $P2X_3$, $P2X_{2/3}$, $P2X_4$, or $P2X_7$ receptor, and more preferably as an antagonist of a $P2X_3$ or $P2X_{2/3}$ receptor. The methods of the present invention are useful in the treatment of traumatic pain particularly when the pain is associated with tissue damage, neuropathic pain, organ pain or pain associated with diseases. An effective amount of a P2X receptor antagonist is an amount that antagonizes the interaction of a P2X receptor with another agonist such as ATP, leading to a reduction of nociception and ameliorating the symptoms of pain. The effect of treating pain can be measured in a method such as, but not limited to, abdominal constriction (Collier, et al., *Br. J. Pharmacol. Chemother.* 32: 295-310 (1968)).

The present invention provides a method to alleviate the symptoms of pain. The general term "pain" treatable by the present method includes traumatic pain, neuropathic pain, organ pain, and pain associated with diseases. Traumatic pain includes pain resulting from injury, post-surgical pain, burn pain and inflammatory pain. Neuropathic pain includes, but is not limited to, neuropathic and idiopathic pain syndromes, and pain associated with neuropathy such as diabetic neuropathy, causalgia, brachial plexus avulsion, occipital neuralgia, fibromyalgia, gout, and other forms of neuralgia. Organ pain includes, but is not limited to, ocular, corneal, bone, heart, skin, visceral (kidney, gall bladder, gastrointestinal, etc.), joint, dental and muscle pain. Pain associated with diseases includes, but is not limited to, pain associated with cancer, AIDS, arthritis, herpes, sickle cell anemia and migraine. The present invention reduces pain of varying severity, (i.e. mild, moderate and severe pain) as well as both acute and chronic pain.

The P2X receptor antagonists useful for this invention include compounds of Formula I, or a tautomer thereof, or a pharmaceutically-acceptable salt, -hydrate, or -solvate thereof:

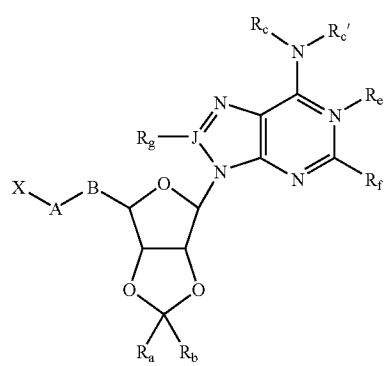

Formula I wherein $R_a$ and $R_b$ are each independently selected from the group consisting of: hydrogen, (saturated or unsaturated) $C_{1-8}$ alkyl, (saturated or unsaturated) $C_{3-7}$ cycloalkyl, aralkyl (including saturation and/or unsaturation in the alkylene portion), aryl, and (saturated or unsaturated) $C_{2-6}$ heterocycle; or $R_a$ and $R_b$ can be taken together to form a ring of 3 to 7 members, with or without substitution, and with or without heteroatoms in place of ring carbon atoms;

$R_c$ and $R_c'$ are independently selected from the group consisting of: H, OR, (saturated or unsaturated) $C_{1-8}$ alkyl, (saturated or unsaturated) $C_{3-7}$ cycloalkyl, aralkyl (including saturation and/or unsaturation in the alkylene portion), aryl, (saturated or unsaturated) heterocycle, and —C(G)Σ; wherein G=O, S or $NR_d$; and Σ=L, $R_d$, $OR_d$, or $N(R_d)_2$; except that —$NR_cR_c'$ cannot be —$N(OR)_2$; and $OR_d$ cannot be —OH; each $R_d$ is independently selected from the group consisting of: H, (saturated or unsaturated) $C_{1-8}$ alkyl, (saturated or unsaturated) $C_{3-7}$ cycloalkyl, aralkyl (including saturation and/or unsaturation in the alkylene portion), aryl, heteroaryl, and (saturated or unsaturated) $C_{2-6}$ heterocycle; or two $R_d$ groups can be taken together to form a ring of 4 to 7 members, with or without unsaturation and with or without heteroatoms in place of ring-carbon units; or one $R_d$ and one of $R_c$ or $R_c'$ can be taken together to form a ring of 4 to 7 members, with or without unsaturation and with or without heteroatoms in place of ring-carbon units;

R is selected from the group consisting of: H, (saturated or unsaturated) $C_{1-8}$ alkyl, (saturated or unsaturated) $C_{3-7}$ cycloalkyl, aryl, aralkyl (including saturation and/or unsaturation in the alkylene portion), heteroaryl, and (saturated or unsaturated) $C_{2-6}$ heterocycle;

L is selected from the group consisting of: H, —$CF_3$, —$CF_2CF_3$, (saturated or unsaturated) $C_{1-8}$ alkyl, (saturated or unsaturated) $C_{3-7}$ cycloalkyl, aryl, aralkyl (including saturation and/or unsaturation in the alkylene portion), heteroaryl, (saturated or unsaturated) $C_{2-6}$ heterocycle, (saturated or unsaturated) $C_{1-6}$ alkoxy, aralkoxy, aryloxy, N,N-disubstituted-amino, N-substituted amino, and unsubstituted-amino;

when L is N-substituted-amino, or N,N-disubstituted-amino, each substituent of said amino group of L is selected from the group consisting of: $C_{1-8}$ alkyl, $C_{3-7}$ cycloalkyl, aryl, aralkyl, heteroaryl, and (saturated or unsaturated) $C_{2-6}$ heterocycle;

when L is N,N-disubstituted-amino, the two substituents independently selected from the group above can then be taken together to form a ring of 3 to 7 members, wherein said formed ring thereon bears the remaining features of said selected substituents before said ring formation;

$R_e$=O or absent;

$R_f$=H, halogen, (saturated or unsaturated) $C_{1-8}$ alkyl, (saturated or unsaturated) $C_{3-7}$ cycloalkyl, aryl, aralkyl (including saturation and/or unsaturation in the alkylene portion), heteroaryl, (saturated or unsaturated) $C_{2-6}$ heterocycle, —OH, (saturated or unsaturated) $C_{1-6}$ alkoxy, aryloxy, —SH, $C_{1-6}$ thioalkyl, thioaryl, —[(CO)OR], —[(CO)NRR], amino, —N-substituted amino, or N,N-disubstituted amino; wherein each said substituent on said N-substituted-amino-group, or N,N-disubstituted-amino-group of $R_f$ is independently selected from the group consisting of: $C_{1-8}$ alkyl, $C_{3-7}$ cycloalkyl, aryl, aralkyl, heteroaryl, $C_{2-6}$ heterocycle, —[(CO)R] and —[(CO)—NRR]; wherein each R is independently as defined above; or when $R_f$ is —[(CO)NRR], —[NH(CO)NRR], —[N($C_{1-8}$ alkyl)(CO)NRR], —[N(aryl)(CO)NRR], or [N(aralkyl)(CO)NRR], the R groups of a said —NRR unit (N,N-disubstituted-amino group) in $R_f$ can be taken together such that a ring of 3 to 7 members is formed, with or without heteroatoms in place of the ring-carbon units;

J=N or C, with the proviso that when J=N, then $R_g$ is absent;

when J=C, $R_g$ is selected from the group consisting of: —H, halogen, (saturated or unsaturated) $C_{1-8}$ alkyl, (saturated or unsaturated) $C_{3-7}$ cycloalkyl, aralkyl (including saturation and/or unsaturation in the alkylene portion), aryl, —OH, (saturated or unsaturated) $C_{1-6}$ alkoxy, aryloxy, —SH, $C_{1-6}$ thioalkyl, thioaryl, —[(CO)OR], —[(CO)NRR], and —NRR; wherein each R is independently as defined above; or when $R_g$ is —[(CO)NRR] or —NRR, the R groups of said —NRR unit (N,N-disubstituted-amino group) in $R_g$ can be taken together such that a ring of 3 to 7 members is formed, with or without heteroatoms in place of the ring-carbon units;

A and B are each independently selected from the group consisting of: —$C_{1-3}$ alkylene-, —$CF_2$—, and —(CO)—; wherein each said —$C_{1-3}$ alkylene- unit of A and B independently can be saturated or unsaturated, and each carbon of a —C$_{1-3}$ alkylene- unit of B independently can be substituted with 0 to 2 fluorine groups, 0 to 1 methyl groups, 0 to 2 —[(CO)OR] groups, and 0 to 1 —(OR) groups; or B is absent; or one substitution of a heteroatom-containing-unit selected from the group: —O—, —S—, —NR—, —[NR(CO)]— or —N[(CO)L]—, where each R and L is independently as defined above, can be made for any one-carbon-unit within either or both of said C$_{1-3}$ alkylene units of A and B, provided that fewer than three said heteroatom-containing-unit for one-carbon-unit substitutions on the -A-B— chain are made, no —S—S— or —O—O— bonds are formed in the X-A-B— chain by said substitution or substitutions of a heteroatom-containing-unit for a one-carbon-unit on the -A-B— chain, and no said heteroatom substitution is made such that the said replacement heteroatom connects directly to the tetrahydrofuran ring shown in Formula I;

X=—OR, —SR, —S(O)L, —S(O$_2$)L, —SO$_3$H, —S(O$_2$)NRR, —S(O$_2$)NR(CO)L, —NRR, —NR(CO)L, —N[(CO)L]$_2$, —NR(SO$_2$)L, —NR(CO)NR(SO$_2$)L, —NR(SO$_2$)NRR, or —NR(SO$_2$)NR(CO)L;

wherein each R and L is independently as defined above;

wherein the R groups of a —NRR unit (N,N-disubstituted-amino group) in X can be taken together such that a ring of 3 to 7 members is formed, with or without heteroatoms in place of the ring-carbon units;

with the proviso that no compound in Formula I contains: a halogen-group, hydroxy-group, sulfhydryl-group, or amino-group (—NH$_2$, N-substituted-amino, or N,N-disubstituted-amino) attached to an sp$^3$-hybridized-carbon atom that is bonded directly to a heteroatom selected from the group consisting of O, S and N, as compounds in this class (e.g., —[C(OH)(SR)]—, —[CCl(NRR)]—, etc.), in general have lower chemical stability;

the first exception to this proviso is: compounds in which the said sp$^3$-hybridized-carbon atom is bonded directly to: 1) a sulfur atom which is part of a —[S(O)]— group (sulfinyl group), or a —[S(O$_2$)]-group (sulfonyl group), and also to: 2) one or more halogen groups; (an example of a moiety having this arrangement is the trifluoromethanesulfonyl group);

the second and final exception to this proviso is the C-1' position of the furanose of compounds of Formula I wherein the sp$^3$-hybridized carbon atom at the 1'-position is attached to: 1) the oxygen atom of the furanose ring and to: 2) the nitrogen atom of the adenine or 8-azaadenine moiety; or X is a group as provided in Formula II:

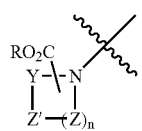

Formula II wherein:

n=1 to 4, inclusive;

Y, Z and Z' are independently selected from —CRR$_f$—, —NR—, —[N(CO)L]-, —O— and —S—; or the said —Y—Z'-unit, taken together, can be selected to be a —N=N— unit or a —CR=CR$_f$— unit; or any -(Z)$_2$-unit or subunit of —(Z)$_n$ can be selected to be a —CR=CR$_f$— unit;

and with the provisos that the ring shown in Formula II contains no more than three heteroatoms, and that the shown pendant —CO$_2$R unit in Formula II is a substituent on the ring described in Formula II, and that the ring of Formula II:contains no halogen-group, hydroxy-group, sulfhydryl-group, or amino-group (—NH$_2$, N-substituted-amino, or N, N-disubstituted-amino) attached to an sp$^3$-hybridized-carbon atom that is bonded directly to a heteroatom selected from the group consisting of O, S, and N, as such types of compounds are unstable in many cases.

Preferably, the furanosyl moiety in Formula I has the 2'- and 3'-oxygen-groups in a cis-orientation, relative to one another on the furanose ring. Further, a furanosyl moiety which supports a 2', 3'-acetal or -ketal group is, preferably, derived from ribose; other furanose derivatives can be used, however. A preferred stereochemical embodiment of this invention includes, but is not limited to (D)-ribose-(2', 3'-acetal or -ketal) compounds of Formula I, such as found in acetals derived from (-)-adenosine.

In one embodiment of the method, the compound of Formula I is selected from the group consisting of: 6-[6-(3-Cyclopropyl-ureido)-purin-9-yl]-2-styryl-tetrahydro-furo[3,4-d][1,3]dioxole-4-carboxylic acid; 6-[6-(3-Ethyl-ureido)-purin-9-yl]-2-styryl-tetrahydro-furo[3,4-d][1,3]dioxole-4-carboxylic acid; 6-[6-(3-Butyl-ureido)-purin-9-yl]-2-styryl-tetrahydro-furo[3,4-d][1,3]dioxole-4-carboxylic acid; 6-[6-(3-Propyl-ureido)-purin-9-yl]-2-styryl-tetrahydro-furo[3,4-d][1,3]dioxole-4-carboxylic acid; 2-[({6-[6-(3-Ethyl-ureido)-purin-9-yl]-2-styryl-tetrahydro-furo[3,4-d][1,3]dioxol-4-ylmethyl}-amino)-methyl]-cyclopropanecarboxylic acid; 3-{6-[6-(3-Ethyl-ureido)-purin-9-yl]-2-styryl-tetrahydro-furo[3,4-d][1,3]dioxol-4-ylmethyl}-3H-[1,2,3]triazole-4-carboxylic acid; 3-{6-[6-(3-Ethyl-ureido)-purin-9-yl]-2-styryl-tetrahydro-furo[3,4-d][1,3]dioxol-4-yl}-propionic acid; {6-[6-(3-Ethyl-ureido)-purin-9-yl]-2-styryl-tetrahydro-furo[3,4-d][1,3]dioxol-4-yl}-acetic acid; 1-{6-[6-(3-Cyclopentyl-ureido)-purin-9-yl]-2-phenyl-tetrahydro-furo[3,4-d][1,3]dioxole-4-carbonyl}-pyrrolidine-2-carboxylic acid; {6-[6-(3-Ethyl-ureido)-purin-9-yl]-2-phenyl-tetrahydro-furo[3,4-d][1,3]dioxol-4-yl)-acetic acid; {6-[6-(3-Cyclopentyl-ureido)-purin-9-yl]-2-phenyl-tetrahydro-furo[3,4-d][1,3]dioxol-4-yl}-acetic acid; 3-{6-[6-(3-Ethyl-ureido)-purin-9-yl]-2-phenyl-tetrahydro-furo[3,4-d][1,3]dioxol-4-yl}-propionic acid; 3-{6-[6-(3-Ethyl-ureido)-purin-9-yl]-2-styryl-tetrahydro-furo[3,4-d][1,3]dioxol-4-ylmethoxymethyl}-benzoic acid; ({6-[6-(3-Ethyl-ureido)-purin-9-yl]-2-styryl-tetrahydro-furo[3,4-d][1,3]dioxol-4-ylmethyl}-amino)-acetic acid; 1-Ethyl-3-[9-(6-hydroxymethyl-2-styryl-tetrahydro-furo[3,4-d][1,3]dioxol-4-yl)-8-iodo-9H-purin-6-yl]-urea; 1-Ethyl-3-{9-[6-(2-hydroxy-ethoxymethyl)-2-styryl-tetrahydro-furo[3,4-d][1,3]dioxol-4-yl]-8-iodo-9H-purin-6-yl}-urea; 1-Ethyl-3-{9-[6-(2-hydroxy-ethyl)-2-styryl-tetrahydro-furo[3,4-d][1,3]dioxol-4-yl]-8-iodo-9H-purin-6-yl}-urea; 2-{6-[6-(3-Ethyl-ureido)-purin-9-yl]-2-styryl-tetrahydro-furo[3,4-d][1,3]dioxol-4-ylmethoxy}-nicotinic acid; 5-{6-[6-(3-Ethyl-ureido)-purin-9-yl]-2-styryl-tetrahydro-furo[3,4-d][1,3]dioxol-4-ylmethoxy}-pentanoic acid; 1-Ethyl-3-{9-[6-(2-hydroxy-propane-1-sulfonylmethyl)-2-styryl-tetrahydro-furo[3,4-d][1,3]dioxol-4-yl]-9H-purin-6-yl}-urea; 1-Ethyl-3-{9-[6-(2-methanesulfonylmethyl-pyrrolidine-1-carbonyl)-2-styryl-tetrahydro-furo[3,4-d][1,3]dioxol-4-yl]-9H-purin-6-yl}-urea; 1-Ethyl-3-{9-[6-(2-methanesulfonylmethyl-pyrrolidine-1-carbonyl)-2-phenyl-tetrahydro-furo[3,4-d][1,3]dioxol-4-yl]-9H-purin-6-yl}-urea; 1-Cyclopentyl-3-{9-[6-(2-methanesulfonylmethyl-pyrrolidine-1-carbonyl)-2- phenyl-tetrahydro-furo[3,4-d][1,3]dioxol-4-yl]-9H-purin-6-yl}-urea; 6-[6-(3-Ethyl-ureido)-8-iodo-purin-9-yl]-2-styryl-tetrahydro-furo[3,4-d][1,3]dioxole-4-carboxylic acid; 3-{6-[6-(3-Ethyl-ureido)-purin-9-yl]-2-styryl-tetrahydro-furo[3,4-d][1,3]dioxol-4-yl}-2-hydroxy-propionic acid; and 3-{6-[6-(3-Ethyl-ureido)-purin-9-yl]-2-styryl-tetrahydro-furo[3,4-d][1,3]dioxol-4-yl}-2-oxo-propionic acid; or a pharmaceutically-acceptable salt, -hydrate, or -solvate thereof.

A particularly useful embodiment is where X in Formula II has a —$CO_2H$ group on the ring.

In another embodiment, the compound is selected from the group consisting of: 3-{6-[6-(3-Ethyl-1-phenyl-ureido)-purin-9-yl]-2,2-dimethyl-tetrahydro-furo[3,4-d][1,3]dioxol-4-ylmethoxy}-isoxazole-5-carboxylic acid; 3-(6-{6-[3-Ethyl-1-(5-methyl-furan-2-ylmethyl)-ureido]-purin-9-yl}-2,2-dimethyl-tetrahydro-furo[3,4-d][1,3]dioxol-4-ylmethoxy)-isoxazole-5-carboxylic acid; 3-{2,2-Dimethyl-6-[6-(3-phenyl-ureido)-purin-9-yl]-tetrahydro-furo[3,4-d][1,3]dioxol-4-ylmethoxy}-isoxazole-5-carboxylic acid; 3-{2,2-Dimethyl-6-[6-(3-phenyl-1-propyl-ureido)-purin-9-yl]-tetrahydro-furo[3,4-d][1,3]dioxol-4-ylmethoxy}-isoxazole-5-carboxylic acid; 5-Amino-2-{2,2-dimethyl-6-[6-(3-phenyl-ureido)-purin-9-yl]-tetrahydro-furo[3,4-d][1,3]dioxol-4-ylmethoxy}-N-hydroxy-benzamide; 6-{2,2-Dimethyl-6-[6-(3-phenyl-ureido)-purin-9-yl]-tetrahydro-furo[3,4-d][1,3]dioxol-4-ylmethoxy}-nicotinamide; 1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea; 3-({2,2-Dimethyl-6-[6-(3-phenyl-ureido)-purin-9-yl]-tetrahydro-furo[3,4-d][1,3]dioxole-4-carbonyl}-amino)-benzoic acid; 2-({2-Benzyl-6-[6-(3-phenyl-ureido)-purin-9-yl]-tetrahydro-furo[3,4-d][1,3]dioxole-4-carbonyl}-amino)-3-hydroxy-propionic acid; N-{2-Benzyl-6-[6-(3-phenyl-ureido)-purin-9-yl]-tetrahydro-furo[3,4-d]([1,3]dioxole-4-carbonyl}-methanesulfonamide; 1-[9-(2-Benzyl-6-ureidomethyl-tetrahydro-furo[3,4-d][1,3]dioxol-4-yl)-9H-purin-6-yl]-3-phenyl-urea methylsulfonamide; 3-{2,2-Dimethyl-6-[6-(3-phenyl-ureido)-purin-9-yl]-tetrahydro-furo[3,4-d][1,3]dioxol-4-yl}-acrylic acid methyl ester; 3-{2,2-Dimethyl-6-[6-(3-phenyl-ureido)-purin-9-yl]-tetrahydro-furo[3,4-d][1,3]dioxol-4-yl}-propionic acid methyl ester; 3-{2,2-Dimethyl-6-[6-(3-phenyl-ureido)-purin-9-yl]-tetrahydro-furo[3,4-d][1,3]dioxol-4-yl}-propionic acid; and 3-(3-{2,2-Dimethyl-6-[6-(3-phenyl-ureido)-purin-9-yl]-tetrahydro-furo[3,4-d][1,3]dioxol-4-yl}-propionylamino)-benzoic acid; or a pharmaceutically-acceptable salt, -hydrate, or -solvate thereof.

In another embodiment of the method, $R_b$ of Formula I is selected from the group consisting of: hydrogen, saturated or unsaturated $C_{2-8}$ alkyl, saturated or unsaturated $C_{3-7}$ cycloalkyl, aralkyl (including saturation and/or unsaturation in the alkyl portion), aryl, and $C_{2-6}$ heterocycle; where all rings or chains optionally can bear one or more desired substituents.

In another embodiment of the method, X of Formula I is selected from the group consisting of: —OR, —SR, —NRR, —NR(CO)L, —NR($SO_2$)L, —NR(CO)NR($SO_2$)L, —NR($SO_2$)NR(CO)L, and a moiety as provided in Formula II; Y, Z and Z' are independently selected from —$CRR_f$—, —O— and —S—; or the said —Y—Z'—, —$(Z)_2$—, —$(Z)_3$—, and —$(Z)_4$-units are selected from the respective said —Y—Z'-units and —$(Z)_n$-units as provided in Formula II.

In another embodiment of the method, compounds of general Formula I are molecules whose structures fall within the definition of Formula III:

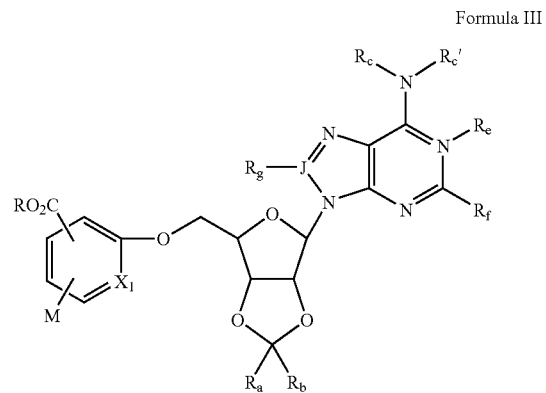

Formula III wherein $R_a$, $R_b$, $R_c$, $R_{c'}$, Σ, R, L, $R_d$, $R_e$, $R_f$, J, $R_g$ are as defined in Formula I;

$X_1$ is selected from the group consisting of: N (nitrogen) and C-M; and

M is independently selected from the group consisting of: —H, halogen, $CF_3$, (saturated or unsaturated) $C_{1-8}$ alkyl, (saturated or unsaturated) $C_{3-7}$ cycloalkyl, aryl, aralkyl, heteroaryl, (saturated or unsaturated) $C_{2-6}$ heterocycle, —OH, $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: (saturated or unsaturated) $C_{1-8}$ alkyl, (saturated or unsaturated) $C_{3-7}$ cycloalkyl, aryl, aralkyl, heteroaryl, (saturated or unsaturated) $C_{2-6}$ heterocycle, —[(CO)R], —[(CO)O—($C_{1-8}$ alkyl)], and —[(CO)—NRR]; and when M is —[(CO)NRR], —[NH(CO)NRR], —[N($C_{1-8}$ alkyl)(CO)NRR], —[N(aryl)(CO)NRR], or —[N(aralkyl)(CO)NRR], the R groups of any said —NRR unit (N,N-disubstituted-amino group) in M can be taken together such that a ring of 3 to 7 members is formed, with or without heteroatoms in place of the ring-carbon units; or a tautomer, or a pharmaceutically-acceptable salt, -hydrate, or -solvate thereof.

Another usefull group of compounds are those of Formula III where the R group is H.

Examples of Formula III compounds are 5-Amino-2-{2,2-dimethyl-6-[6-(3-phenyl-ureido)-purin-9-yl]-tetrahydro-furo[3,4-d][1,3]dioxol-4-ylmethoxy}-benzoic acid; 4-{2,2-Dimethyl-6-[6-(3-phenyl-ureido)-purin-9-yl]-tetrahydro-furo[3,4-d][1,3]dioxol-4-ylmethoxy}-isophthalic acid; 4-{2,2-Dimethyl-6-[6-(3-phenyl-ureido)-purin-9-yl]-tetrahydro-furo[3,4-d][1,3]dioxol-4-ylmethoxy}-benzoic acid; 6-{2,2-Dimethyl-6-[6-(3-phenyl-ureido)-purin-9-yl]-tetrahydro-furo[3,4-d][1,3]dioxol-4-ylmethoxy}-nicotinic acid; 5-Chloro-6-{2,2-dimethyl-6-[6-(3-phenyl-ureido)-purin-9-yl]-tetrahydro-furo[3,4-d][1,3]dioxol-4-ylmethoxy}-nicotinic acid; 2-{2,2-Dimethyl-6-[6-(3-phenyl-ureido)-purin-9-yl]-tetrahydro-furo[3,4-d][1,3]dioxol-4-ylmethoxy}-nicotinic acid; 6-Chloro-2-(2,2-dimethyl-6-[6-(3-phenyl-ureido)-purin-9-yl]-tetrahydro-furo[3,4-d][1,3]dioxol-4-ylmethoxy}-5-fluoro-nicotinic acid; 6-Chloro-2-{2,2-dimethyl-6-[6-(3-phenyl-ureido)-purin-9-yl]-tetrahydro-furo[3,4-d][1,3]dioxol-4-ylmethoxy}-5-fluoro-nicotinic acid; 2-[6-[6-(3-Phenyl-ureido)-purin-9-yl]-2-(2-trifluoromethyl-phenyl)-tetrahydro-furo[3,4-d][1,3]dioxol-4-yl-methoxy]-nicotinic acid; 2-{2-Phenyl-6-[6-(3-phenyl-ureido)-purin-9-yl]-tetrahydro-furo[3,4-d][1,3]dioxol-4-ylmethoxy}-nicotinic acid; 2-{2-Biphenyl-3-yl-6-[6-(3-phenyl-ureido)-purin-9-yl]-tetrahydro-furo[3,4-d][1,3]dioxol-4-ylmethoxy}-nicotinic acid; 2-{2-Naphthalen-2-yl-6-[6-(3-phenyl-ureido)-purin-9-yl]-tetrahydro-furo[3,4-d][1,3]dioxol-4-ylmethoxy}-nicotinic acid; 2-{2-Benzo[b]thiophen-3-yl-6-[6-(3-phenyl-ureido)-purin-9-yl]-tetrahydro-furo[3,4-d][1,3]dioxol-4-ylmethoxy)-nicotinic acid; 2-{6-[6-(3-Hexyl-ureido)-purin-9-yl]-2-phenyl-tetrahydro-furo[3,4-d][1,3]dioxol-4-ylmethoxy}-nicotinic acid; 2-{2,2-Dimethyl-6-[6-(3-phenyl-ureido)-purin-9-yl]-tetrahydro-furo[3,4-d][1,3]dioxo-spiroindan-4-ylmethoxy}-nicotinic acid; 2-{6-[6-(3-Ethyl-ureido)-purin-9-yl]-2-phenethyl-tetrahydro-furo[3,4-d][1,3]dioxol-4-ylmethoxy}-nicotinic acid; 2-{6-[6-(3-Ethyl-ureido)-purin-9-yl]-2-phenylethynyl-tetrahydro-furo[3,4-d][1,3]dioxol-4-ylmethoxy}-nicotinic acid; 2-{6-[6-(3-Ethyl-ureido)-purin-9-yl]-2-phenyl-tetrahydro-furo[3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo[3,4-d][1,3]dioxol-4-ylmethoxy}-nicotinic acid; 2-{6-[6-(3-Cyclopentyl-ureido)-purin-9-yl]-2-phenethyl-tetrahydro-furo[3,4-d][1,3]dioxol-4-ylmethoxy}-nicotinic acid; 2-{6-[6-(3-Cyclopentyl-ureido)-purin-9-yl]-2,2-(3,4-Dihydro-1H-naphthalen)-tetrahydro-furo[3,4-d][1,3]dioxol-4-ylmethoxy}-nicotinic acid; 2-{6-[6-(3-Cyclopentyl-ureido)-purin-9-yl]-2-p-tolyl-tetrahydro-furo[3,4-d][1,3]dioxol-4-ylmethoxy}-nicotinic acid; 2-{2-Biphenyl-4-yl-6-[6-(3-hexyl-ureido)-purin-9-yl]-tetrahydro-furo[3,4-d][1,3]dioxol-4-ylmethoxy}-nicotinic acid; 2-{2-(4-Acetylamino-phenyl)-6-[6-(3-cyclopentyl-ureido)-purin-9-yl]-tetrahydro-furo[3,4-d][1,3]dioxol-4-ylmethoxy}-nicotinic acid; and 2-{2-tert-Butyl-6-[6-(3-phenyl-ureido)-purin-9-yl]-tetrahydro-furo[3,4-d][1,3]dioxol-4-ylmethoxy}-nicotinic acid; or a pharmaceutically-acceptable salt, -hydrate, or -solvate thereof.

In another embodiment of the method, useful compounds fall within the definition of Formula IV:

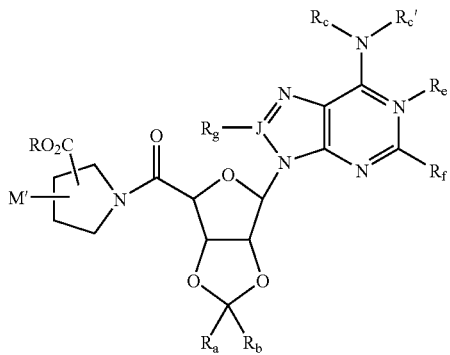

Formula IV wherein $R_a$, $R_b$, $R_c$, $R_c'$, R, Σ, R, L, $R_d$, $R_e$, $R_f$, J, $R_g$ are as defined in Formula I; and M' is as defined for M;

the M' and —$CO_2R$ groups are independently attached to any carbon of the pyrrolidine ring; and M' is not a halogen, hydroxy, sulfhydryl, or amino group when M' is attached to a carbon that is bonded to the pyrollidine nitrogen atom (alpha position); or a tautomer, or a pharmaceutically-acceptable salt, -hydrate, or -solvate thereof.

Another useful group of compounds are those of Formula IV where R═H.

Examples of Formula IV compounds are 1-{2-Phenyl-6-[6-(3-phenyl-ureido)-purin-9-yl]-tetrahydro-furo[3,4-d][1,3]dioxole-4-carbonyl}-pyrrolidine-2-carboxylic acid; 1-{2-Phenyl-6-[6-(3-phenyl-ureido)-purin-9-yl]-tetrahydro-furo[3,4-d][1,3]dioxole-4-carbonyl}-pyrrolidine-2-carboxylic acid; 1-{2-Benzyl-6-[6-(3-ethyl-ureido)-purin-9-yl]-tetrahydro-furo[3,4-d][1,3]dioxole-4-carbonyl}-pyrrolidine-2-carboxylic acid; 1-(2-Phenyl-6-{6-[3-(2-phenyl-cyclopropyl)-ureido]-purin-9-yl}-tetrahydro-furo[3,4-d][1,3]dioxole-4-carbonyl)-pyrrolidine-2-carboxylic acid; 1-{6-[6-(3-Benzyl-ureido)-purin-9-yl]-2-phenyl-tetrahydro-furo[3,4-d][1,3]dioxole-4-carbonyl}-pyrrolidine-2-carboxylic acid; 1-{2-Benzo[b]thiophen-3-yl-6-[6-(3-hexyl-ureido)-purin-9-yl]-tetrahydro-furo[3,4-d][1,3]dioxole-4-carbonyl}-pyrrolidine-2-carboxylic acid; 1-{2-Benzyl-6-[6-(3-hexyl-ureido)-purin-9-yl]-tetrahydro-furo[3,4-d][1,3]dioxole-4-carbonyl}-pyrrolidine-2-carboxylic acid; 1-{6-[6-(3-Ethyl-ureido)-purin-9-yl]-2-naphthalen-2-yl-tetrahydro-furo[3,4-d][1,3]dioxole-4-carbonyl}-pyrrolidine-2-carboxylic acid; 1-{6-[6-(3-Hexyl-ureido)-purin-9-yl]-2-phenyl-tetrahydro-furo[3,4-d][1,3]dioxole-4-carbonyl}-pyrrolidine-2-carboxylic acid; 1-{6-[6-(3-Cyclopentyl-ureido)-purin-9-yl]-2-phenyl-tetrahydro-furo[3,4-d][1,3]dioxole-4-carbonyl}-pyrrolidine-2-carboxylic acid; and 1-(3-{2,2-Dimethyl-6-[6-(3-phenyl-ureido)-purin-9-yl]-tetrahydro-furo[3,4-d][1,3]dioxol-4-yl}-propionyl)-pyrrolidine-2-carboxylic acid; or a pharmaceutically-acceptable salt, -hydrate, or -solvate thereof.

Other groups of compounds useful for the method are included under Formulas V-XI, or pharmaceutically acceptable salts, solvates, or hydrates thereof; in which R, $R_a$, $R_b$, J and $R_g$, are defined as for Formula I, and n is defined as for Formula II.

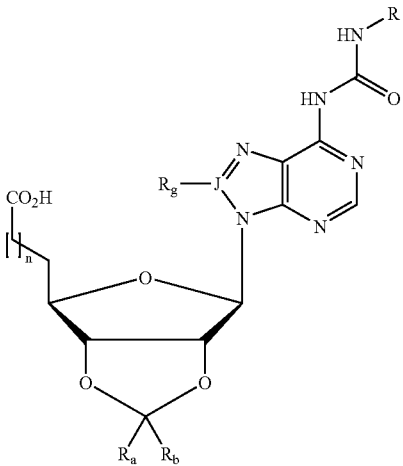

Formula V

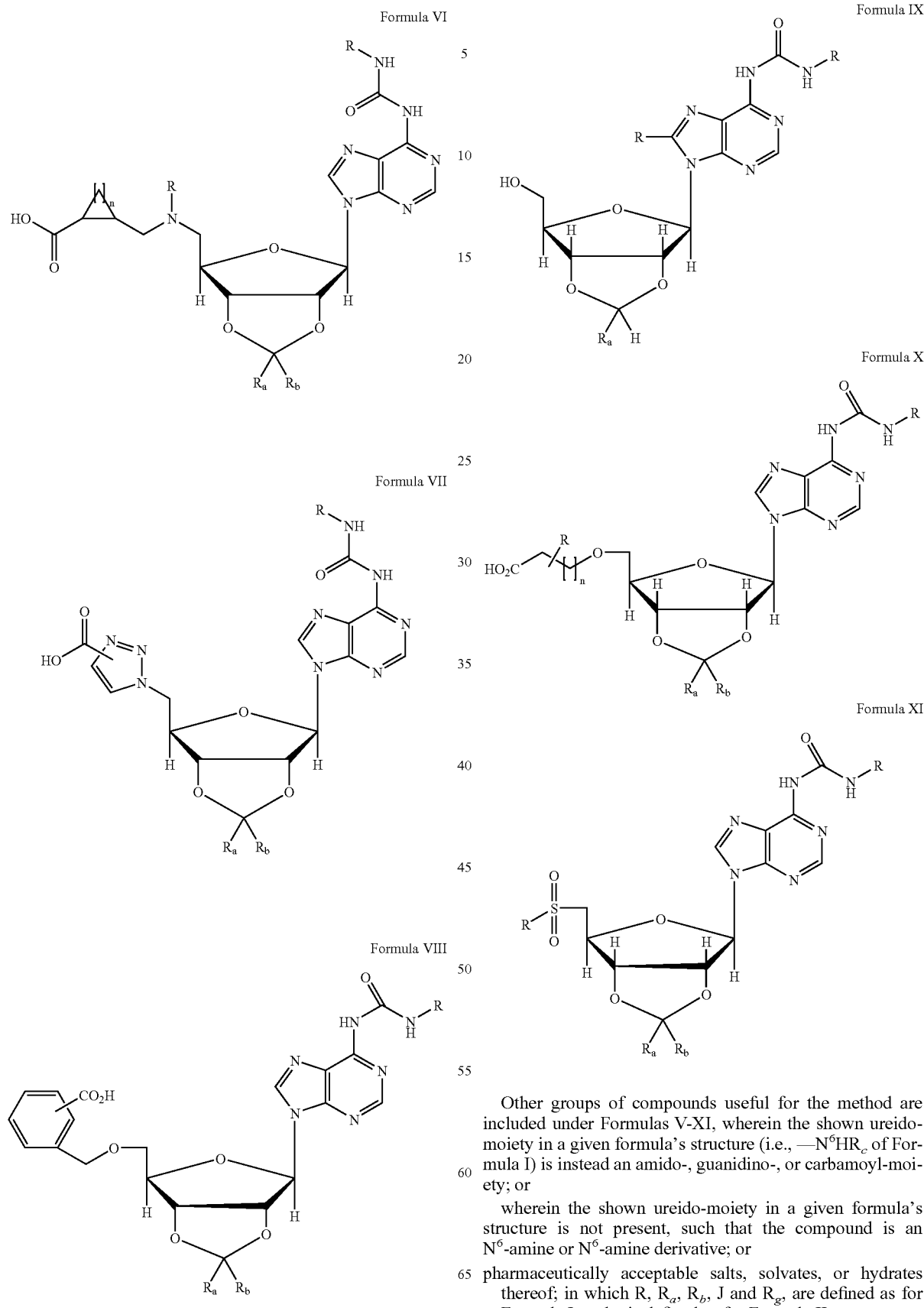

Other groups of compounds useful for the method are included under Formulas V-XI, wherein the shown ureido-moiety in a given formula's structure (i.e., —N⁶HR_c of Formula I) is instead an amido-, guanidino-, or carbamoyl-moiety; or wherein the shown ureido-moiety in a given formula's structure is not present, such that the compound is an $N^6$-amine or $N^6$-amine derivative; or pharmaceutically acceptable salts, solvates, or hydrates thereof; in which R, $R_a$, $R_b$, J and $R_g$, are defined as for Formula I, and n is defined as for Formula II.

One embodiment of the present invention is a method to reduce pain through inhibition of P2X receptors with preferred compounds that are furanose-modified adenosine analogues and/or their 8-aza-analogues.

Novel Compositions

The present invention also provides novel compounds of Formulas I, III, IV, V, VI, VII, VIII, IV, X, or XI, respectively, with the further provisos that for compounds of Formula I:

(a) when $R_a$=Me, $R_e$=nothing, $R_f$=H, I or Cl, $R_g$=H, J=C, and the unit —($R_c$)N—(CG)—$NR_dR_d$—=HN—(CO)—NH-(aryl), —HN—(CO)—NH-(heteroaryl), —HN—(CO)—NH-(n-octyl), or —HN—(CO)—NH-(t-butyl), then $R_b$ is not equal to Me; or (b) when $R_a$=$R_b$=Me, $R_e$=nothing, $R_f$=$R_g$=H, J=C, and the unit $R_c$—N—(CG)—$NR_dR_d$—'=(R')—N—(CO)—N(R")(R'''), wherein R' is H, alkyl, substituted alkyl, heteroaryl-NH—(CG')—, or aryl-NH—(CG')—, G' is selected from the group consisting of: O, NR and S; R" is H, alkyl, substituted alkyl, or aryl; and R''' is heteroaryl, aralkyl, or aryl, then the unit X-A-B— is not R—NH—(CO)—, unless said R—NH—(CO)— contains at least one —CO$_2$H group as a substitutent on a ring or chain of said R; or (c) when the unit X-A-B—=H(CO)—, RO(CO)—, ROCH$_2$—, RSCH$_2$—, RRNCH$_2$— then one of $R_a$ or $R_b$ must be H, and the other $R_b$ or $R_a$ is not H, Ph, Me or Et.

A further proviso for compounds of Formula V is: wherein at least one of $R_a$ and $R_b$ is not methyl.

A desired substituent on a chain or ring (in place of a hydrogen at a position) is one selected from the given alkyl, aryl, halogen, aralkyl, carboxy, alkoxycarbonyl, hydroxyl, acyloxy, alkoxy, aryloxy or aralkoxy classes or from other classes, which provides a compound with good-to-excellent P2Y$_{12}$ receptor-binding properties, but which does not yield a compound with undesirable properties like chemical instability in a formulation, or one with levels of toxicity that are not well-tolerated by a treated mammal, or especially, not well-tolerated by a human.

Exemplary compounds for the present invention are shown in Table 1.

TABLE 1

Exemplary Compounds.

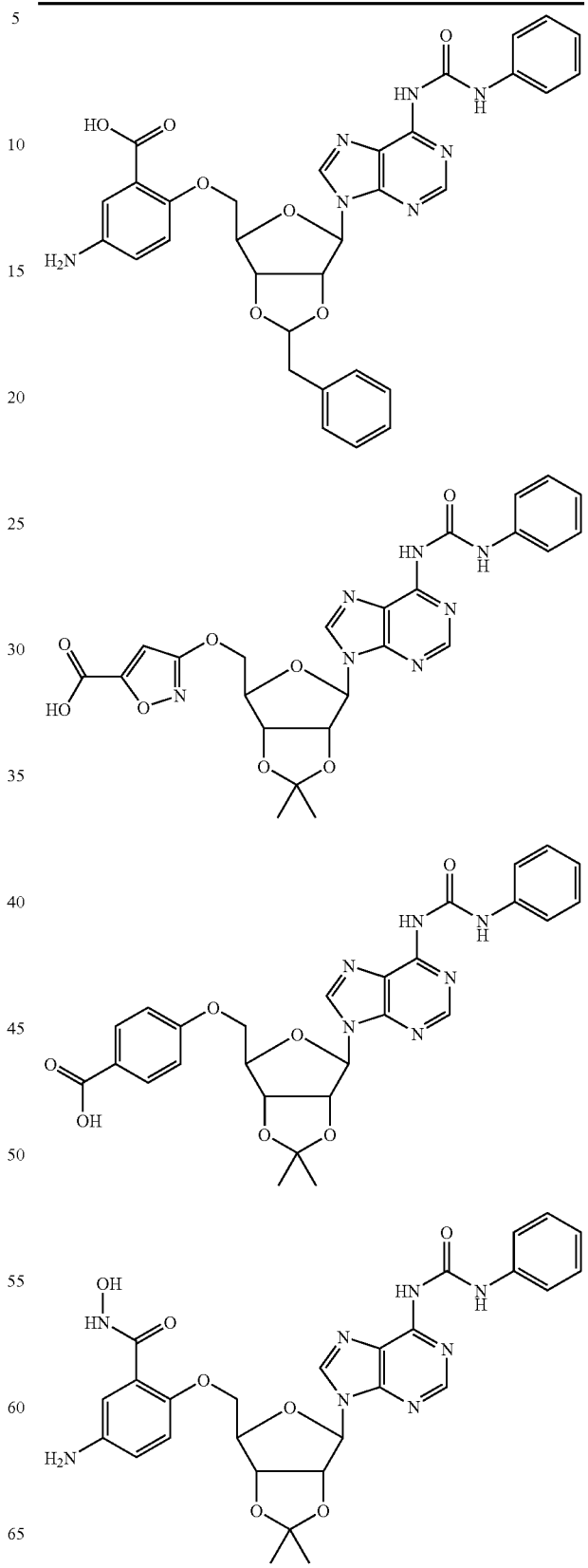

TABLE 1-continued
Exemplary Compounds.
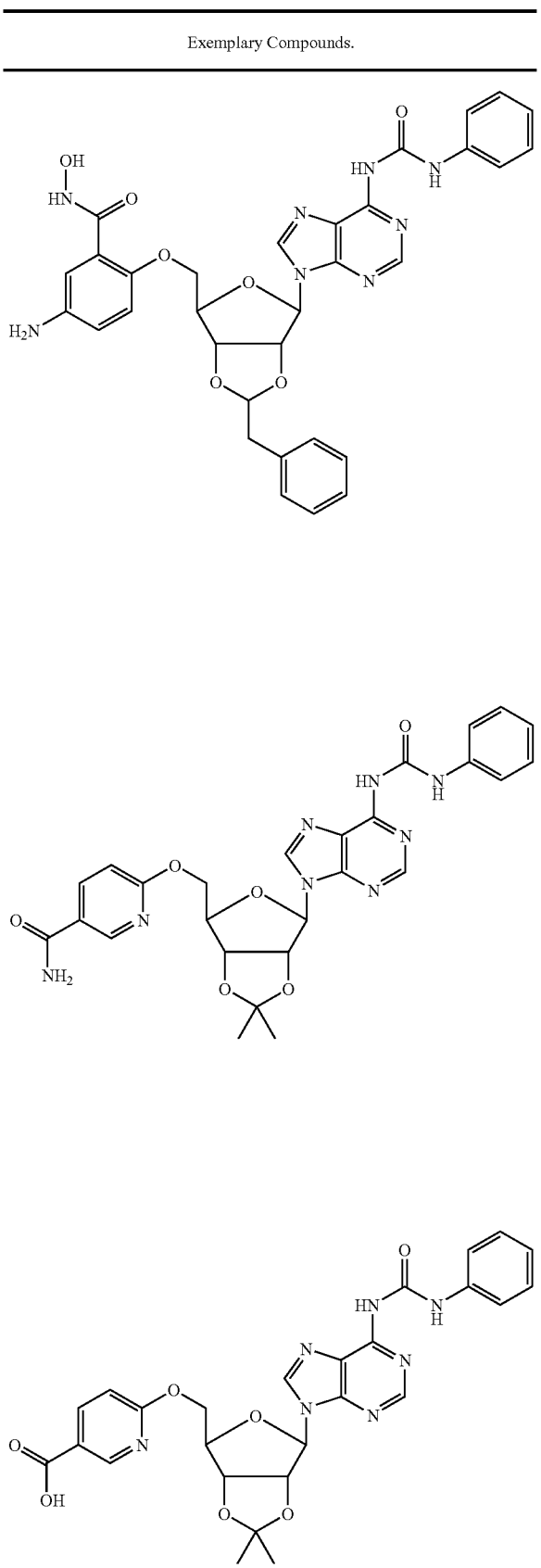
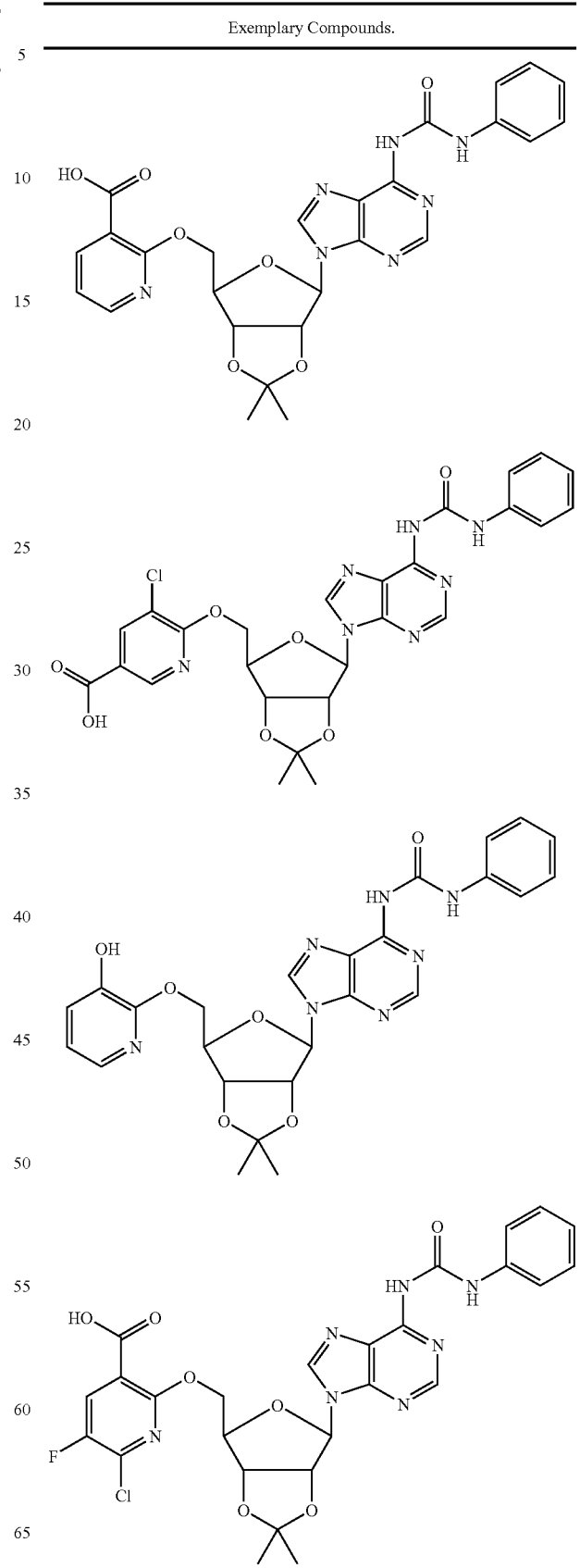

TABLE 1-continued
Exemplary Compounds.
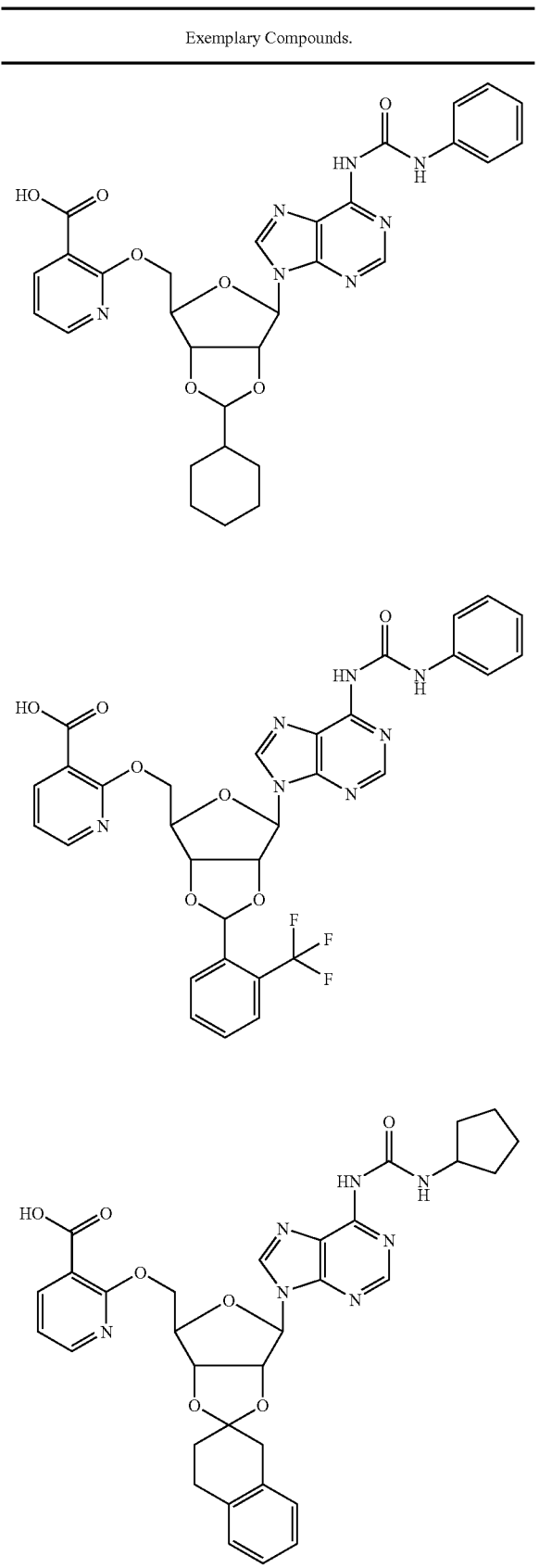
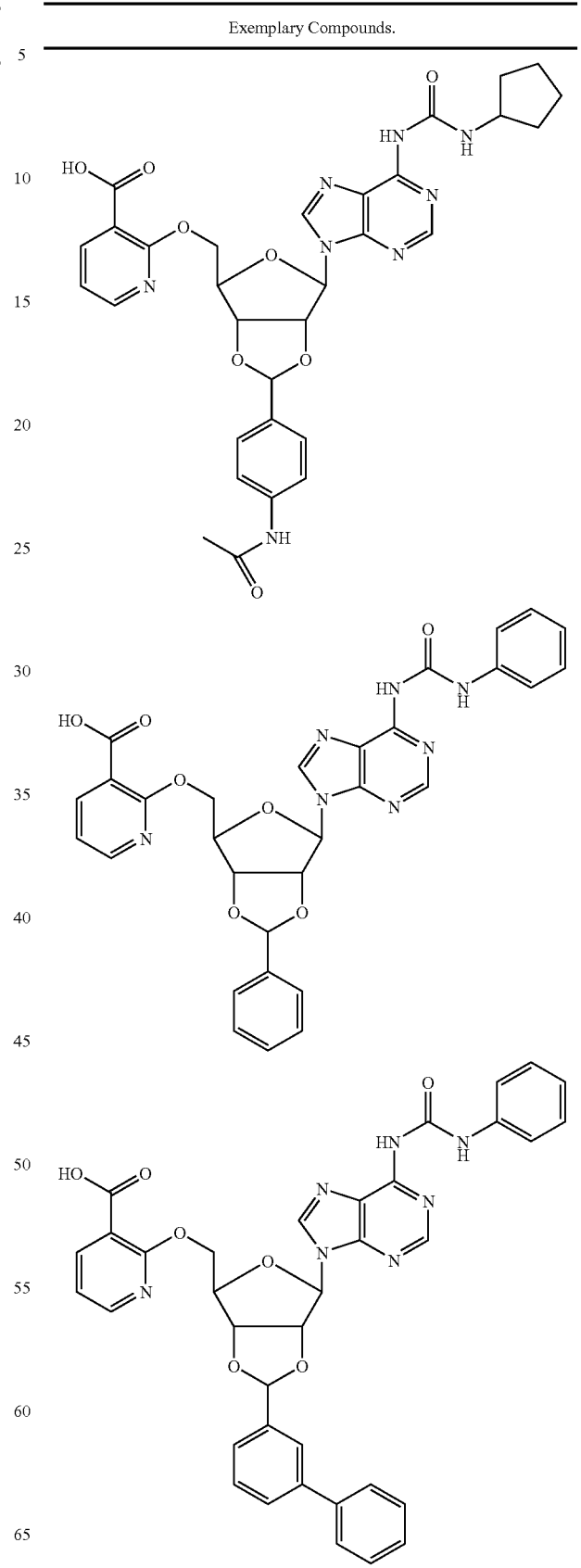

TABLE 1-continued
Exemplary Compounds.
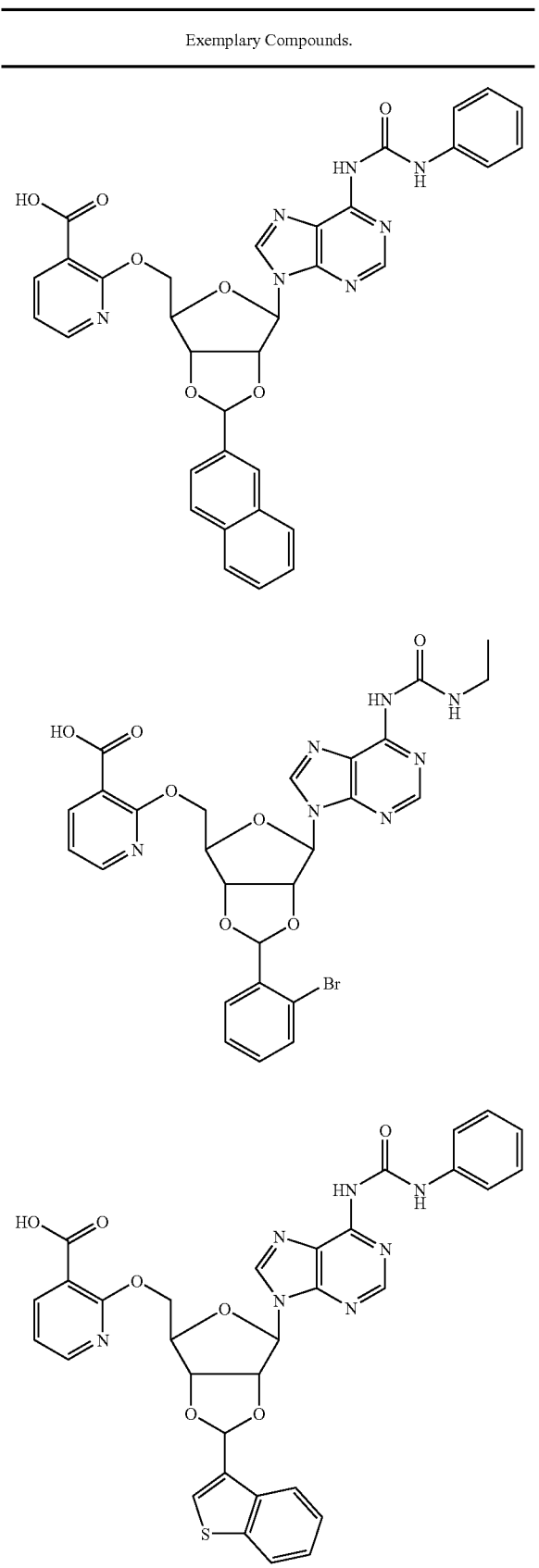
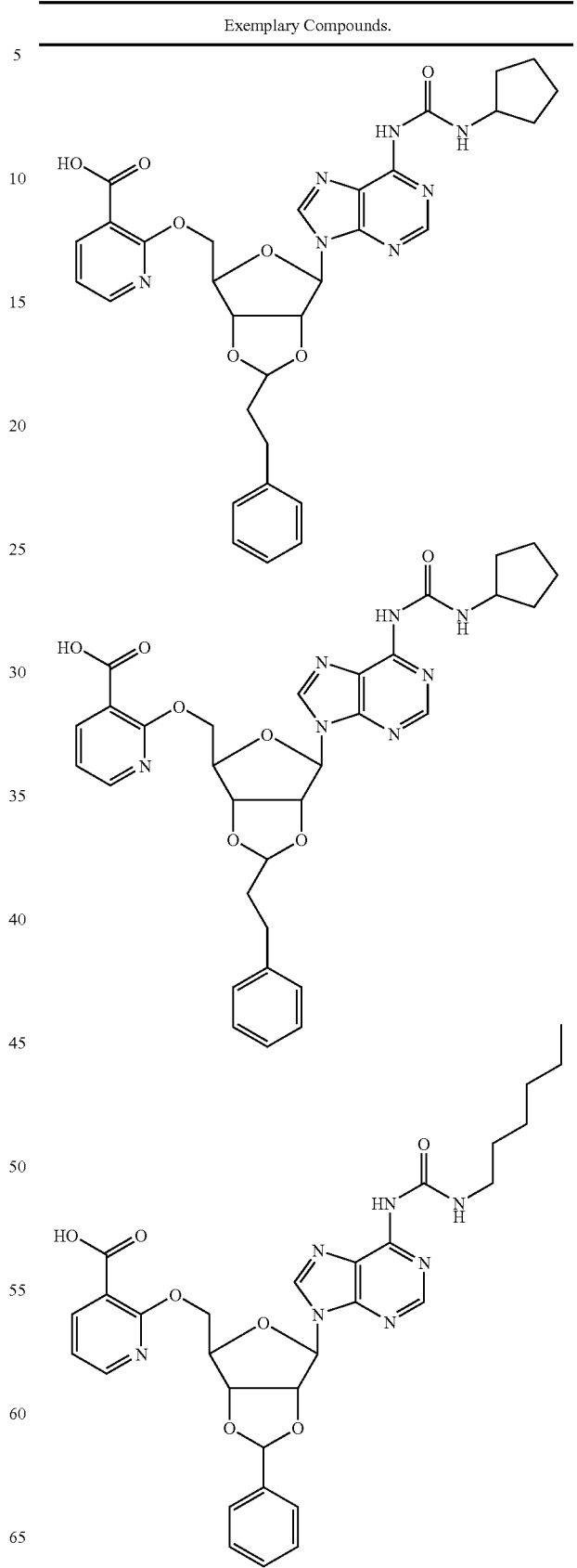

TABLE 1-continued
Exemplary Compounds.
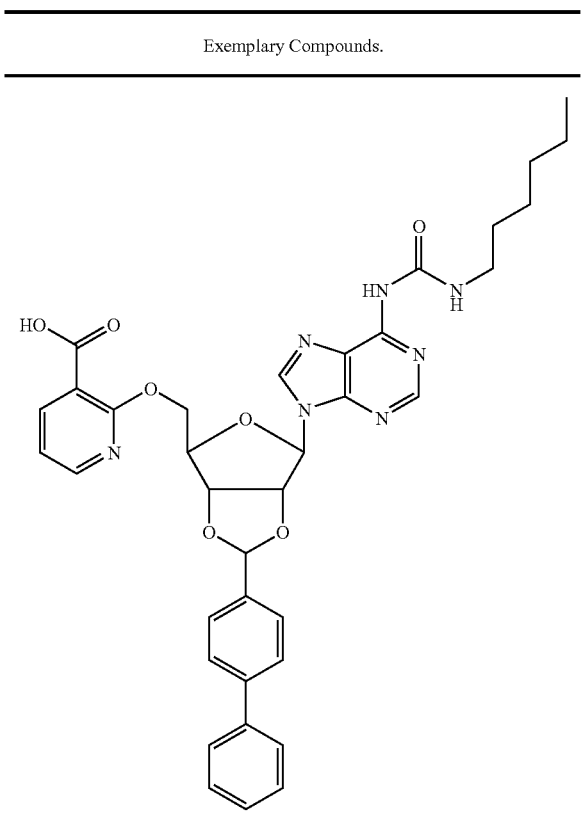
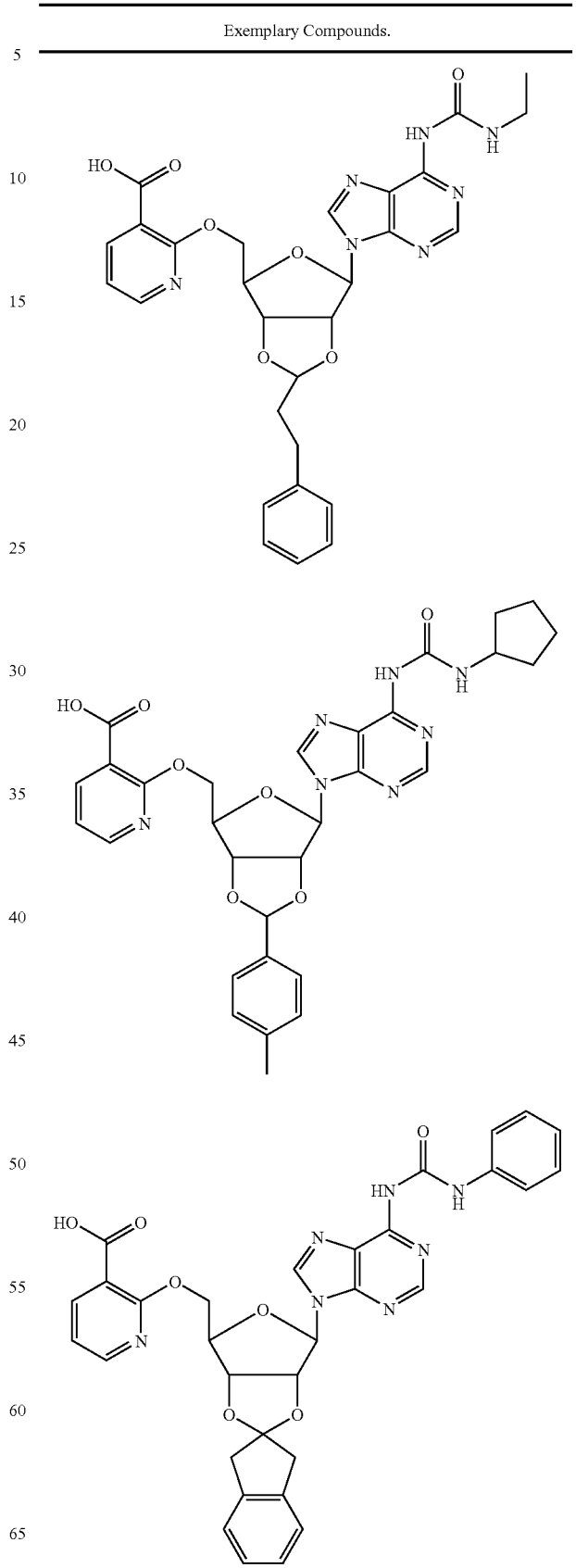

TABLE 1-continued
Exemplary Compounds.
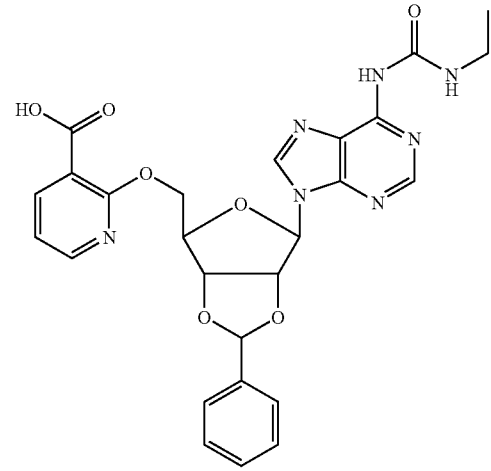
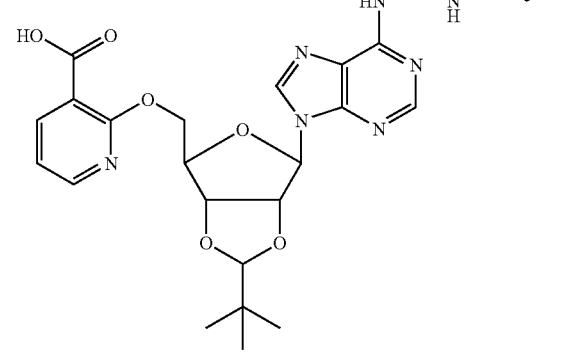
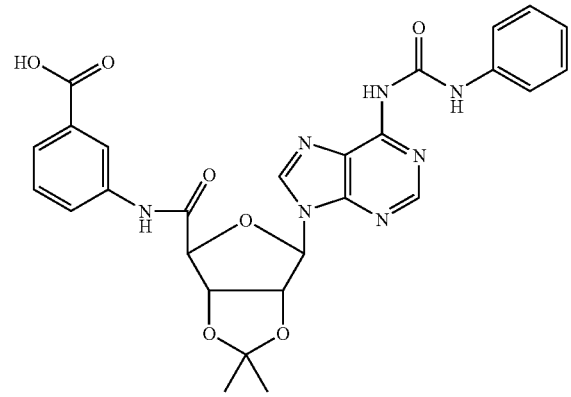
TABLE 1-continued
Exemplary Compounds.
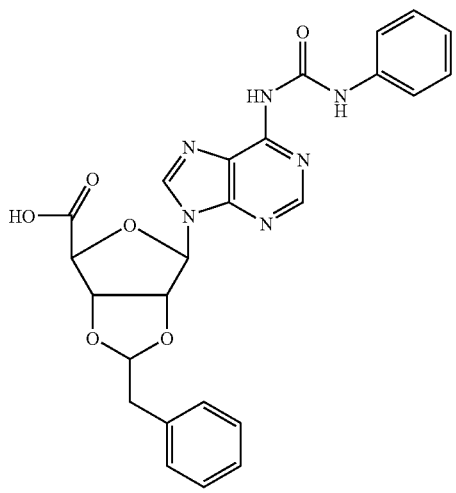
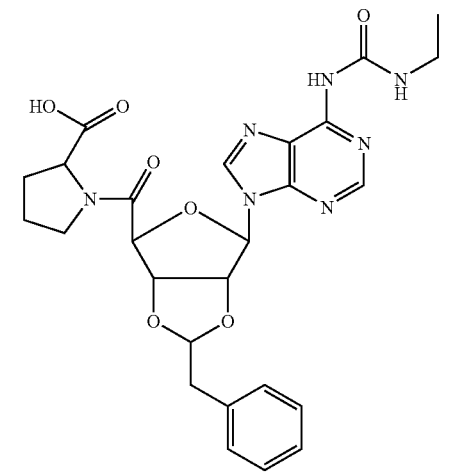
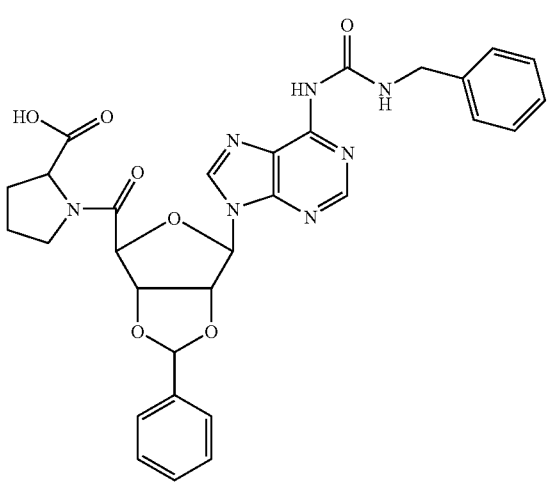

TABLE 1-continued
Exemplary Compounds.
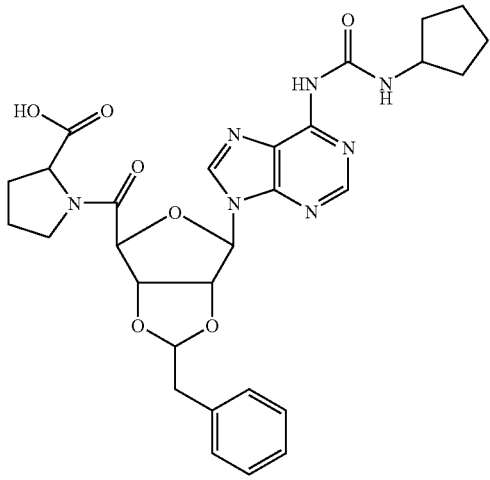
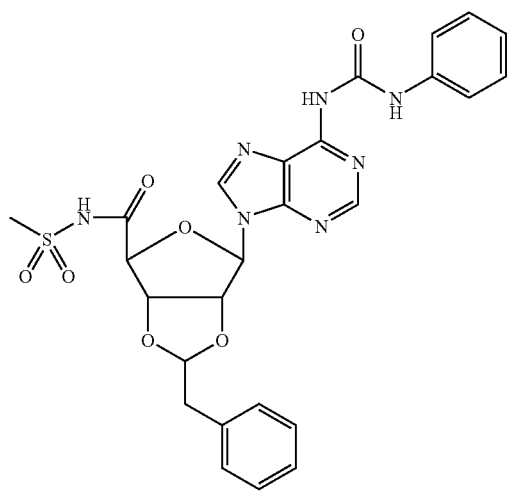
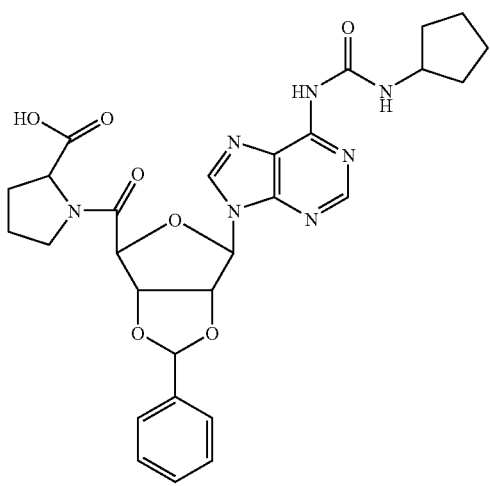
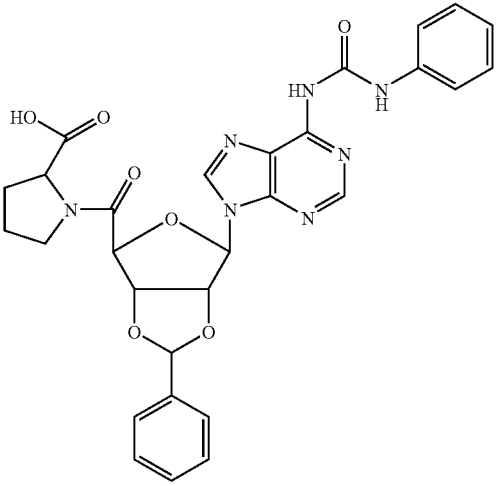
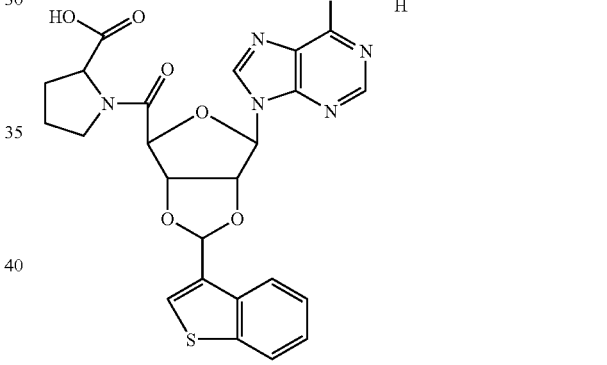
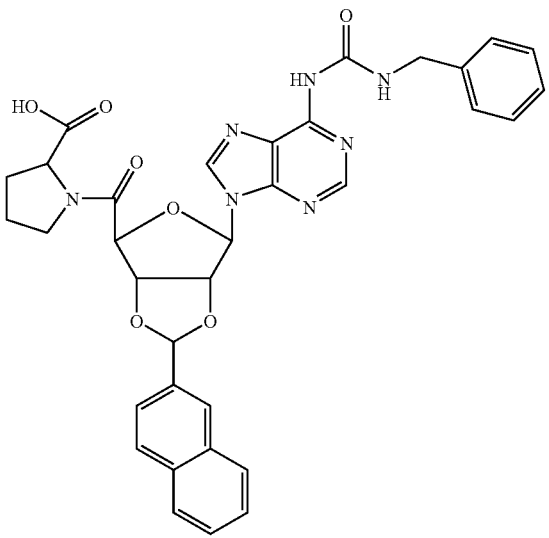

TABLE 1-continued
Exemplary Compounds.
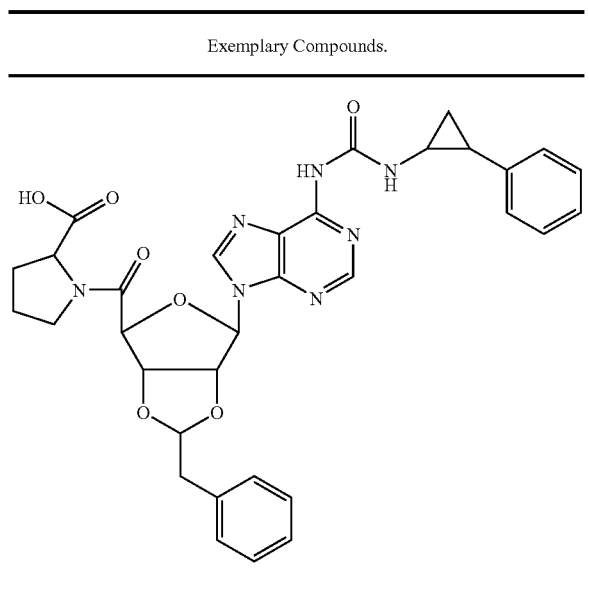
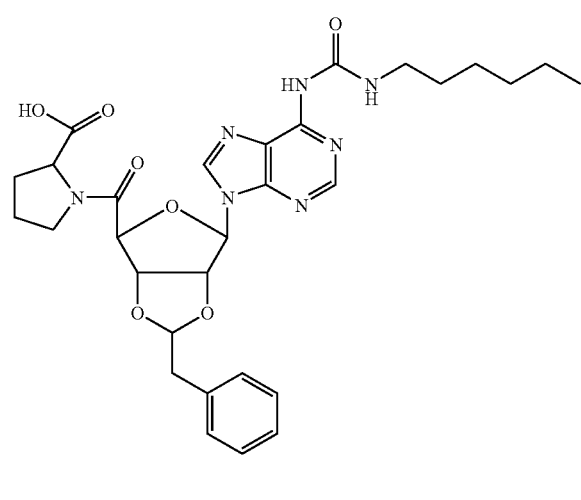
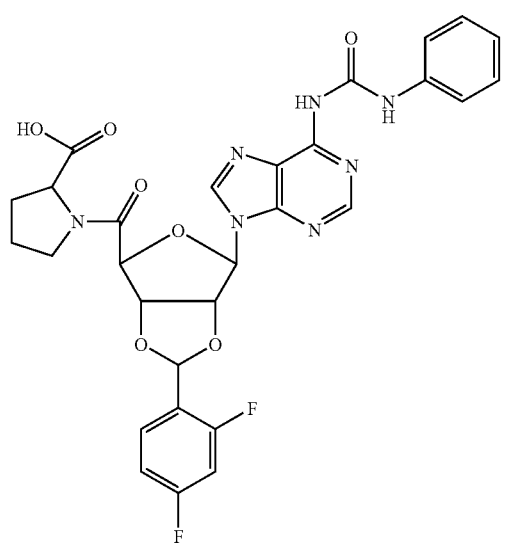
TABLE 1-continued
Exemplary Compounds.
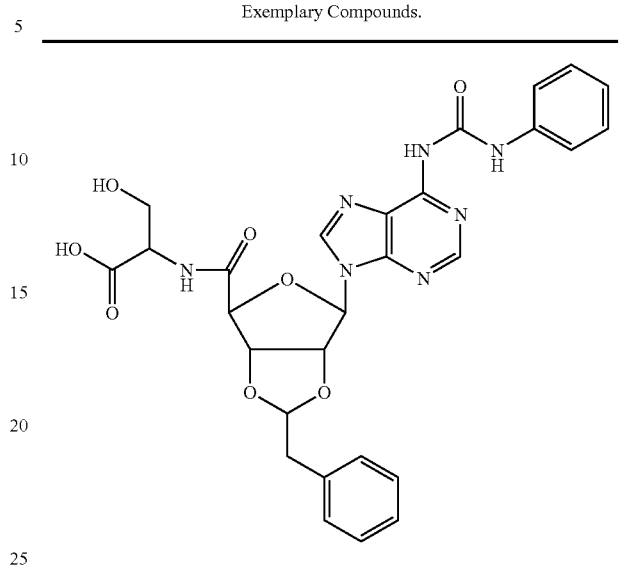
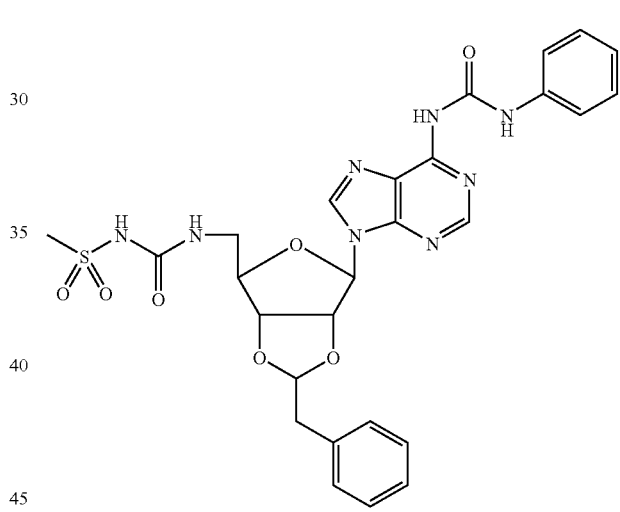
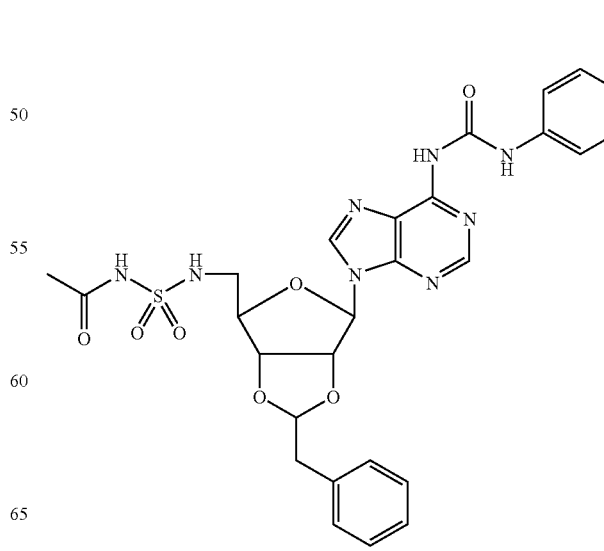

TABLE 1-continued
Exemplary Compounds.
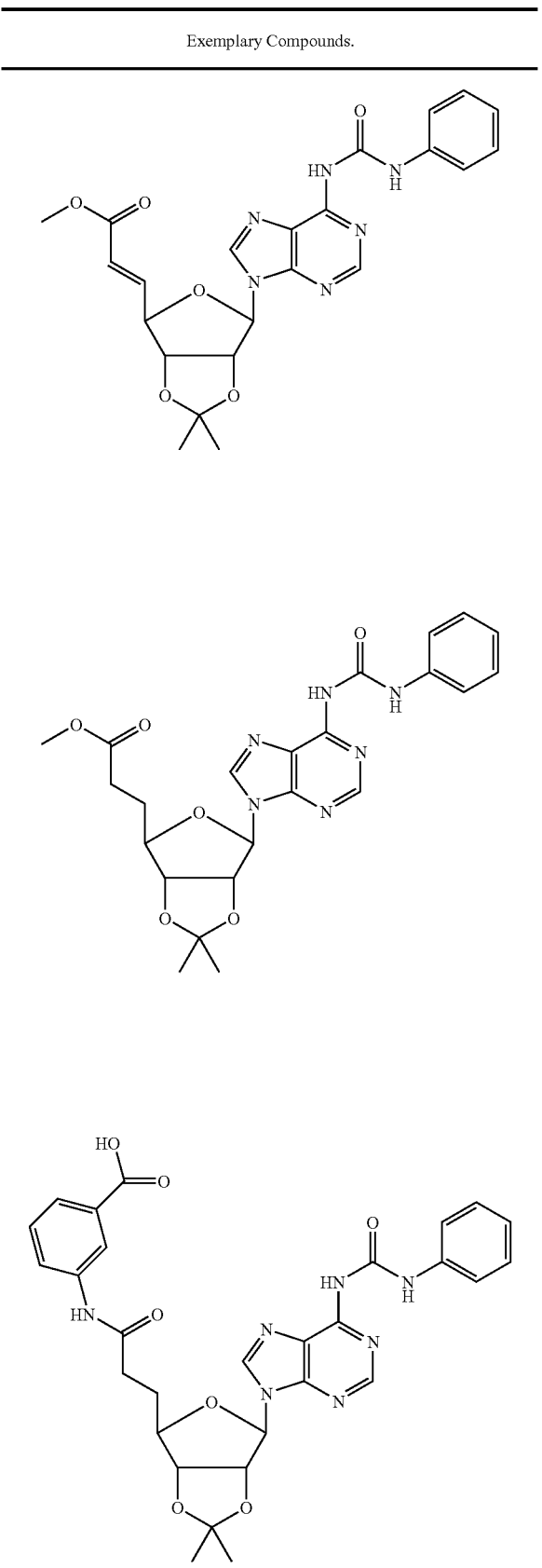
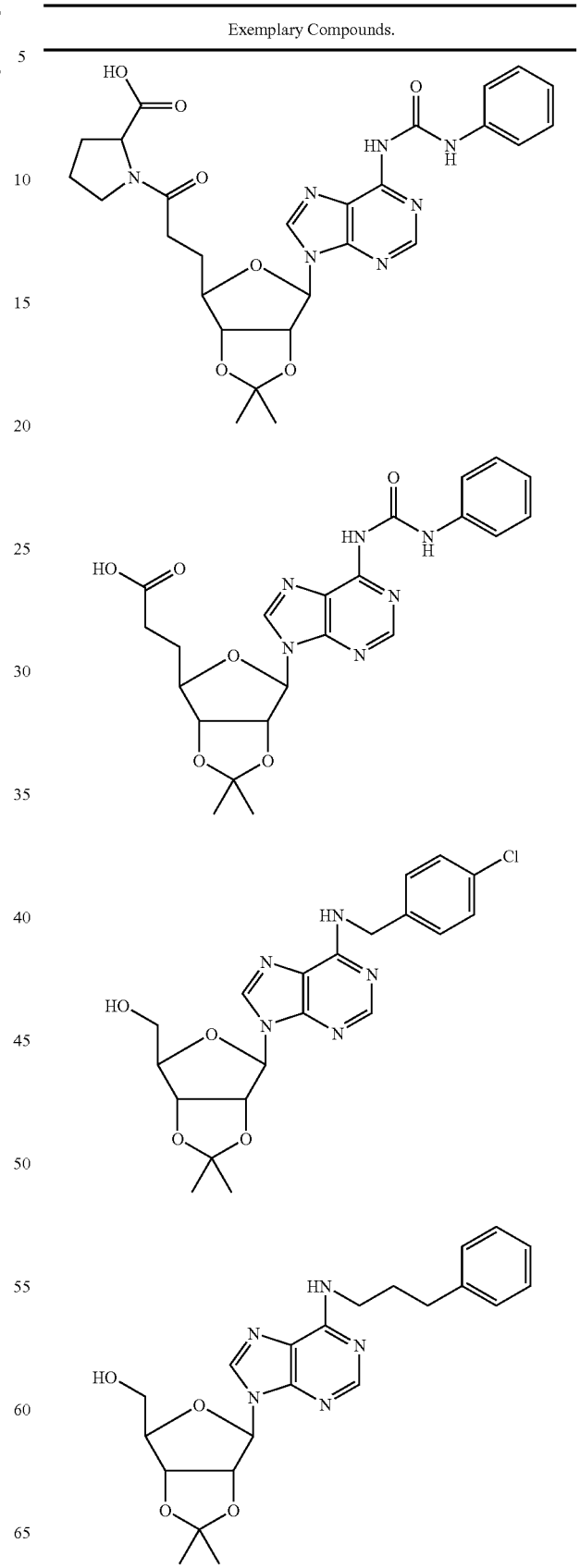

TABLE 1-continued

Exemplary Compounds.

TABLE 1-continued

Exemplary Compounds.

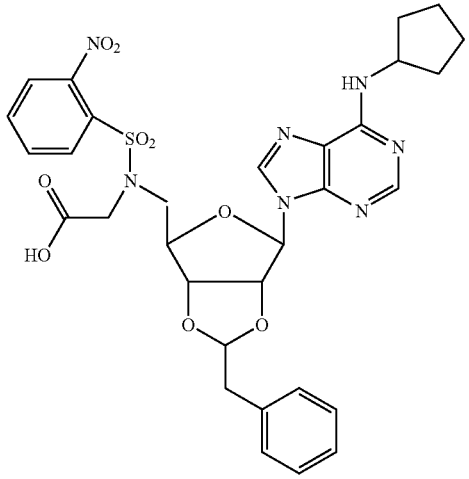

The present invention also encompasses non-toxic pharmaceutically acceptable salts of the above derivatives, such as, but not limited to, alkali metal salts such as lithium, sodium or potassium salts, or alkaline earth metal salts such as magnesium or calcium salts; or ammonium or mono-, di-, tri- or tetraalkyl ammonium salts, such as $NH_4^+$, $NEH_3^+$, $NE_2H_2^+$, $NE_3H^+$, or $NE_4^+$ (wherein E is $C_{1-4}$ alkyl) salts. Other salts such as hydrochlorides, hydrobromides, mesylates, sulfates, acetates, tartrates, etc., are also contemplated in this invention. Pharmaceutically acceptable salts are salts that retain a desired biological activity level similar to that of the parent compound but that do not impart undesired toxicological effects. Preferred counterions are monovalent ions such as $NH_4^+$, sodium, lithium, potassium, chloride, bromide, bisulfate, and mesylate, with sodium, potassium, chloride and mesylate being most preferred due to ease of manufacture, stability, and physiological tolerance.

Methods of Compound Preparation

The compounds of the present invention may be synthesized by those skilled in the art using conventional synthesis methodology and well-known workup and purification procedures. The following list of references, along with references cited therein, disclose general procedures employed for the synthesis of a number of intermediates and compounds related to the present invention: Baraldi, et al., *Journal of Medicinal Chemistry*, 39(3): 802-806 (1996); Camaioni, et al., *Bioorganic & Medicinal Chemistry*, 5(12): 2267-2275 (1997); Zablocki, et al., PCT International Publication No. WO01/40243; Zablocki, et al., PCT International Publication No. WO01/40246; Mantell, et al., PCT International Publication No. WO01/94368; Jacobson, et al., *Journal of Medicinal Chemistry*, 38(10): 1720-1735 (1995); Cristalli, et al., *Journal of Medicinal Chemistry*, 38(9): 1462-1472 (1995); Secrist, III and Talekar, *Nucleosides & Nucleotides*, 9(4): 619-27 (1990); Secrist, III, U.S. Pat. No. 4,794,174 (1988); Lyga and Secrist, III, *Journal of Organic Chemistry*, 48(12): 1982-1988 (1983); Dixon, et al., PCT International Publication No. WO02/096248; Hardern, et al., PCT International Publication No. WO01/36438; Guile et al., PCT International Publication No. WO00/04021; Lee, et al., *Bioorganic & Medicinal Chemistry Letters*, 13(6): 1087-1092 (2003); Cox, et. al., U.S. Pat. No. 5,747,496 (1998).

In many cases, commercially-available starting materials can be used for the synthesis of compounds of this invention. When not available commercially, useful starting materials can either be obtained from stepwise modification of commercially-available compounds and derivatives, or they may be synthesized from simpler precursors using literature methods known in the art. In addition, the compounds of the present invention may be synthesized using the general methods shown in Schemes 1-12, or variations thereof.

Comrnmercially-available materials comprise: adenosine, α-adenosine, 2', 3'-isopropylidineadenosine, 5'-acetyl-2', 3'-isopropylidineadenosine, $N^6$-(2-isopentenyl) adenosine, 2-chloroadenosine, 2-amino-6-chloropurine riboside, 6-chloropurine riboside, inosine, 8-bromoguanosine, 8-bromoadenosine, 8-azidoadenosine, 8-azaguanine, 8-azaadenine, protected ribonic acid lactone derivatives and protected furanose derivatives. Other appropriate intermediates can be purchased from commercial sources and used as starting materials for compounds of the present invention, or can be synthesized as described in the chemical literature.

As disclosed above, commercially available compounds, or their derivatives may be employed as starting materials for the methods of Schemes 1-12.

Scheme 1. Preparation of 5'-modified ethers by nucleophilic aromatic substitution.

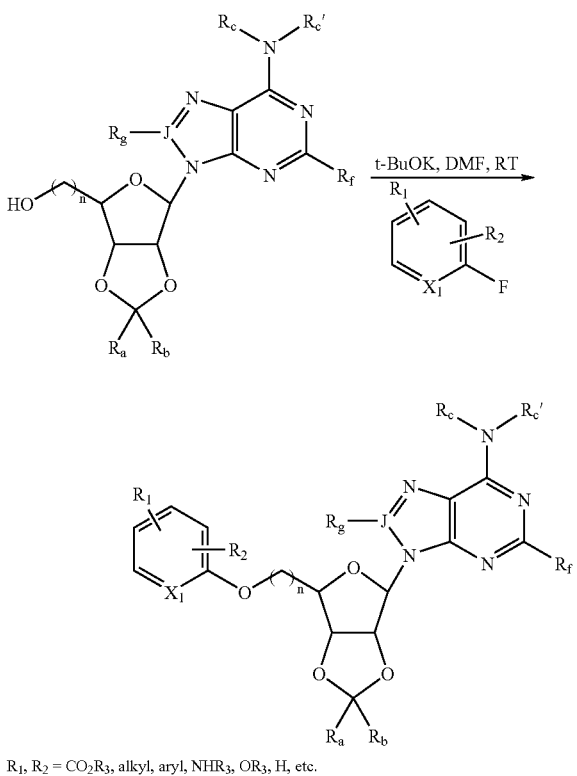

$R_1$, $R_2$ = $CO_2R_3$, alkyl, aryl, $NHR_3$, $OR_3$, H, etc.
$R_3$ = alkyl, aryl, etc; $X_1$ = $CR_1$, N; n = 1-6

Scheme 1, for example, discloses a useful method for the synthesis of 5'-aryl- or 5'-heteroaryl-nucleoside ethers and 8-azapurine-furanose 5'-ether derivatives by substitution of an appropriately functionalized adenosine analogue or 8-azapurine derivative for a halogen on an appropriately substituted halogenated aromatic compound or a related heteroaromatic derivative. Generic groups in Scheme 1 are as described in Formula I, which also includes the general definitions at the end of this section; some examples of preferred groups for $R_1$, $R_2$, and $R_3$ are provided, but these examples should not be considered limiting. For example, substituents at $R_1$ and $R_2$ of the aromatic/heteroaromatic-group in Scheme 1 can independently be hydrogen, or alkyl, or groups containing carboxylic acid derivatives such as: —$CO_2R_3$; but they can also be halogen, or esters or amides of alkylcarboxylic acids, arylcarboxylic acids, —O-(alkylcarboxylic acids), —NR-(alkylcarboxylic acids), and the like. When either or both of $R_1$ and $R_2$ are halogen in Scheme 1, preferred halogens are chloro and fluoro. It will be understood by those skilled in the art that, in some cases, the $N^6$-group will have to be temporarily protected using a group or groups such as benzyl, phthaloyl, etc., in order to allow the desired coupling in Scheme 1 to occur without competition by the $N^6$-group. Removal of said protecting group using methods known in the art then yields a compound of the present invention. In many cases, chemical intermediates produced using methods outlined in Schemes 1-12 may be useful in their own right as compounds useful for the practice of the methods of this invention.

5'-Substituted aryl nucleoside derivatives can also be prepared via Mitsunobu coupling (Mitsunobu, *Synthesis* 1-28 (1981); Brown, et al., *J. Med. Chem.* 37 (5), 674-88 (1994); Santosh and Balasubramanian, *Synthetic Communications*, 24(8), 1049-62 (1994)) of phenols to derivatives of adenosine, 8-azaadeonsine, guanosine, 8-azaguanosine, etc., as provided in Scheme 2. Generic groups in Scheme 2 are as described in Formula I, which also includes the general definitions at the end of this section; some examples of preferred groups for $R_1$, $R_2$, and $R_3$ are provided, but these examples should not be considered limiting. For example, substituents at $R_1$ and $R_2$ of the aromatic/heteroaromatic-group in Scheme 2 independently can be hydrogen, halogen, alkyl, alkoxy, aryl or groups containing carboxylic acids, and/or their derivatives such as: —$CO_2R_3$; but esters or amides of alkylcarboxylic acids, arylcarboxylic acids, —O-(alkylcarboxylic acids), —NR-(alkylcarboxylic acids), and the like are also included. When either or both of $R_1$ and $R_2$ are halogen in Scheme 2, preferred halogens are chloro and fluoro.

Scheme 2. Preparation of 5'-modified ethers by Mitsunobu coupling of phenols.

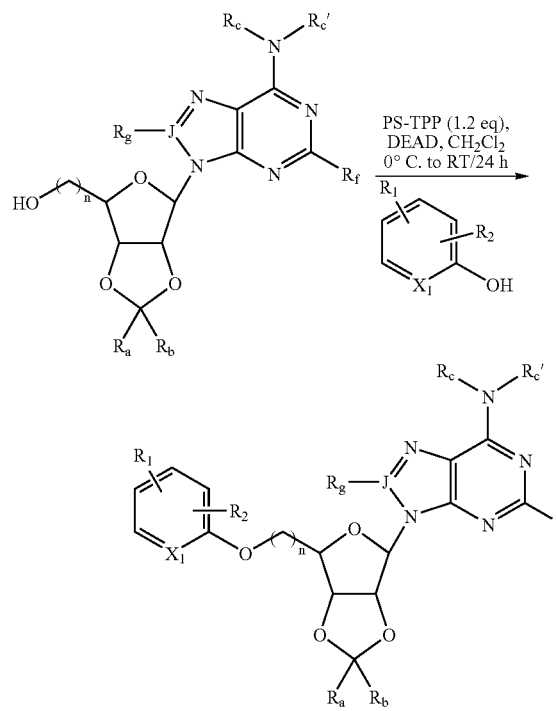

$R_1$, $R_2$ = $CO_2R_3$, alkyl, aryl, $NHR_3$, $OR_3$, H, halogen, etc.
$R_3$ = alkyl, aryl, etc; $X_1$ = $CR_1$; n = 1-6

Scheme 3. Preparation of 5'-modified isoxazole ethers by Mitsunobu coupling of isoxazole derivatives.

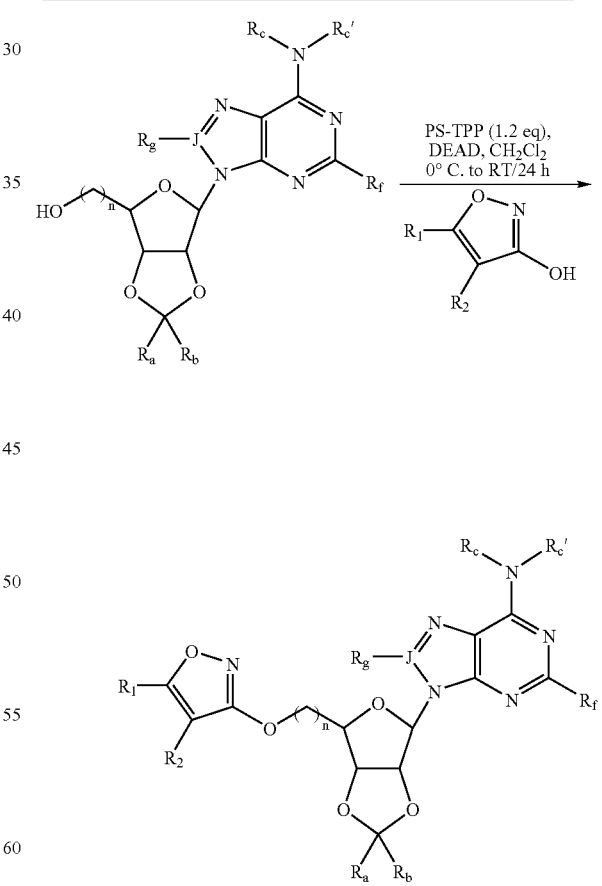

$R_1$, $R_2$ = $CO_2R_3$, alkyl, aryl, H, $NHR_3$, $OR_3$, halogen, etc.
$R_3$ = alkyl, aryl, etc; n = 1-6

Alternatively, the Mitsunobu coupling may be carried out using hydroxyisoxazoles and the appropriate derivatives of adenosine, 8-azaadenosine, guanosine, 8-azaguanosine, etc., as provided in Scheme 3. Generic groups in Scheme 3 are as described in Formula I, which also includes the general definitions at the end of this section; some examples of preferred groups for $R_1$, $R_2$, and $R_3$, are provided in the scheme, but these examples should not be considered limiting. For example, preferred substituents at $R_1$ and $R_2$ of the isoxazole derivatives of Scheme 3 independently are hydrogen, alkoxy, or halogen, or groups containing carboxylic acids or their derivatives such as: —$CO_2R_3$; but esters or amides of alkylcarboxylic acids, arylcarboxylic acids, —O-(alkylcarboxylic acids), —NR-(alkylcarboxylic acids), and the like, are also included. When either or both of $R_1$ and $R_2$ are halogen in Scheme 3, preferred halogens are chloro and fluoro.

When the products of any of Schemes 1, 2 or 3 comprise esters, said esters themselves can be useful in the invention. Said ester derivatives may be purified by methodologies well-known in the art, such as by normal phase, or reverse phase chromatography, or in suitable circumstances, using crystallization techniques. Alternatively, said ester derivatives can be used in the synthesis of other derivatives such as amides, hydroxamic acids, and different alkyl esters by well-known methods in the art.

Optionally, said esters may be hydrolysed under basic conditions, or cleaved using other methods known in the art, which cleave esters selectively in the presence of ketals or acetals to provide acid salts. These salts are also useful in the invention.

If desired, said acid salts can be converted into acids upon mild acid treatment. Workup by common techniques and purification by methods well known in the art, including purification by crystallization or chromatography, can be used to give the purified acids. Said acids can also be converted into other useful derivatives such as amides, hydroxamic acids, aryl esters, etc., by methods known to those skilled in the art of chemical synthesis. These acid derivatives are also useful in the invention, and are also purified using well-known methods such as crystallization or chromatography.

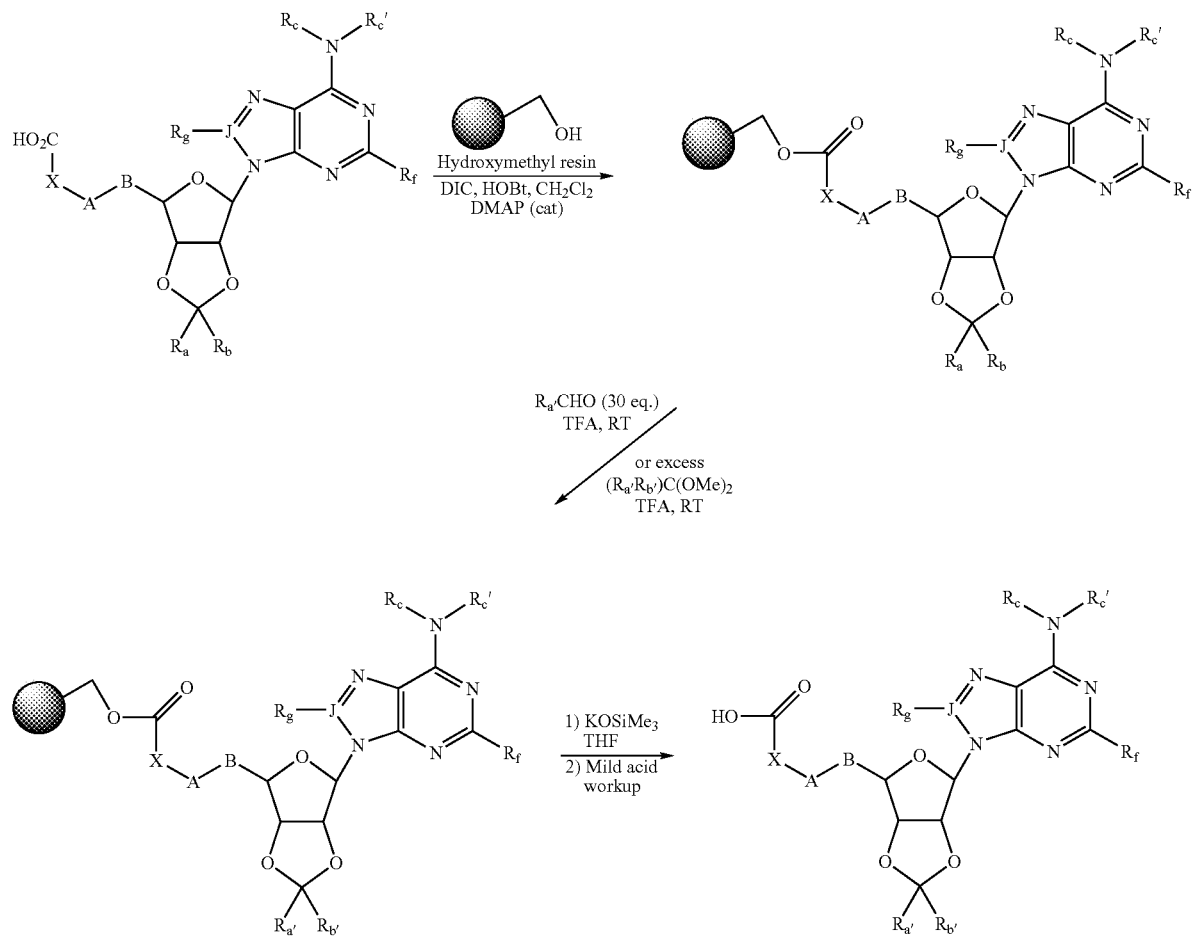

Scheme 4. Transformation of 2′,3′-acetals and -ketals into new acetal and ketal derivatives using solid phase techniques.

Where $R_{a'}$ and $R_{b'}$ denote different $R_a$ and/or $R_b$

Diversity using common intermediates can be introduced into the 2', 3'-acetal or -ketal position of compounds encompassed in Formula I, as well as at the $N^6$-position of compounds of Formula I using solid-phase synthetic methods. Schemes 4 and 5 exemplify transketalization procedures using polymer-bound relatives of compounds of Formula I. These methods can be used to transform one class of 2', 3'-ketal or -acetal into other useful 2', 3'-acetal or -ketal derivatives of adenosine, guanosine, 8-azaadenosine, etc. These polymer-bound approaches are very useful for after the desired reaction is complete, excess reagents can be washed away using one to several solvent washes. The desired material remains attached to the resin, in a pre-purified form, until it is cleaved from the solid phase using the appropriate conditions. Final purification of the desired product is then accomplished by conventional techniques like chromatography or crystallization.

phase approaches are similar to methods known and used for solution-phase chemical transformations involving the synthesis of adenosine, guanosine, 8-azaadenosine, etc., derivatives. The primary differences are the necessity of attachment of a starting material to a resin, the simplicity of resin-based purification techniques (filtration and washing by compatible solvents) compared to solution-phase purification techniques (chromatography crystallization, etc.), and the requirement for cleavage of a compound of the invention, or an intermediate useful for the synthesis of a compound of the invention, from a resin prior to final purification and/or use of a compound so cleaved.

In Scheme 5, an early intermediate, such as a 6-chloroadenosine-2', 3'-ketal or -acetal derivative, or a 6-chloro-8-azaadenosine-2', 3'-ketal or -acetal derivative is attached to a resin such as polystyrene resin via a β-thioethanol linker (e.g., hydroxyethylsulfanylmethyl polystyrene; HESM polysty- Scheme 5. Transformation of 6-chloro derivatives into 6-amino, 6-amido, 6-carbamoyl, 6-ureido, 6-thioureido, 6-guanidino, etc., derivatives and subsequent conversion of 2',3'-acetals and -ketals into new acetal and ketal derivatives using solid phase techniques.

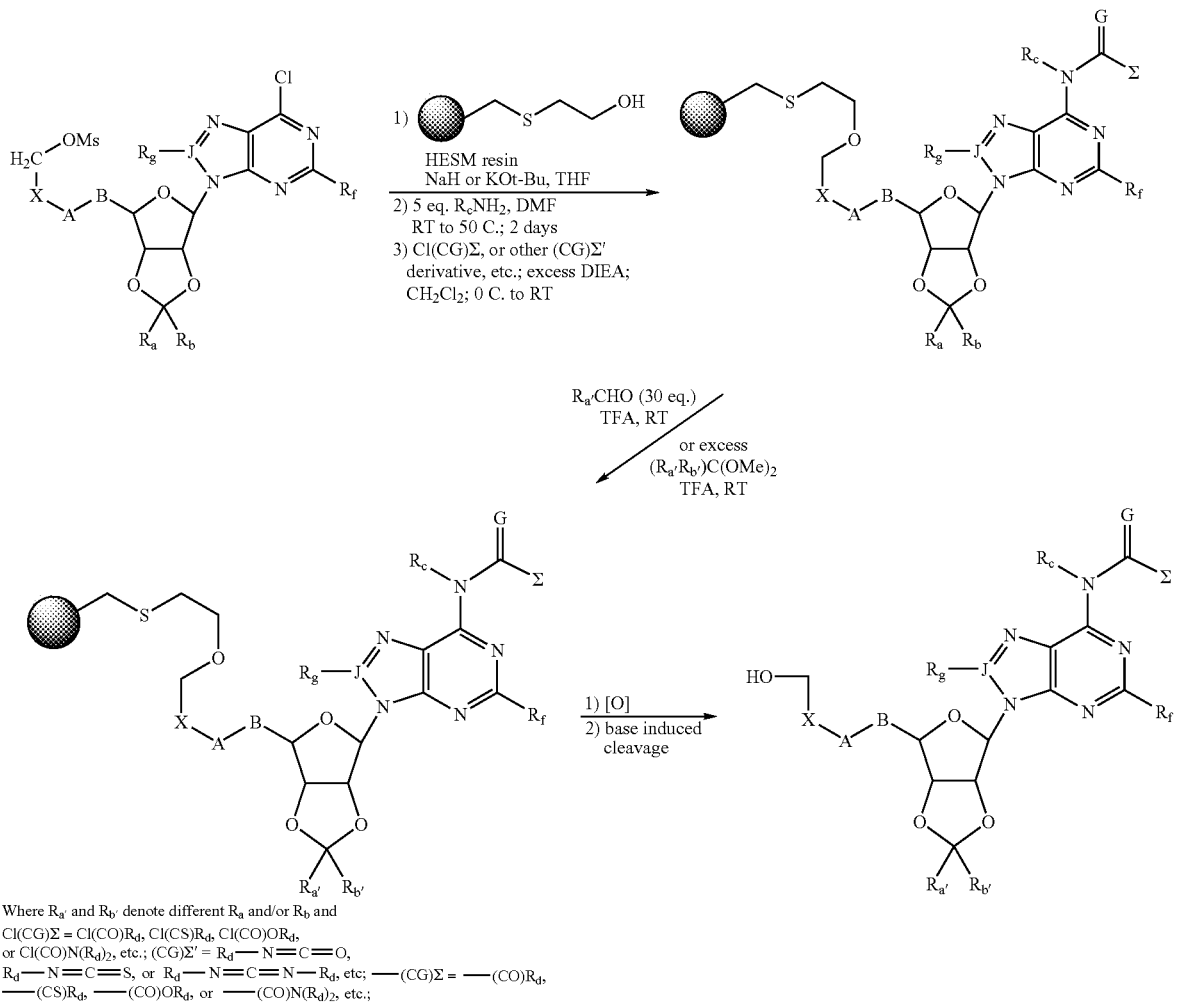

Where $R_{a'}$ and $R_{b'}$ denote different $R_a$ and/or $R_b$ and
Cl(CG)Σ = Cl(CO)$R_d$, Cl(CS)$R_d$, Cl(CO)O$R_d$,
or Cl(CO)N($R_d$)$_2$, etc.; (CG)Σ' = $R_d$—N═C═O,
$R_d$—N═C═S, or $R_d$—N═C═N—$R_d$, etc; ——(CG)Σ = ——(CO)$R_d$,
——(CS)$R_d$, ——(CO)O$R_d$, or ——(CO)N($R_d$)$_2$, etc.;

Scheme 5 shows another variation of compound preparation employing resin-bound materials of Formula I. It outlines a sequence of solid-phase procedures that are useful for the introduction of functionality at the 6-position, as well as for transketalization at the 2', 3'-position, if desired. It should be noted that the chemistry procedures used in these solid rene resin; Garcia-Echeverria, *Tetrahedron Lett.*, 38, 8933-7 (1997)). After workup by filtration and rinsing with a useful solvent like DMF, the resin bound material is treated with a primary or secondary amine, ammonia or a hydroxylamine derivative to introduce an amino group via displacement of the 6-chloride. Scheme 5 exemplifies the process using a generic primary amine, $R_cNH_2$. Though not shown in Scheme 5, a resin-bound product from chloride displacement by $R_cNH_2$ can be cleaved from the solid-phase after formation and workup without conversion into an amide or other derivative; such an amine product, in itself, can be useful for this invention. Or, the said resin-bound $C^6$-amine product, itself, can be used in the transketalization/transacetalization step shown in Scheme 5 without prior transformation into a —(CG)Σ derivative, or a —(CG)Σ' derivative, to give a different 2', 3'-acetal-6-amine derivative tethered to the solid phase. When cleaved from the solid phase, such a $C^6$-amine material can also be useful in the method of the invention. If desired, such a $C^6$-amine material can be further converted into one or more other $N^6$-derivatives as shown. It should be noted that treatment of a 6-chloro derivative, such as shown in Scheme 5, with secondary amines, such as $(R_c)_2NH$ or $R_cR_c'NH$, can also yield products useful in this invention. For example, an embodiment of this invention comprises compounds that have a $C^6$-piperazino-group; a preferred embodiment of this class of compounds comprises a substituted piperazino-group on $C^6$. A particularly useful class of derivatives comprises an aryl substituent on the distal amine of said piperazino group. Alternatively, if a $(R_c)$-group is used as a temporary protecting group, such as for the selective introduction of a $N^6$-group or for protection during a later step, said $(R_c)$-group can be removed after it has served its purpose in a desired chemical step or steps to yield a compound useful in the invention, or a compound useful for conversion into a such a compound of the invention.

As with solution phase techniques, subsequent introduction of an amido-, thioamido-, carbamoyl-, ureido-, thioureido-, or guanidino-group at $N^6$ of a polymer-bound amine intermediate such as provided for in Scheme 5 can be made in one step using an excess of an appropriate acid/coupling agent combination in an appropriate solvent (e.g., methoxypropionic acid/dicyclohexylcarbodiimide/dichloromethane), or using other conditions known in the art, such as those involving an acid chloride, acid anhydride, carbonyl chloride, chloroformate, isocyanate, isothiocyanate, carbodiimide, carbamoyl chloride, or 2-alkyl-2-thiopseudourea; or using a chemical equivalent of such materials using well-known methods in the art, or using other methods and reagents in the literature.

Alternatively, a two-step approach can be used to introduce a group at $N^6$, which comprises treatment of an appropriate 6-amino derivative, synthesized as in Scheme 5, with a solution of a small excess of phosgene or thiophosgene and a tertiary amine such as DIEA in a suitable solvent such as dichloromethane or toluene at a temperature which allows reaction, followed by treatment with an excess of a nucleophile, such as a primary or secondary amine to give a resin-bound urea or thiourea after workup. Other useful nucleophiles for this reaction are alcohols, phenols, hydrazine derivatives, etc. If desired, transketalization can be performed on a bound substrate of Scheme 5 in a manner similar to that shown in Scheme 4. Or, if a desired acetal or ketal moiety of a 6-chloroadenosine, 6-chloroguanosine, 6-chloro-8-azaadenosine, etc., derivative is used to begin with, then no transketalization is necessary. Cleavage from the β-thioethanol linker of the solid phase, as shown for the HESM polystyrene resin in Scheme 5 is performed in two steps: oxidation of the thioether-linker using an oxidizing agent like MCPBA in a solvent such as dichloromethane gives a sulfone-linker, then cleavage of the β-ether moiety from the oxidized linker occurs upon treatment with a strong base like DBU in a solvent like dichloromethane and yields a compound which can be purified by techniques known in the art. Preferred oxidizing agents include peracids like MCPBA and peracetic acid, but other oxidizing agents like hydrogen peroxide, permanganate salts, or persulfate salts can be used to oxidize a thioether to a sulfone. Preferred elimination conditions include DBU in dichloromethane, or 10% ammonium hydroxide in trifluoroethanol.

Following cleavage from the solid phase, a compound formed using the procedures in Scheme 5 can be used in the present invention, or can be further modified by well-known methods for functional-group transformations to generate new compounds which are also useful for this invention.

Preferred aldehydes, aldehyde acetals and ketone ketals useful in the transketalization methods shown in Schemes 4 and 5 comprise the below said carbonyl compounds and/or derivatives of: benzaldehyde, biphenyl-3-carboxaldehyde, biphenyl-4-carboxaldehyde, biphenyl-4-yl-acetaldehyde, 2-bromobenzaldehyde, benzo[b]thiophene-3-carbaldehyde, cyclohexanecarbaldehyde, cyclopentanecarbaldehyde, 2,5-dimethylbenzaldehyde, 2,6-difluorobenzaldehyde, 2-fluorobenzaldehyde, naphthalene-2-carbaldehyde, phenyl acetaldehyde, phenyl propynal, 3-phenyl propenal, 3-phenyl propionaldehyde, 2-trifluoromethyl benzaldehyde, cyclohexanone, cyclopentanone, 4-ethyl cyclohexanone, 3,4-dihydro-1H-naphthalen-2-one, indan-2-one, and propan-2-one. Useful derivatives for transketalization of the above ketones comprise ketals like dimethoxy- or diethoxy-ketals, etc.

In addition to the introduction of amines on the $C^6$ position using solid phase techniques as provided in Scheme 5, diversity can also be introduced at the 6-position of an adenosine, 8-azaadenosine, guanosine, etc., analog via the intermediacy of a 6-halogenated-purine derivative using solution phase methods. Scheme 6 exemplifies the preparation of 5'-isoxazole ethers, and shows the introduction of a nucleophile such as ammonia, an amine or a hydroxylamine derivative at the 6-position of the purine/8-azapurine ring by displacement of a chloride leaving group (a 6-chloride is shown in Schemes 5 and 6, but the leaving group at $C^6$ could also be another type, useful for such a transformation, e.g., a 6-bromide or 6-mesylate moiety) by such materials. Though Scheme 6 is exemplified using the generic primary amine $R_cNH_2$, a secondary amine such as disclosed for Scheme 5 could also be employed, if desired, to give a N,N-disubstituted-$N^6$-amine as a final product. $N^6$-Substituted, and $N^6,N^6$-disubstituted amines are useful for the invention, as are $N^6$-unsubstituted amines. Amines and amine-like compounds useful for displacement of a $C^6$-halogen or another type of leaving group at $C^6$-, as contemplated for these schemes comprise ammonia, methylamine, dimethylamine, and other N-alkyl- and N,N-dialkyl amines; N-aralkylamines; N-cyclopropylamine and other N-cycloalkylamines; anilines; N-aryl-N-alkyl amines; ethers and other O-derivatives of hydroxylamine; aminopyridines and other heteroaromatic amines; heterocyclic compounds having a pendant —$NR_H$ group; heterocyclic amines, and alkyl amines which have one or more heteroatom units like O, NR, and/or S substituted for carbon units in the alkyl chain. Such $N^6$-products are useful in this invention. But, if desired, $N^6$-products formed from said $C^6$-halogen/leaving group displacements can be further transformed into amides, thioamides, ureas, thioureas, carbamates, guanidines, etc., by literature methods or by methods disclosed for such transformations in Scheme 5 and/or Scheme 6 to give other derivatives useful in this invention. Following cleavage from the solid phase (for Scheme 5), the materials of Schemes 5 and/or Scheme 6 can be purified by methods typically used in the literature, such as by chromatography or, in certain cases, by crystallization. Preferred substituents at $N^6$ are H, alkyl-groups, aryl-groups, amides, carbamates, and ureas.

Scheme 6. Solution phase synthesis of 5'-heteroaromatic ether-$N^6$-derivatives by Mitsunobu reaction, 6-chloride displacement, and if desired) $N^6$-amine derivatization.

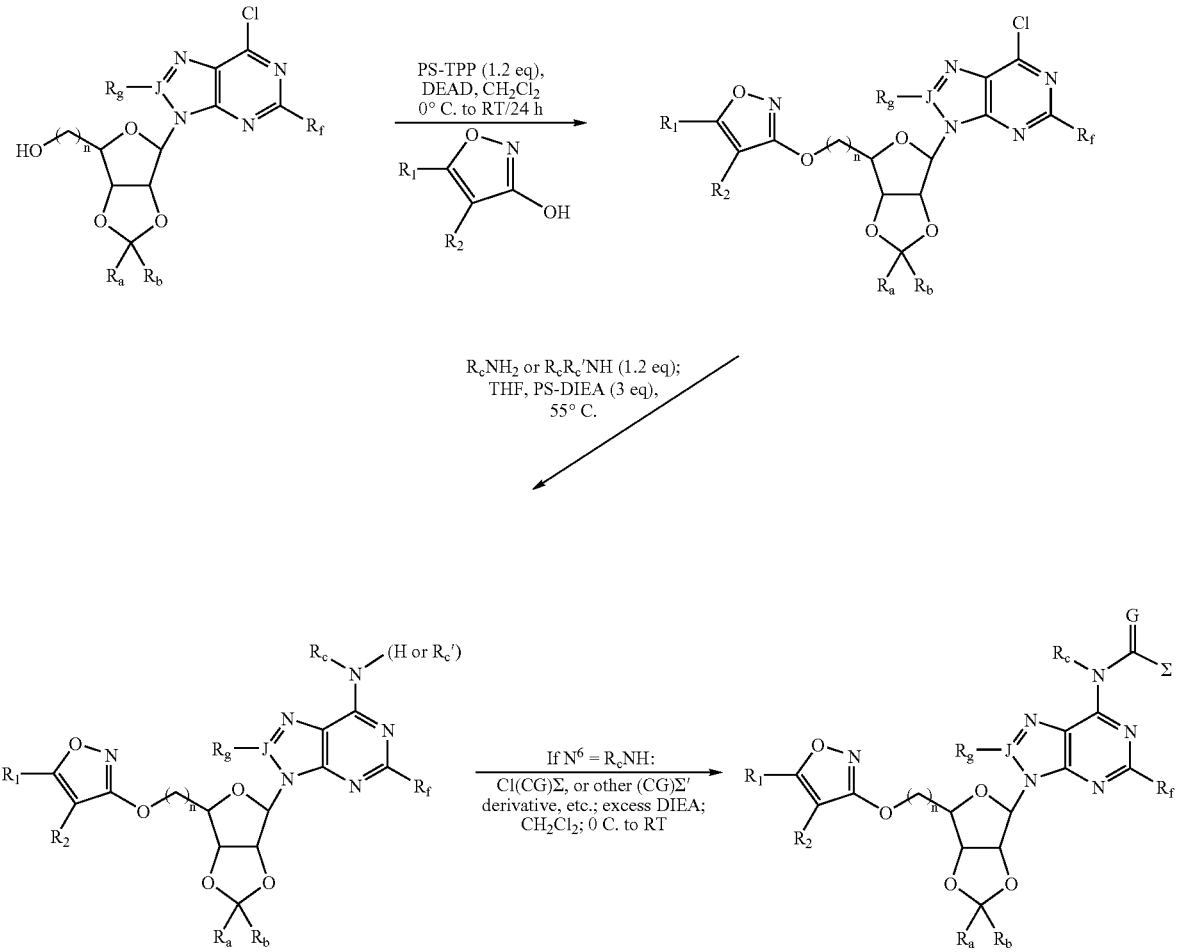

$R_1$, $R_2$ = $CO_2R_3$, alkyl, aryl, H, halogen, etc.
$R_3$ = alkyl, aryl etc; n = 1-6;
Cl(CG)Σ = Cl(CO)$R_d$, Cl(CS)$R_d$, Cl(CO)O$R_d$,
or Cl(CO)N($R_d$)$_2$, etc.; (CG)Σ' = $R_d$—N═C═O,
$R_d$—N═C═S, or $R_d$—N═C═N—$R_d$, etc;
——(CG)Σ = ——(CO)$R_d$, ——(CO)O$R_d$, or ——(CO)N($R_d$)$_2$, etc.

When $R_1$ and/or $R_2$ of an isoxazole derivative as provided in Scheme 6 contains an ester group (e.g., —C(CO)O-(alkyl), —C(CO)O-(aryl), —(CH$_2$)$_m$C(CO)O-(alkyl), —O(CH$_2$)$_m$C(CO)O-(aryl), etc., where "m" defines the chain length of such a compound of Formula I), said ester can be used in the present invention, or it may be converted into an acid using a method which is compatible with an acetal or ketal moiety and a desired group at $N^6$. For example, an ester provided in Scheme 6 can be hydrolyzed at room temperature (RT) in several hours using an excess of aqueous 2M lithium hydroxide solution dissolved in dioxane and/or methanol to give a carboxylate salt. Purification of said salt or a corresponding acid of said salt can be accomplished as previously disclosed. These acids and acid derivatives are also useful in this invention. Scheme 6 is exemplified using both a generic primary amine (which includes ammonia and hydroxylamine derivatives), and a generic secondary amine (including hydroxylamine derivatives) as choices for nucleophiles in the displacement of a leaving group (like chloride) at $C^6$. As in Scheme 5, the synthesis of a $C^6$-primary, secondary, or tertiary amine is possible using such a displacement reaction as shown in Scheme 6; such compounds are useful in this invention. Further modification of the $N^6$-group of a compound of Scheme 6 with a —(CG)Σ group or a —(CG)Σ' group also yields a compound of the invention.

Scheme 7. Synthesis of 2', 3'-O-Isopropylideneadenosine-5'-carboxylic acid, related acetals and ketals, and their use as intermediates for the synthesis of compounds of this invention.

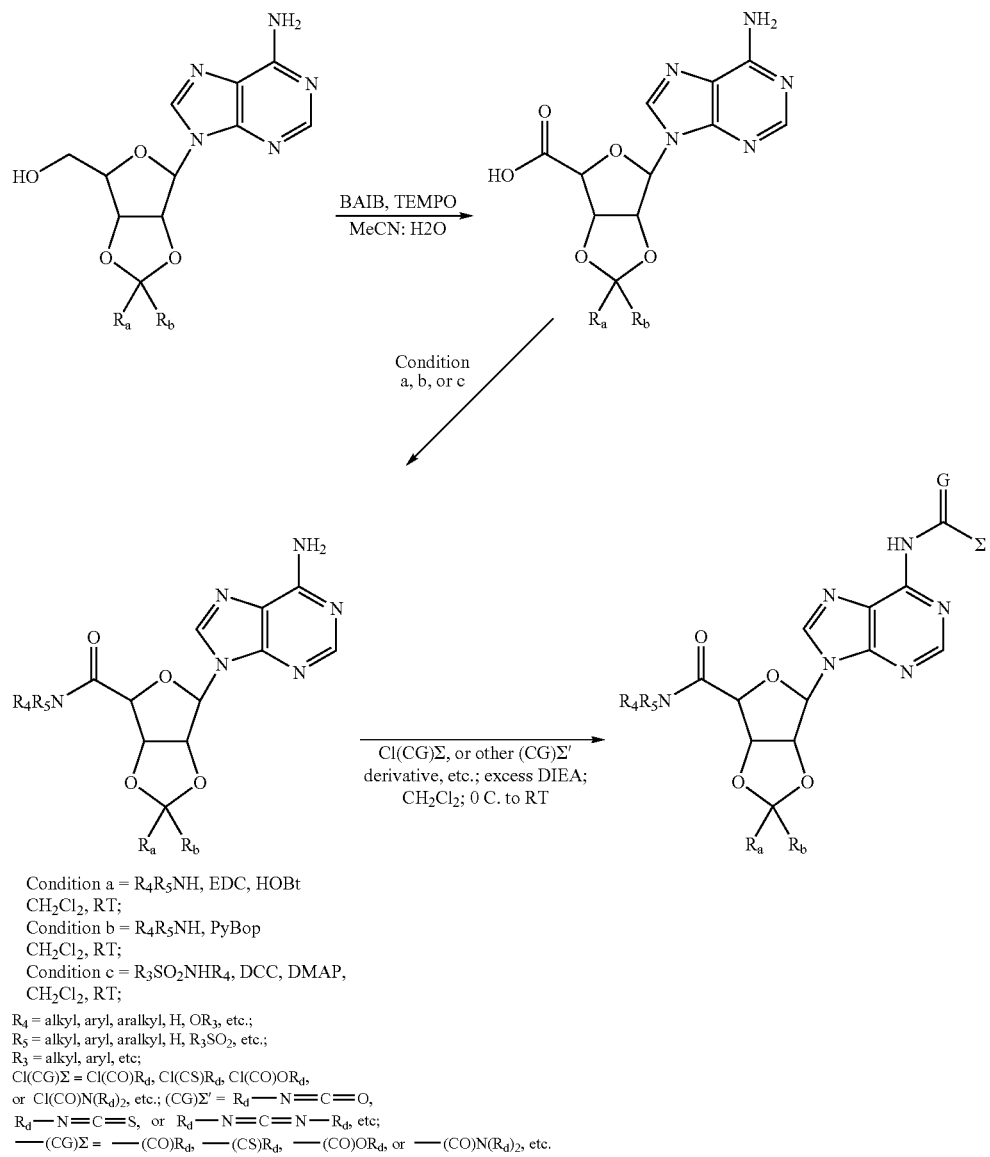

Condition a = $R_4R_5NH$, EDC, HOBt $CH_2Cl_2$, RT;
Condition b = $R_4R_5NH$, PyBop $CH_2Cl_2$, RT;
Condition c = $R_3SO_2NHR_4$, DCC, DMAP, $CH_2Cl_2$, RT;
$R_4$ = alkyl, aryl, aralkyl, H, $OR_3$, etc.;
$R_5$ = alkyl, aryl, aralkyl, H, $R_3SO_2$, etc.;
$R_3$ = alkyl, aryl, etc;
$Cl(CG)\Sigma = Cl(CO)R_d, Cl(CS)R_d, Cl(CO)OR_d,$
or $Cl(CO)N(R_d)_2$, etc.; $(CG)\Sigma' = R_d-N=C=O,$
$R_d-N=C=S,$ or $R_d-N=C=N-R_d,$ etc;
$-(CG)\Sigma = -(CO)R_d, -(CS)R_d, -(CO)OR_d,$ or $-(CO)N(R_d)_2$, etc.

2', 3'-O-Isopropylideneadenosine-5'-carboxylic acid and related acetals and ketals are useful intermediates for the preparation of various amides and sulfonamide derivatives. An intermediate of this type can be used in both solution phase and solid phase synthetic schemes to prepare compounds with various substituents at the 5'-, 2', 3'-acetal/ketal-, and 6-positions- of adenosines or related purine derivatives as provided in Scheme 7. The methods shown in Scheme 7 are also useful for the preparation of substituted purine derivatives, and/or 8-azapurine derivatives.

Compounds containing the adenosine 5'-carboxylic acid unit shown in Scheme 7, or related $N^6$-substituted-adenosine-5'-carboxylic acids and 8-azaadenosine-5'carboxylic acids can also be used for the synthesis of esters or other materials useful in this invention using literature methods. In addition, the $N^6$-amine of such an acid can be transformed into a urea, thiourea, amide, carbamate, guanidine, etc., to give a material that is also useful for this invention. Alternatively, a protecting group such as an amide (e.g., a benzamide, formamide, or trifluoroacetamide) or a carbamate (e.g., Boc, Cbz, Fmoc, etc.) can be installed on the $N^6$ position, and then the acid moiety which is at, or linked to, the 5'-position of the furanose derivative can be coupled to a solid phase resin such as a 4-sulfamylbutyryl resin, hydroxymethyl resin, or a pegylated-hydroxy resin, etc., using techniques well-known in the literature to give a resin-bound material. The benefits of solid-phase chemistry can then be gained for modification of a resin-bound material by transketalization techniques similar to those shown in Schemes 4 and 5. If a protecting group is used on the $N^6$-position of such an acid, it can be removed subsequent to a transketalization procedure to give a resin-bound compound which can be cleaved from the solid phase and purified to give a compound of the invention. Or, if desired, a $N^6$-amine so formed on the solid phase can then be converted into an amide, carbamate, urea, thiourea or guanidine, etc., by methods disclosed herein, or by methods in the literature. Cleavage from the solid support using known methods then yields a compound of the invention which can be purified, if needed, by employing commonly-used techniques.

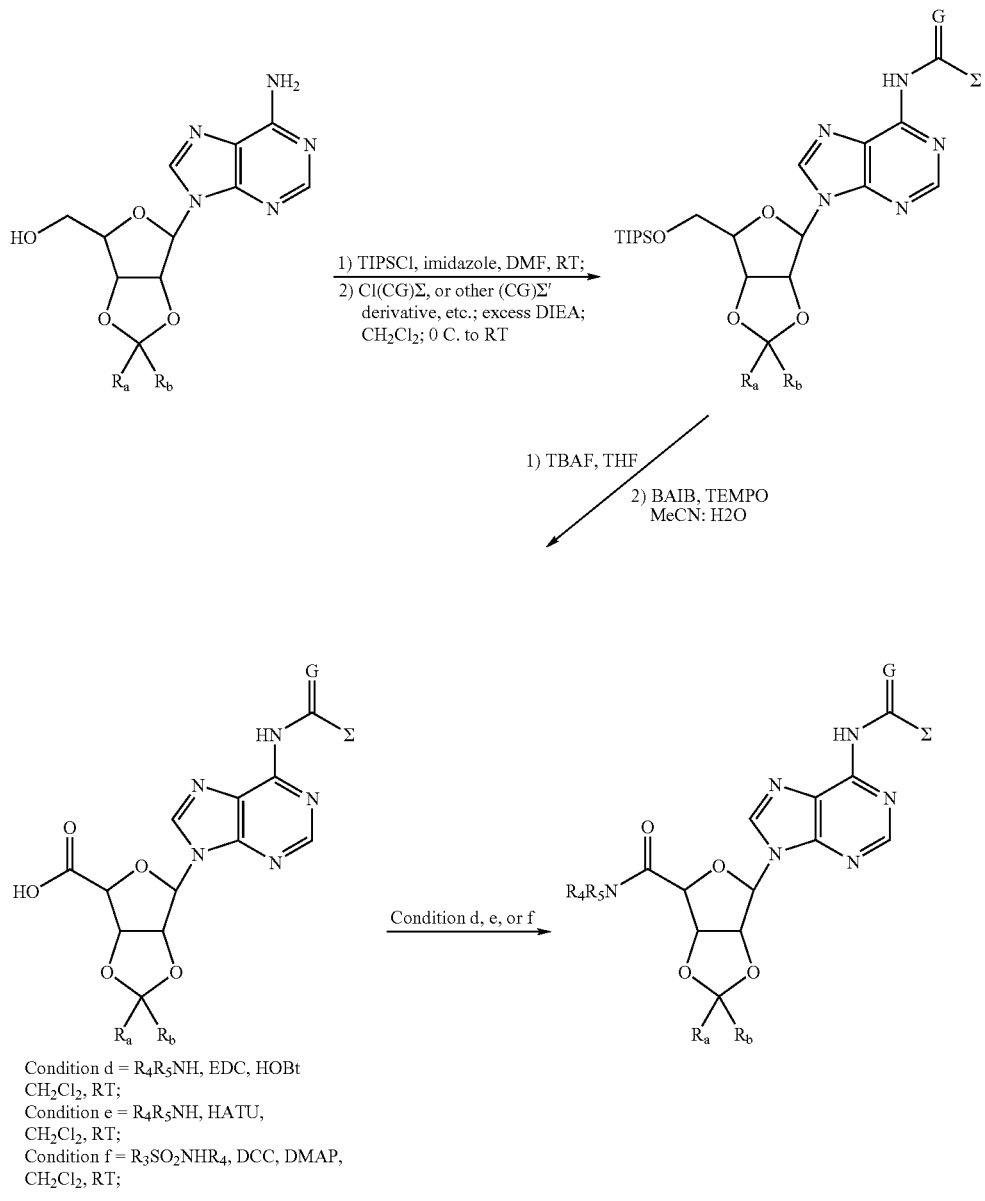

Scheme 8. $N^6$-modification of adenosine derivatives, followed by oxidation to a 5'-carboxylic acid, and 5'-amide formation Condition d = $R_4R_5NH$, EDC, HOBt $CH_2Cl_2$, RT;
Condition e = $R_4R_5NH$, HATU, $CH_2Cl_2$, RT;
Condition f = $R_3SO_2NHR_4$, DCC, DMAP, $CH_2Cl_2$, RT;

$R_4$ = alkyl, aryl, aralkyl, H, $OR_3$, etc.;
$R_5$ = alkyl, aryl, aralkyl, H, $R_3SO_2$, etc.;
$R_3$ = alkyl, aryl, etc;
$Cl(CG)\Sigma = Cl(CO)R_d, Cl(CS)R_d, Cl(CO)OR_d$,
or $Cl(CO)N(R_d)_2$, etc.; $(CG)\Sigma' = R_d-N=C=O$,
$R_d-N=C=S$, or $R_d-N=C=N-R_d$, etc;
—$(CG)\Sigma$ = —$(CO)R_d$, —$(CS)R_d$, —$(CO)OR_d$, or —$(CO)N(R_d)_2$, etc.

A variation of the method disclosed in Scheme 7, useful for the introduction of a group at $N^6$ prior to oxidation of the 5'-position of an adenosine derivative or an 8-azaadenosine derivative, is shown in Scheme 8. Although Scheme 8 shows an adenine unit, it will be understood by chemistry practitioners that the methods of Scheme 8 are generally applicable to substituted members of the adenine family and also to the 8-azaadenines. Preferred amines and amine derivatives for the 5'-amide-forming reactions shown in Schemes 7 and 8 are: trifluoromethanesulfonamide, methanesulfonamide, serine, glycine, proline, anthranilic acid and its regioisomers, and methyl anthranilate and its regioisomers.

rally-occurring, as well as synthetically-derived amino acids and peptides, or derivatives, to a 5'-carboxylic acid or related homologue is exemplified in Scheme 9 using the amino acid, proline.

An example of the method is shown in Scheme 9 utilizing a resin-linker combination like the polystyrene/HESM as a solid phase. Other solid phase/linkers known in the art can be used in this method. Attachment of a group, such as an amino acid, (e.g., proline, as shown) or a series of amino acids or a peptide, by well-known methods in the art of solid phase synthesis yields a resin-linked amine. Said amine can then be reacted with an adenosine 5'-carboxylic acid, or another type

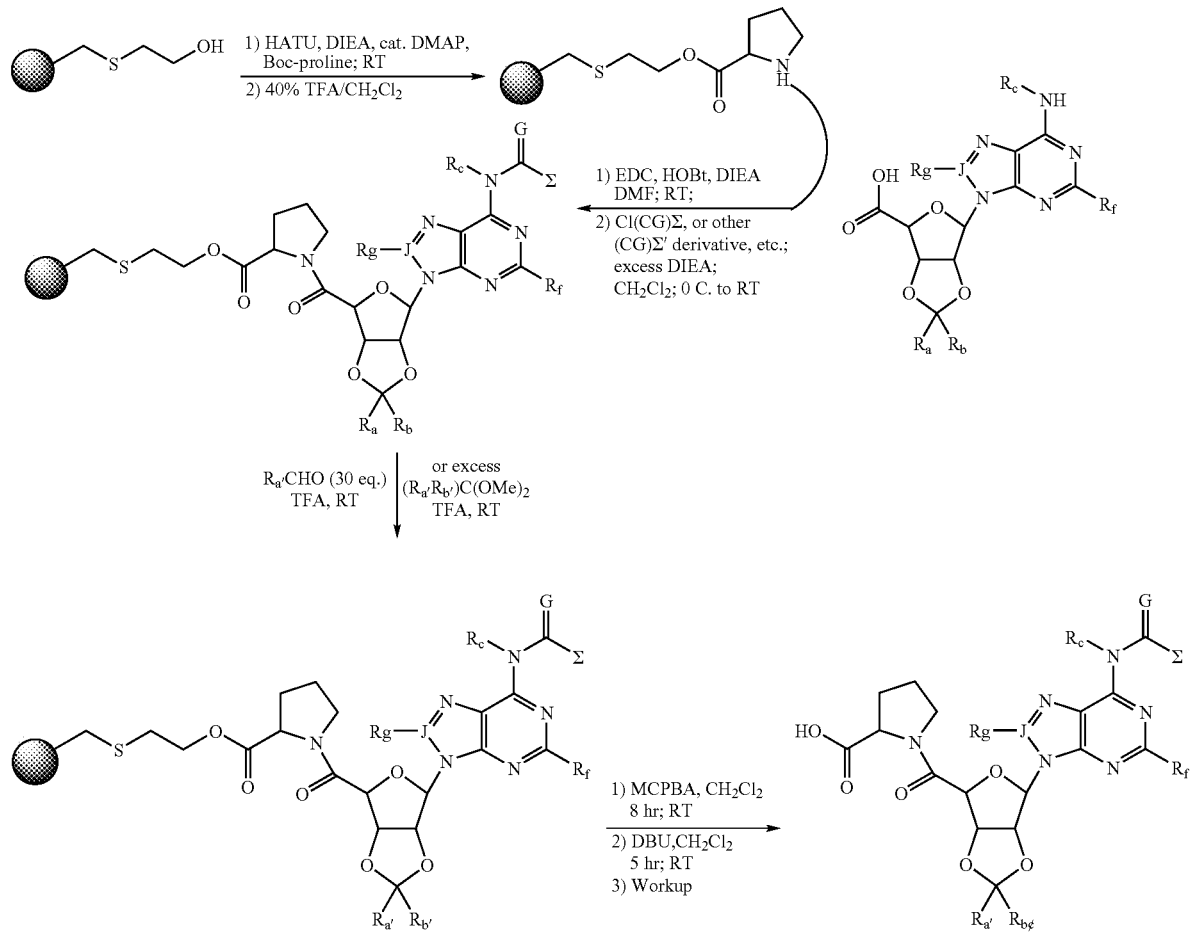

Scheme 9. Amino acid amides of 5'-adenosinecarboxylic acid derivatives and 8-azaadenosine-5'-carboxylic acid derivatives using solid phase techniques.

Where $R_{a'}$ and $R_{b'}$ denote
different $R_a$ and/or $R_b$
$Cl(CG)\Sigma = Cl(CO)R_d, Cl(CS)R_d, Cl(CO)OR_d,$
or $Cl(CO)N(R_d)_2$, etc.; $(CG)\Sigma' = R_d\!-\!N\!=\!C\!=\!O,$
$R_d\!-\!N\!=\!C\!=\!S,$ or $R_d\!-\!N\!=\!C\!=\!N\!-\!R_d$, etc;
$\!-\!(CG)\Sigma = \!-\!(CO)R_d, \!-\!(CS)R_d, \!-\!(CO)OR_d,$ or $\!-\!(CO)N(R_d)_2$, etc.

Amide derivatives of 5'-carboxylic acids (e.g., those shown in Scheme 7 and Scheme 8) or amide derivatives of acid moieties linked at the 5'-position of Formula I can also include amides derived from amino acids, peptides, amino alcohols and the like. A convenient way of attaching natuof derivative useful for making compounds of this invention, to yield a coupled product. The said coupled product, if it bears an amine at the 6-position, can then be treated with one of the various reagents described previously, or with a reagent known in the literature, to yield an amide, carbamate, urea, thiourea or guanidine, etc., at the adenosine 6-position. Alternatively, if a 5'-carboxylic acid derivative used in a coupling to a solid phase has a desired group already installed at the 6-position, then the latter said modification at $N^6$ need not be performed. If desired, a coupled 5'-amide/$N^6$-functionalized product can be converted into a variety of different acetals or ketals using solid phase methods such as described for Schemes 4 and 5. When a synthesis is complete, cleavage of a compound of the invention from a solid phase can be performed by a variety of methods known in the art; such cleavage conditions depending upon the type of linker used. Cleavage methodologies useful for cleaving peptide- or amino acid derivatives of 5'-linked-adenosine compounds comprise the linker oxidation/elimination procedures given in Schemes 5 and 9; treatment with a hydroxide source, such as lithium hydroxide, using conditions as for the ester hydrolysis described in Scheme 6; and hydrolysis using potassium trimethylsilanolate, as described in Scheme 4; as well as others known in the art (including aminolysis to form amides) which are useful for cleavage of other resin/linker/ester combinations. If desired, a compound useful in this invention can be obtained in purified form by cleaving it from a resin and purifying it as described previously.

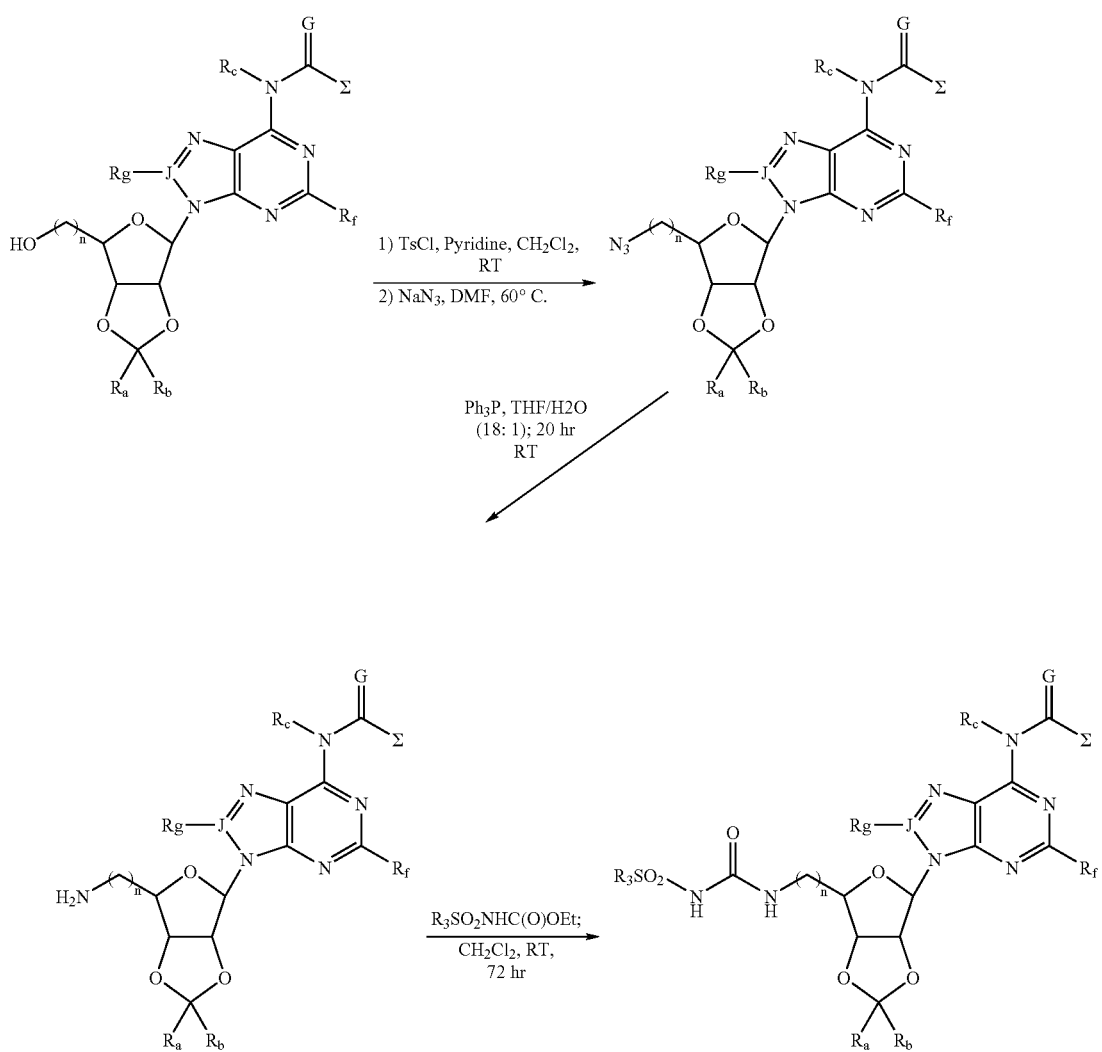

Scheme 10. Synthesis of 5'-amines and 5'-amine derivatives of nucleosides and 8-azanucleosides.

In another embodiment, an amino group can be installed at the 5'-position of an adenosine or 8-azaadenosine analogue, or on the chain of a 5'-homologue of such a material. This amine can be utilized to form amide-, sulfonamide-, and other derivatives. Scheme 10 illustrates how a sulfonylurea can be synthesized at the 5'-position using a 5'-amine, or at related positions on homologous amine derivatives. In addition, an amine introduced at the 5'-position or on the 5'-chain of a homologue is also useful for the synthesis of amides, ureas, carbamates, sulfonamides and other amine derivatives using methods known in the art for such processes.

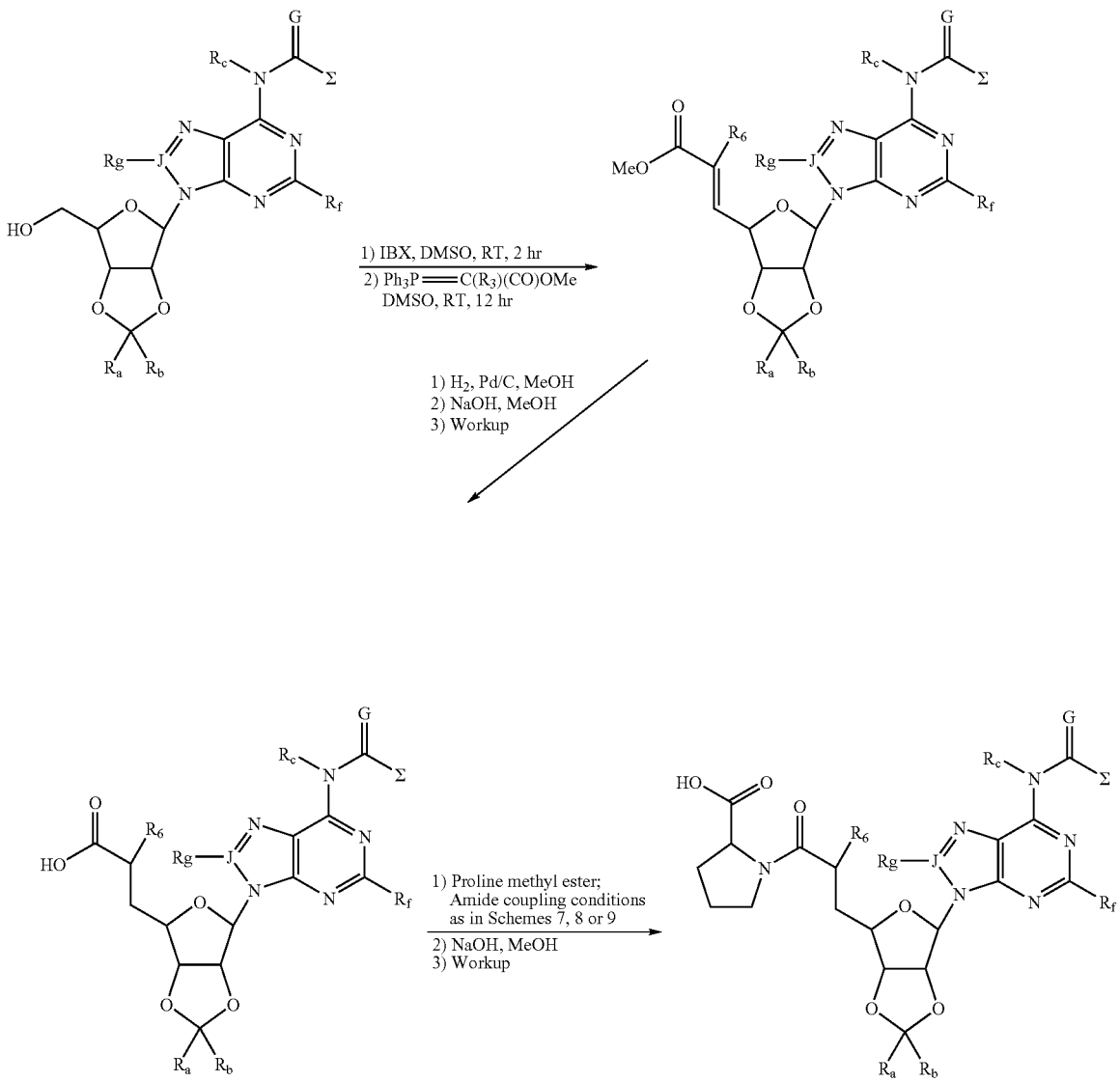

Scheme 11. Homologation of adenosine, including steps involving oxidation, Horner-Emmons Reaction, reduction, and coupling with amines.

$R_6$ = H, alkyl, aryl, etc.;
—(CG)Σ = —(CO)$R_d$, —(CS)$R_d$, —(CO)O$R_d$, or —(CO)N($R_d$)$_2$, etc.

In still another embodiment, the 5'-position of the nucleoside derivative or 8-azanucleoside derivative is homologated with one or more carbon atoms. Scheme 11 illustrates the preparation of a class of homologated adenosine analogs which are useful for the invention. Or, if desired, such a homologue can subsequently be coupled with an amino acid to give other compounds useful for this invention. In Schemes 11 and 12, a proline is used to exemplify the amide coupling, but other amines or amino acid derivatives can be employed. In Scheme 12, the reduction step of Scheme 11 is omitted, which generates unsaturated homologues useful in this invention.

Methods of Administration

The active compounds disclosed herein are administered in a sufficient amount or amounts to reduce or alleviate the sensation of pain in a subject in need of such treatment by either systemic administration, or direct administration to the painful area of a subject by any suitable means. In one embodiment, a compound of the invention is administered by administering a liquid or gel suspension of the active compound in the form of injection, drops, spray or gel. In a second embodiment, the active compound or compounds may be applied to the painful area via liposomes and/or using a cream formulation. In a third embodiment, the active compound or

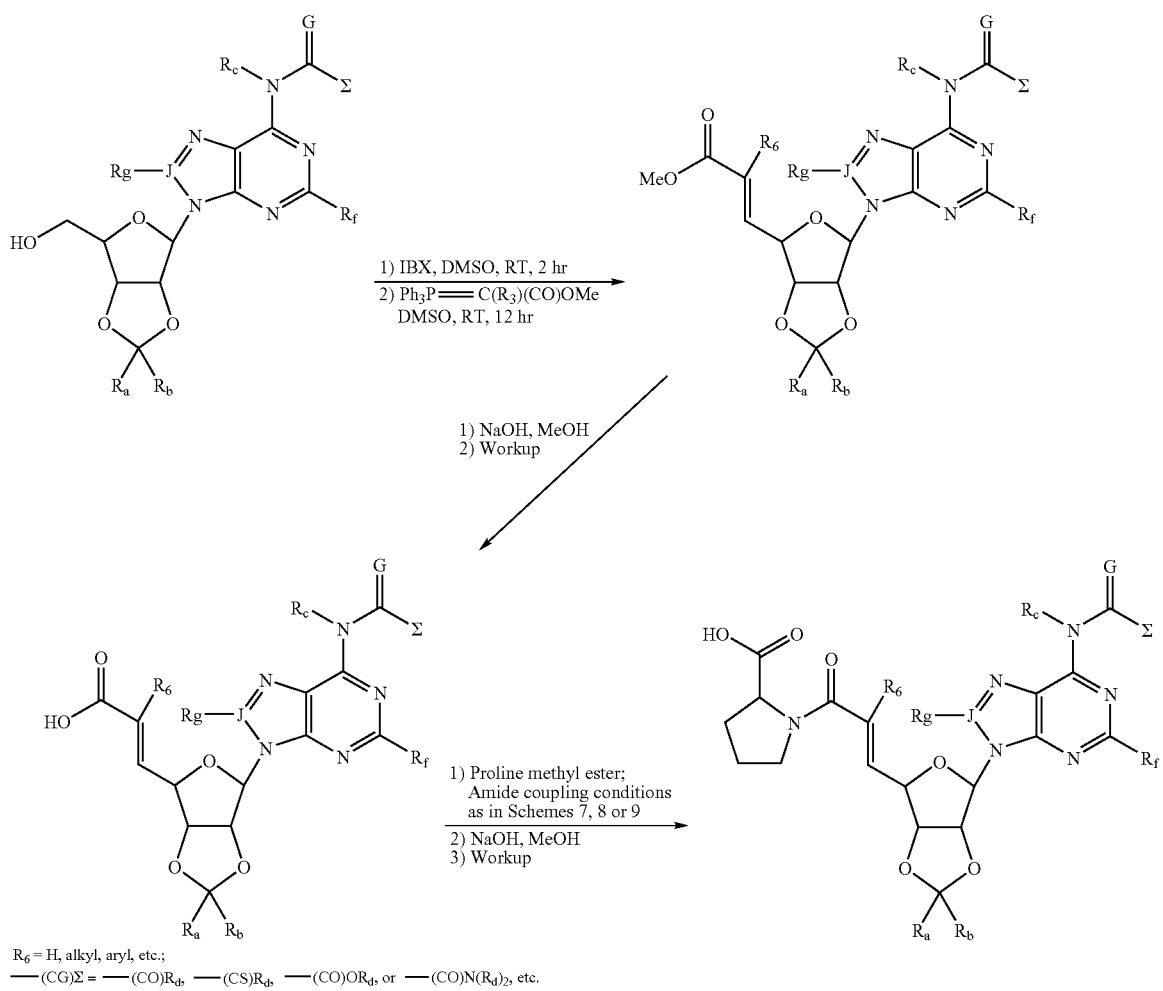

Those having skill in the art will recognize that the starting materials can be varied and additional steps employed to produce compounds encompassed by the present invention, as shown in the above schemes, as demonstrated by the examples which follow, and/or by appropriate modification of reactions known in the art. In some cases, protection of certain reactive functionalities may be necessary to achieve some of the above transformations. In general, the need for such protecting groups as well as the conditions necessary to attach and remove such groups will be apparent to those skilled in the art.

compound may be infused into the painful area via a pump-catheter system. In a fourth embodiment, one or more active compounds can be administered orally by any suitable means known in the art, but preferably said oral administration is in the form of a tablet, caplet, or capsule. Another embodiment of the present invention involves the active compound contained within a continuous or selective-release device, for example, membranes such as, but not limited to, those employed in the OCUSERT™ System (Alza Corp., Palo Alto, Calif.). As an additional embodiment, the active compound or compounds can be contained within, carried by, or attached to contact lenses that are placed on the eye, or adhesive bandages placed on the skin. Another embodiment of the present invention involves at least one active compound contained within or placed on a swab or sponge that can be applied to the painful area. Another embodiment of the present invention involves the active compound or compounds contained within a liquid spray that can be applied to the painful area. Such a spray also can be used for intranasal administration of one or more compounds of this invention such that one or more active materials contact a painful area of the nasal and/or sinus passages and reduce the sensation of pain in that area either by direct contact with the material or by systemic absorption. Other embodiments of the present invention involve an injection of at least one active compound directly into the painful area or application of at least one active compound directly or indirectly onto the surface of the painful area.

The quantity of each active compound of the invention included in a pharmaceutical composition of the present invention is an amount that is effective in reducing pain. The amount of each compound of the invention used is preferably an amount sufficient to achieve dissolved concentrations of each active compound in the painful area of the subject of from about $10^{-7}$ to about $10^{-1}$ moles/liter, and more preferably from about $10^{-6}$ to about $10^{-1}$ moles/liter, in order to antagonize the nociceptive effects of P2X receptors.

A topical solution comprising the active compound optimally contains a physiologically compatible vehicle, as those skilled in the art can select using conventional criteria. The vehicles are selected from the known ophthalmic, intranasal and cutaneous vehicles which include, but are not limited to, saline solution, water-soluble polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In addition to the topical method of administration described above, there are various methods of administering the active compounds of the present invention systemically. One such means would involve an aerosol suspension of respirable particles comprising the active compound, which the subject inhales. The active compound would be absorbed into the bloodstream via the lungs, and subsequently affect a painful area in a pharmaceutically effective amount. The respirable particles may be liquid or solid, with a particle size sufficiently small to pass the mouth and larynx upon inhalation; in general, particles ranging from about 1 to 10 microns, but more preferably 1-5 microns, in size are considered respirable.

Another means of systemically administering the active compounds to the eyes of the subject would involve administering a liquid/liquid suspension in the form of eye drops or eye wash or nasal drops of a liquid formulation, or a nasal spray of respirable particles that the subject inhales. Liquid pharmaceutical compositions of the active compound for producing a nasal spray, or nasal or eye drops may be prepared by combining the active compound with a suitable vehicle, such as sterile pyrogen-free water or sterile saline by techniques known to those skilled in the art.

Other means of systemic administration of the active compound would involve oral administration, in which pharmaceutical compositions containing active compounds are in the form of tablets, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions may contain one or more agents selected from the group comprising sweetening agents, flavoring agents, coloring agents and preserving agents in order to provide pharmaceutically elegant and palatable preparations. Tablets contain the active ingredient in admixture with nontoxic pharmaceutically acceptable excipients that are suitable for the manufacture of tablets. These excipients include, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Additional means of systemic administration of the active compound to the painful area of the subject would involve a suppository or pessary form of the active compound, such that a therapeutically effective amount of the compound reaches the painful area via contact or via systemic absorption and circulation.

Further means of systemic administration of the active compound would involve direct intra-operative instillation of a gel, cream, or liquid suspension form of a therapeutically effective amount of the active compound.

The method of the present invention can be used with other therapeutic and adjuvant agents commonly used to reduce pain, thus enhancing the effects of therapeutic agents and adjunctive agents. Other therapeutic agents used include opioids (morphine, fentanyl), sodium channel blockers (novocaine, lidocaine), NSAIDS (aspirin, ibuprofen), and COX-2 inhibitors (VIOXX®, CELEBREX®).

High doses are sometimes required for some therapeutic agents to achieve levels to effectuate the target response, but high doses are often associated with a greater frequency of dose-related adverse effects. Thus, combined use of one or more of the compounds of the present invention with therapeutic agents commonly used to treat pain allows the use of relatively lower doses of other agents, which results in a lower frequency of adverse side effects associated with long-term administration of such agents. Thus, another advantage of the compounds in this invention is to reduce adverse side effects of other drugs used to treat pain. Side effects known for other drugs, such as tolerance, dependence, constipation, respiratory depression, sedation, gastrointestinal side effects and increased bleeding time, can be reduced by administering a dose of one or more compounds of this invention to a subject in need of pain reduction which thereby allows the concomitant reduction of a dose of another compound used to treat pain.

The invention is illustrated further by the following examples that are not to be construed as limiting the invention in scope to the specific procedures described in them.

EXAMPLES

Example 1

Preparation of 5'-Aryl Ether Derivatives

5-Amino-2-{2-benzyl-6-[6-(3-phenyl-ureido)-purin-9-yl]-tetrahydro-furo[3,4-d][1,3]dioxol-4-yl-methoxy}-benzoic acid Adenosine (10 g, 37 mmol was dissolved in N,N-dimethyl formamide (100 mL) and dimethoxypropane (25 mL) followed by addition of Amberlyst 15H$^+$ resin. The mixture was stirred 3 h at 55° C. The resin was removed by filtration and the solvents removed in vacuo, affording 2', 3'-di-O-isopropylidene adenosine (11 g, 95%).

This product (6 g, 20 mmol) was dissolved in N,N-dimethyl formamide (22 mL) and stirred with triisopropylsilyl chloride and imidazole 16 h at 23° C. The solution was partitioned between ether (200 mL) and brine (100 mL) and the ether phase washed with additional brine (2×50 mL). The ether was dried over magnesium sulfate and evaporated, affording 5'-O-triisopropylsilyl-2', 3'-di-O-isopropylidene adenosine.

This residue was dissolved in toluene (20 mL) and treated with phenylisocyanate (3.6 g, 30 mmol) for 16 h at 25° C. A solution of sodium bicarbonate (1 mL of 10 M) was added and the mixture evaporated to dryness. The residue was partitioned between ethyl acetate (100 mL) and water (25 mL). The organic phase was dried with magnesium sulfate and evaporated to dryness. The solid was dissolved in tetrahydrofuran (20 mL) and stirred with tetrabutyl ammonium fluoride in tetrahydrofuran (20 mL of a 1 M solution) for 1 h in a dry ice/acetone bath. Removal of the solvent in vacuo followed by washing with hexane afforded the 5'-alcohol (5.3 g).

A portion of the above phenylurea product (0.41 g, 0.96 mmol) was suspended in 25 mL of 20% aqueous acetic acid and 5 mL of tetrahydrofuran/dioxane (1:1) and was stirred at 50° C. for 24 h. The white suspension became a clear yellow solution. The mixture was concentrated and then lyophilized, to give 0.360 g (97% yield) of 1-[9-(3,4-dihydroxy-5-hydroxymethyl-tetrahydro-furan-2-yl)-9H-purin-6-yl]-3-phenyl-urea as a yellow solid. MW calculated for $C_{17}H_{18}N_6O_5$ (MH$^+$) 387, found 387 by LCMS.

A small amount of 4A flame dried molecular sieves (cooled down by a flow of argon) was added to a vial containing a portion of the product immediately above (0.131 g, 0.34 mmol). The mixture was capped with a rubber septum and cooled down to 0° C. To this mixture trifluoroacetic acid (2.5 mL) was added via syringe and the mixture stirred at this temperature for 15 min. Phenyl acetaldehyde dimethylacetal (0.230 ml, 4 eq.) was added dropwise and the mixture stirred at 0° C. for 2 h. One more equivalent of phenyl acetaldehyde dimethyl acetal was added and stirred an additional five hours. The volatiles were evaporated off and the residue was purified by flash chromatography (hexane: ethyl acetate, 8:2, 1% triethylamine) to give 0.095 g of product (60% yield) as a yellow solid. MW calculated for $C_{25}H_{24}N_6O_5$ (MH$^+$) 489, found 489 by LCMS.

A portion of this acetal product (0.068 g, 0.14 mmol) was dissolved in dry N,N-dimethyl formamide (2.5 mL) and potassium tert-butoxide (0.084 g, 5 eq) was added to give a yellow solution. To this mixture was added 2-fluoro-5-nitrobenzoic acid (0.046 g, 1.8 eq). After 2.5 h of stirring at room temperature the mixture was concentrated and purified by preparative HPLC to give the nucleoside analog as a white powder. MW calculated for $C_{32}H_{27}N_7O_9$ (MH$^+$) 654, found 654 by LCMS.

The nitro group of the product immediately above was reduced under a hydrogen atmosphere with a catalytic amount of 10% Pd/C in methanol during 6 h. Filtration through Celite followed by HPLC purification yielded 52 mg (62% yield) of the title compound as clear semisolid.

Example 2

Preparation of 5'-Heteroaryl Ether Derivatives

2-{2,2-Dimethyl-6-[6-(3-phenyl-ureido)-purin-9-yl]-tetrahydro-furo[3,4-d][1,3]dioxol-4-ylmethoxy}-nicotinic acid To a stirred solution of 1-[9-(6-hydroxymethyl-2,2-dimethyl-tetrahydro-furo[3,4-d][1,3]dioxol-4-yl)-9H-purin-6-yl]-3-phenyl-urea (43 mg, 0.1 mmol) in dry N, N'-dimethylformamide (1 mL) at 23° C. was added potassium tert-butoxide (45 mg, 0.4 mmol). After 30 min, 2-chloronicotinic acid (60 mg, 0.4 mmol) was added to the solution. The resulting mixture was stirred at 23° C. for 15 h and then quenched with water (1 mL), suspended in ethyl acetate (50 mL), washed with brine (3×), dried over anhydrous sodium sulfate, filtered and concentrated in vacuo to give the crude product. Preparative reverse-phase HPLC was used to obtain the pure compound (15 mg, 27% yield) as a white solid. $^1$H NMR (300 MHz, DMSO-d$_6$) δ 11.76 (s, 1H), 10.15 (s, 1H), 9.16 (s, 1H), 8.65 (s, 1H), 8.05 (dd, J=8.5 Hz, 3.5 Hz, 1H), 7.94 (dd, J=9.0 Hz, 3.0 Hz, 1H), 7.60 (d, J=2.0 Hz, 1H), 7.57 (d, J=2.0 Hz, 1H), 7.32 (t, J=12.5 Hz, 2H), 7.05 (t, J=12.5 Hz, 1H), 6.96 (dd, J=12.5 Hz, 8.5 Hz, 1H), 6.25 (d, J=6.0 Hz, 1H), 5.80 (t, J=7.5 Hz, 1H), 5.10 (dd, J=9.0 Hz, 2.5 Hz, 1H), 4.67 (m, 1H), 4.53 (dd, J=20.0 Hz, 4.0 Hz, 1H), 4.36 (dd, J=20.0 Hz, 4.0 Hz, 1H), 1.59 (s, 3H), 1.38 (s, 3H). MW calculated for $C_{26}H_{25}N_7O_7$ (MH$^+$) 548, found 548 by LCMS.

Similarly, other 5'-substituted pyridines were prepared:

6-{2,2-Dimethyl-6-[6-(3-phenyl-ureido)-purin-9-yl]-tetrahydro-furo[3,4-d][1,3]dioxol-4-ylmethoxy}-nicotinic acid (9 mg, 8% yield) as a white solid. $^1$H NMR (300 MHz, DMSO-d$_6$) δ 11.68 (s, 1H), 10.20 (s, 1H), 8.71 (s, 1H), 8.64 (d, J=3.0 Hz, 2H), 8.12 (dd, J=15.0 Hz, 3.5 Hz, 1H), 7.63 (d, J=2.0 Hz, 1H), 7.61 (d, J=1.5 Hz, 1H), 7.36 (t, J=13.0 Hz, 2H), 7.09 (t, J=12.5 Hz, 1H), 6.84 (dd, J=13.5 Hz, 1.0 Hz, 1H), 6.33 (d, J=3.5 Hz, 1H), 5.61 (dd, J=10.0 Hz, 4.0 Hz, 1H), 5.20 (dd, J=10.0 Hz, 4.5 Hz, 1H), 4.64 (m, 1H), 4.54 (m, 2H), 1.60 (s, 3H), 1.40 (s, 3H). MW calculated for $C_{26}H_{25}N_7O_7$ (MH$^+$) 548, found 548 by LCMS.

6-{2,2-Dimethyl-6-[6-(3-phenyl-ureido)-purin-9-yl]-tetrahydro-furo[3,4-d][1,3]dioxol-4-ylmethoxy}-pyridine-2-carboxylic acid (5 mg, 4.6% yield) as a white solid. $^1$H NMR (300 MHz, DMSO-d$_6$) δ 11.64 (s, 1H), 10.15 (s, 1H), 8.68 (s, 1H), 8.60 (s, 1H), 7.83 (dd, J=13.5 Hz, 12.5 Hz, 1H), 7.62 (m, 3H), 7.34 (t, J=12.5 Hz, 2H), 7.06 (t, J=12.5 Hz, 1H), 6.96 (dd, J=13.0 Hz, 1.0 Hz, 1H), 6.30 (d, J=4.0 Hz, 1H), 5.59 (dd, J=10.0 Hz, 4.5 Hz, 1H), 5.17 (dd, J=10.0 Hz, 4.5 Hz, 1H), 4.64 (m, 1H), 4.50 (m, 2H), 1.58 (s, 3H), 1.38 (s, 3H). MW calculated for $C_{26}H_{25}N_7O_7$ (MH$^+$) 548, found 548 by LCMS.

5-Chloro-6-{2,2-dimethyl-6-[6-(3-phenyl-ureido)-purin-9-yl]-tetrahydro-furo[3,4-d][1,3]dioxol-4-yl-methoxy)-nicotinic acid (11 mg, 1.5% yield) as a white solid. MW calculated for $C_{26}H_{24}ClN_7O_7$ (MH$^+$) 582, found 582 by LCMS.

6-Chloro-2-{2,2-dimethyl-6-[6-(3-phenyl-ureido)-purin-9-yl]-tetrahydro-furo[3,4-d][1,3]dioxol-4-yl-methoxy}-nicotinic acid (isomer A) & 2-Chloro-6-{2,2-dimethyl-6-[6-(3-phenyl-ureido)-purin-9-yl]-tetrahydro-furo[3,4-d][1,3]dioxol-4-ylmethoxy)-nicotinic acid (isomer B)

Two isomer were obtained from the reaction with 2,6-dichloronicotinic acid. The major product was A (80 mg, 69% yield). LC-MS calculated for $C_{26}H_{24}ClN_7O_7$ (MH$^+$) 582, found 582. The minor product was B (20 mg, 17% yield). MW calculated for $C_{26}H_{24}ClN_7O_7$ (MH$^+$) 582, found 582 by LCMS.

2-Chloro-6-{2,2-dimethyl-6-[6-(3-phenyl-ureido)-purin-9-yl]-tetrahydro-furo[3,4-d][1,3]dioxol-4-yl-methoxy}-isonicotinic acid (60 mg, 52% yield) as a white solid. $^1$H NMR (300 MHz, DMSO-d$_6$) δ 11.63 (s, 1H), 10.18 (s, 1H), 8.68 (s, 1H), 8.61 (s, 1H), 7.6 (s, 1H), 7.59 (s, 1H), 7.36 (s, 1H), 7.33 (t, J=13.0 Hz, 2H), 7.06 (t, J=13.5 Hz, 1H), 6.29 (d, J=3.5 Hz, 1H), 5.63 (dd, J=10.0 Hz, 4.0 Hz, 1H), 5.17 (dd, J=10.0 Hz, 4.5 Hz, 1H), 4.64 (m, 1H), 4.47 (m, 2H), 1.60 (s, 3H), 1.38 (s, 3H). MW calculated for $C_{26}H_{24}ClN_7O_7$ (MH$^+$) 582, found 582 by LCMS.

6-{2,2-Dimethyl-6-[6-(3-phenyl-ureido)-purin-9-yl]-tetrahydro-furo[3,4-d][1,3]dioxol-4-ylmethoxy}-nicotinamide (15 mg, 14% yield) as a white solid. $^1$H NMR (300 MHz, DMSO-d$_6$) δ 11.70 (s, 1H), 10.10 (s, 1H), 8.69 (s, 1H), 8.61 (s, 1H), 8.60 (d, J=4.0 Hz, 1H), 8.09 (dd, J=10.0 Hz, 4.0 Hz, 1H), 7.95 (s, 1H), 7.62 (s, 1H), 7.59 (s, 1H), 7.39 (s, 1H), 7.34 (t, J=15.0 Hz, 2H), 7.07 (t, J=12.5 Hz, 1H), 6.80 (d, J=14.0 Hz, 1.0 Hz, 1H), 6.31 (d, J=4.0 Hz, 1H), 5.59 (dd, J=10.5 Hz, 4.5 Hz, 1H), 5.17 (dd, J=10.0 Hz, 4.5 Hz, 1H), 4.63 (m, 1H), 4.49 (m, 2H), 1.59 (s, 3H), 1.39 (s, 3H). MW calculated for $C_{26}H_{26}N_8O_6$ (MH$^+$) 547 found 547 by LCMS.

6-Chloro-2-{2,2-dimethyl-6-[6-(3-phenyl-ureido)-purin-9-yl]-tetrahydro-furo[3,4-d][1,3]dioxol-4-yl-methoxy}-5-fluoro-nicotinic acid (35 mg, 19% yield) as a white solid. MW calculated for $C_{26}H_{23}ClFN_7O_7$ (MH$^+$) 600, found 600 by LCMS.

1-{9-[6-(3-Hydroxy-pyridin-2-yloxymethyl)-2,2-dimethyl-tetrahydro-furo[3,4-d][1,3]dioxol-4-yl]-9H-purin-6-yl}-3-phenyl-urea Dry argon was bubbled through a solution of 1-{9-[6-(3-Benzyloxy-pyridin-2-yloxymethyl)-2,2-dimethyl-tetrahydro-furo[3,4-d][1,3]dioxol-4-yl]-9H-purin-6-yl}-3-phenyl-urea (18 mg, 0.03 mmol, prepared as above) in methanol/ethyl acetate (1:1 v/v, 10 mL) at 23° C. for 10 min. Palladium on activated carbon (10%) was added and the suspension was degassed by argon for another 5 min. Hydrogen (H$_2$) was conducted to the solution via a balloon, and the reaction proceeded for 5 h. The mixture was filtered and concentrated in vacuo to give the crude product. Preparative reverse-phase HPLC was used to obtain the pure compound (5 mg, 31% yield) as a white solid. MW calculated for $C_{25}H_{25}N_7O_6$ (MH$^+$) 520, found 520 by LCMS.

2-{2-Benzyl-6-[6-(3-phenyl-ureido)-purin-9-yl]-tetrahydro-furo[3,4-d][1,3]dioxol-4-ylmethoxy}-nicotinic acid 2-{2,2-Dimethyl-6-[6-(3-phenyl-ureido)-purin-9-yl]-tetrahydro-furo[3,4-d][1,3]dioxol-4-ylmethoxy}-nicotinic acid (180 mg, 0.33 mmol) was dissolved in a mixture of trifluoroacetic acid and water (TFA/H$_2$O, 4:1 v/v, 20 mL), and the suspension was stirred at 23° C. for 30 min. The solvents were removed under reduced pressure to give the intermediate diol product (120 mg, 72% yield) as a white solid. MW calculated for $C_{23}H_{21}N_7O_7$ (MH$^+$) 508, found 508 by LCMS.

To a stirred solution of the diol immediately above (0.23 mmol) in dry trifluoroacetic acid (5 mL) at 23° C. was added phenyl acetaldehyde (130 mg, 1.1 mmol). The resulting mixture was stirred at 23° C. for 6 h. After the removal of most trifluoroacetic acid by evaporation under reduced pressure, the reaction was quenched with saturated sodium bicarbonate solution (10 mL). The product was extracted using ethyl acetate (50 mL), washed with brine (3×), dried over anhydrous sodium sulfate, filtered and concentrated in vacuo to give the crude product. Preparative reverse-phase HPLC was used to obtain the pure acetal compound (7 mg, 5% yield) as a white solid. $^1$H NMR (300 MHz, DMSO-d$_6$) δ 11.67 (s, 1H), 10.50 (s, 1H), 8.68 (s, 1H), 8.51 (s, 1H), 8.27 (dd, J=8.0 Hz, 3.0 Hz, 1H), 8.10 (dd, J=10.0 Hz, 4.0 Hz, 1H), 7.60 (dd, J=14.0 Hz, 2.0 Hz, 1H), 7.30 (m, 7H), 7.08 (m, 3H), 6.21 (d, J=4.5 Hz, 1H), 5.51 (dd, J=10.5 Hz, 4.0 Hz, 1H), 5.32 (t, J=8.0 Hz, 1H), 5.06 (dd, J=10.0 Hz, 3.0 Hz, 1H), 4.70 (m, 1H), 4.62 (dd, J=20.0 Hz, 5.0 Hz, 1H), 4.45 (dd, J=20.0 Hz, 5.0 Hz, 1H), 3.10 (d, J=8.5 Hz, 2H). MW calculated for $C_{31}H_{27}N_7O_7$ (MH$^+$) 610, found 610 by LCMS.

Other 5'-substituted pyridine-ethers were transformed to various 2', 3'-acetals using methods similar to those given immediately above.

Example 3

Synthesis of 5'-isoxazole Derivatives

3-[6-(6-Chloro-purin-9-yl)-2,2-dimethyl-tetrahydro-furo[3,4-d][1,3]dioxol-ylmethoxy]-isoxazole-5-carboxylic acid methyl ester To a solution of [6-(6-Chloro-purin-9-yl)-2,2-dimethyl-tetrahydro-furo[3,4-d][1,3]dioxol-4-yl]-methanol (0.570 g, 1.74 mmol) in 16 mL of dry dichloromethane was added polymer-bound triphenylphosphine (PS-TPP; Argonaut Tech., 2.14 mmol/g, 0.91 g, 1.2 eq), followed by methyl-3-hydroxy-5-isoxazolecarboxylate (0.248 g, 1 eq). The mixture was sonicated for 15 minutes then stirred at room temperature for 1 h under argon. The reaction mixture was cooled to 0° C. and under argon flow diethylazodicarboxylate (0.33 g, 1.1 eq), dissolved in 1 ml of dichloromethane, was added dropwise via syringe. The mixture was protected from light and stirred at 0° C. for 30 min. then at room temperature for 20 h. The resin was washed liberally with dichloromethane and methanol. The organic solution obtained from the washes was concentrated to give, after flash chromatography purification, 0.740 g of the product as a white solid (95% yield). $^1$H NMR (300 MHz, CDCl$_3$) δ 8.76 (s, 1H), 8.23 (s, 1H), 6.42 (s, 1H), 6.23 (d, J=2.1 Hz, 1H), 5.43 (dd, J=2.1 Hz, 1H), 5.14 (dd, J=3.6 Hz, 1H), 4.7 (m, 1H), 4.61 (dd, J=3.9 Hz, 1H), 4.49 (dd, J=5.7 Hz, 1H), 3.93 (s, 3H), 1.65 (s, 3H), 1.42 (s, 3H). MW calculated for $C_{18}H_{18}ClN_5O_7$ (MH$^+$) 452, found 452 by LCMS.

3{-6-[6-(N-Benzyl-N-methyl-amino)-purin-9-yl]-2,2-dimethyl-tetrahydro-furo[3,4-d][1,3]dioxol-4-yl-methoxy}-isoxazole-5-carboxylic acid To a solution of 3-[6-(6-Chloro-purin-9-yl)-2,2-dimethyl-tetrahydro-furo[3,4-d][1,3]dioxol-4-ylmethoxy]-isoxazole-5-carboxylic acid methyl ester (0.106 g, 0.23 mmol) in tetrahydrofuran (1.2 mL) was added polymer-bound diisopropylethylamine (PS-DIEA; Argonaut Tech., 3.83 mmol/g, 0.190 g, 3 eq), followed by addition of 0.040 mL of N-methyl-N-benzylamine (1.2 eq). The resulting mixture was stirred at room temperature overnight. The PS-DIEA resin was washed three times with dichloromethane and the solution obtained from the washes was concentrated to yield 3-{6-[6-(N-Benzyl-N-methyl-amino)-purin-9-yl]-2,2-dimethyl-tetrahydro-furo[3,4-d][1,3]dioxol-4-ylmethoxy}-isoxazole-5-carboxylic acid methyl ester as yellow oil. This material (0.23 mmol) was dissolved in 1,4-dioxane (1.2 mL) and 0.250 mL of an aqueous 2M lithium hydroxide solution added. The mixture was stirred at room temperature for 4 h. The crude product, isolated after acid workup, was used without further purification in the following step. MW calculated for $C_{25}H_{26}N_6O_7$ (MH$^+$): 523, found 523 by LCMS.

3-{2-Benzyl-6-[6-(N-methyl-N-benzyl-amino)-purin-9-yl]-tetrahydro-furo[3,4-d][1,3]dioxol-4-yl-methoxy}-isoxazole-5-carboxylic acid A solution of the above acetonide (0.075 g, 0.140 mmol) dissolved in 1.5 mL of dry dichloromethane was cooled in an ice bath to 0° C. To this clear mixture was added 1.8 mL of trifluoroaceic acid. The mixture was stirred at 0° C. for 5 h to afford the intermediate diol as a yellow semisolid after evaporative workup. This crude product (0.23 mmol) was dissolved at 0° C. in 1 mL of dry trifluoroacetic acid in the flask. To this mixture was added a small amount of 3 A molecular sieves (previously dried by flame in situ and cooled by a stream of argon). The flask was capped with a rubber septum and cooled to 0° C., then 0.1 mL of phenyl acetaldehyde dimethyl acetal was added and the mixture stirred for 18 h at 0° C. At that point, 0.1 mL more of acetal was added and stirred an additional 6 h. Purification by HPLC yielded 52 mg of the desired product as a clear semisolid (62% yield). MW calculated for $C_{30}H_{28}N_6O_7$ (MH$^+$): 585, found 585 by LCMS.

The following acetonide-isoxazolecarboxylic acid analogs were prepared in a similar manner to the chloride displacement/hydrolysis sequence described above, using different amines:

Amine used; Product Data:
N-trans-(cyclopropylphenyl)amine; Calculated mass for product (LCMS): $C_{26}H_{26}N_6O_7$ (MH$^+$): 535, found: 535.
N-Methyl-N-Phenethylamine; Calculated mass for product (LCMS): $C_{26}H_{28}N_6O_7$ (MH$^+$): 537, found: 537.
Phenethylamine; Calculated mass for product (LCMS): $C_{25}H_{26}N_6O_7$ (MH$^+$): 523, found: 523.
Benzylamine; Calculated mass for product (LCMS): $C_{24}H_{24}N_6O_7$ (MH$^+$): 509, found: 509.
Isobutylamine; Calculated mass for product (LCMS): $C_{21}H_{26}N_6O_7$ (MH$^+$): 475, found: 475.
Cyclopentylamine; Calculated mass for product (LCMS): $C_{22}H_{26}N_6O_7$ (MH$^+$): 487, found: 487.
N-(Methylthiophene-yl)amine; Calculated mass for product (LCMS): $C_{22}H_{22}N_6O_7S$ (MH$^+$): 515 found: 515.
5-Methylfurfurylamnine; Calculated mass for product (LCMS): $C_{23}H_{24}N_6O_8$ (MH$^+$): 513, found: 513.
Propylamine; Calculated mass for product (LCMS): $C_{20}H_{24}N_6O_7$ (MH$^+$): 461, found: 461.
Aminopropylimidazole; Calculated mass for product (LCMS): $C_{23}H_{26}N_8O_7$ (MH$^+$): 527, found: 527.
3-Methylaminopyridine; Calculated mass for product (LCMS): $C_{23}H_{23}N_7O_7$ (MH$^+$): 510, found: 510.
Aminoethylpyrrolidine; Calculated mass for product (LCMS): $C_{23}H_{29}N_7O_7$ (MH$^+$): 516, found: 516.
Aniline; Calculated mass for product (LCMS): $C_{23}H_{22}N_6O_7$ (MH$^+$): 495, found: 495.

Example 4

Solution Phase Synthesis of 5'-Carboxamide Adenosine Analogs 2', 3'-O-Isopropylideneadenosine-5'-carboxylic Acid In a reaction vessel, bis-acetoxyiodobenzene (BAIB, 1.15 g, 3.58 mmol), 2,2,6,6-tetramethyl-1-piperidinyloxy (TEMPO, 0.051 g, 0.325 mmol), and 2', 3'-isopropylideneadenosine (0.500 g, 1.63 mmol) were combined, and 3 mL of 1:1 acetonitrile: water mixture was added to the reaction vessel. The reaction mixture was stirred at ambient temperature under argon for 1 h then filtered. The white crystalline product was washed with acetonitrile:water mixture (1:1) and dried in vacuo, to yield 0.464 g of product, 89%. $^1$H NMR (300 MHz, CD$_3$SOCD$_3$) δ 12.77 (br s, 1H), 8.22 (s, 1H), 8.06 (s, 1H), 7.27 (s, 2H), 6.32 (s, 1H), 5.52 (dd, J1=5.7 Hz, J2=1.8 Hz, 1H), 5.45 (d, J=9.5 Hz, 1 H), 4.67 (d, J=1.5 Hz, 1H), 1.52 (s, 3H), 1.35 (s, 3H).

2-({2,2-Dimethyl-6-[6(3-phenyl-ureido)-purin-9-yl]-tetrahydro-furo[3,4-d][1,3]dioxole-4-carbonyl}-amino)-benzoic acid methyl ester To a vial containing 2', 3'-O-Isopropylideneadenosine-5'-carboxylic acid (0.241 g, 0.75 mmol) was added 3-aminobenzoic acid methyl ester (0.144 g, 0.75 mmol) in one portion at RT followed by heating at 50° C. overnight. The reaction mixture was diluted with 100 ml of ethyl acetate, washed with 1N hydrochloric acid, saturated sodium bicarbonate, brine, and dried over MgSO$_4$. Upon removal of solvent, the solid residue was purified with chromatography with 2-5% methanol in dichloromethane to give 90 mg (26%) of the carboxamide as white solid. MW calculated for $C_{21}H_{22}N_6O_6$ (MH$^+$) 455, found 455 by LCMS. This carboxamide product (90 mg, 0.20 mmol) was dissolved in DMF (2 mL) and added to a flask containing phenyl isocyanate (35 mg, 0.30 mmol) in 2 ml of toluene at 50° C. The reaction was stirred at 50° C. overnight. Additional phenyl isocyanate (35 mg, 0.20 mmol) was then added in several portions until nearly complete consumption of the starting material was noted by TLC analysis. The reaction mixture was then diluted with ethyl acetate (100 ml), washed with saturated sodium bicarbonate, brine, and dried over magnesium sulfate. The crude product was purified by a chromatography with 0-2% methanol in dichloromethane to give 57 mg (50%) of pure product and recovered starting material (10 mg). $^1$H NMR (300 MHz, CDCl$_3$) δ 11.53 (s, 1H), 9.21 (s, 1H), 8.54 (s, 1H), 8.36 (s, 1H), 8.21 (s, 1H), 7.72 (m, 1H), 7.58 (m, 2H), 7.38 (m, 2H), 7.24 (m, 1H), 7.12 (m, 1H), 6.29 (d, J=2.1 Hz, 1H), 5.66 (dd, J=6.3, 1.5 Hz, 1H), 5.56

(dd, J=6.3, 1.5 Hz, 1H), 4.88 (d, J=1.8 Hz, 1H), 3.78 (s, 3H), 1.65 (s, 3H), 1.44 (s, 3H). MW calculated for $C_{28}H_{27}N_7O_7$ (MH$^+$): 574, found 574 by LCMS.

3-({2,2-Dimethyl-6-[6-(3-phenyl-ureido)-purin-9-yl]-tetrahydro-furo[3,4-d][1,3]dioxole-4-carbonyl}-amino)-benzoic acid To a vial containing 2', 3'-O-Isopropylideneadenosine-5'-carboxylic acid (250 mg, 0.778 mmol), triethylamine (1.57 mg, 1.56 mmol), and 3-amino-benzoic acid allyl ester (0.276 mg, 1.56 mmol) in 0.5 ml of N,N-dimethyl formamide at 0° C. was added PyBOP (0.443 mg, 0.856 mmol) in one portion. Reaction was continued at 0° C. for 4 h and at ambient for 4 h. Additional PyBOP (50 mg) was added and the reaction continued overnight at ambient temperature. The reaction mixture was diluted with ethyl acetate (100 ml), washed with saturated sodium bicarbonate, brine, and dried over magnesium sulfate. The crude was purified by a chromatography with 0-2% methanol in dichloromethane to give the desired amide product. MW calculated for $C_{23}H_{24}N_6O_6$ (MH$^+$) 481, found 481 by LCMS.

Phenyl isocyanate was coupled with the amide product using a method similar to those described above, affording the intermediate phenylurea compound. MW calculated for $C_{30}H_{29}N_7O_7$ (MH$^+$) 600, found 600 by LCMS.

This phenylurea compound (36 mg, 0.057 mmol) and morpholine (0.015 mg, 0.17 mmol) were dissolved in tetrahydrofuran (5 ml) followed by addition of tetrakis(triphenylphosphine)palladium (5 mg, 0.004 mmol). Reaction was completed in 4 h at RT. After removal of the solvent, the crude product mixture was purified by preparative HPLC to give the desired product. $^1$H NMR (300 MHz, CDCl$_3$) δ 11.52 (s, 1H), 9.99 (s, 1H), 9.60 (s, 1H), 8.61 (s, 1H), 8.42 (s, 1H), 7.94 (s, 1H), 7.72 (m, 4H), 7.34 (m, 2H), 7.23 (m, 1H), 7.06 (m, 1H), 6.56 (s, 1H), 5.56 (m, 2H), 4.88 (s, 1H), 1.58 (s, 3H), 1.39 (s, 3H).

Example 5

Solution Phase Synthesis of a Sulfonamide

N-{2,2-Dimethyl-6-[6-(3-phenyl-ureido)-purin-9-yl]-tetrahydro-furo[3,4-d][1,3]dioxole-4-carbonyl}-methanesulfonamide To a vial containing 2', 3'-O-Isopropylideneadenosine-5'-carboxylic acid (20 mg, 0.045 mmol), dimethylaminopyridine (5 mg, 0.045 mmol), and methanesulfonamide (0.009 mg, 0.091 mmol) in dichloromethane (0.5 ml) was added dicyclohexylcarbodiimide (10 mg, 0.05 mmol). The mixture was stirred for 2 days at RT. Additional dicyclohexylcarbodiimide (10 mg, 0.05 mmol) and dimethylaminopyridine (5 mg, 0.045 mmol) were added and the reaction was continued at RT overnight. To the reaction mixture was added ethyl acetate (75 ml), which was washed with 1 N hydrochloric acid, water, saturated sodium bicarbonate, brine, and dried over magnesium sulfate. Upon removal of solvent, the residue was purified by prep. HPLC to yield 13 mg of desired product (55%). MW calculated for $C_{21}H_{23}N_7O_7S$ (MH$^+$) 518, found 518 by LCMS.

Example 6

Solid Phase Synthesis of Ureas and Acetals from Polymer Bound 5'-Proline-Amides of Adenosine Commercially available hydroxymethylsulfanylmethyl (HESM) polystyrene resin (1.4 mmol/g, 200 mesh, NovaBiochem; 2.82 g, 3.95 mmol) was swelled for 15 minutes in 50 mL. In a separate reaction vessel, Boc-Pro-OH (3.40 g, 15.8 mmol), HATU (5.7 g, 15.0 mmol), dimethylaminopyridine (0.24 g, 1.98 mmol), and diisopropylethylamine (3.5 mL, 19.8 mmol) were dissolved in 40 mL of N,N-dimethyl formamide and stirred for 15 minutes. N,N-dimethyl formamide was drained from the HESM resin and the solution of activated proline derivative was added to the resin. The resin was agitated at RT for 17 h. The solvent was then drained and the resin washed with N,N-dimethyl formamide (3×30 mL), dichloromethane (3×30 mL), methanol (3×30 mL), dichloromethane (2×30 mL), methanol (3×30 mL) and dried in vacuo overnight. Mass of resin: 3.42 g, 93% loading.

Removal of BOC Protecting Group:

Resin obtained in the previous step was agitated with a 40% trifluoroacetic acid/dichloromethane solution (75 mL) for 15 minutes. The solvent was drained, and a fresh solution of 40% trifluoroacetic acid in dichloromethane was added, and resin was agitated for another 15 minutes. After this the resin was washed with dichloromethane (5×40 mL), 20% diisopropylethylamine/dichloromethane (2×30 mL), dichloromethane (3×30 mL), and methanol (5×40 mL). The resin was dried under vacuum. A chloranil test indicated the presence of a free amino group, and this proline-bound resin was carried over to the next step.

The proline resin product from the previous step was swelled in 50 mL N,N-dimethyl formamide for 30 minutes, after that the N,N-dimethyl formamide was drained. In a separate reaction vessel, 2', 3'-O-Isopropylideneadenosine-5'-carboxylic acid (1.40 g, 4.35 mmol), dichloroethane (0.91 g, 4.74 mmol), HOBtH$_2$O (0.73 g, 4.74 mmol), and diisopropylethylamine (3.5 mL, 19.8 mmol) were dissolved in 55 mL of N,N-dimethyl formamide. The solution was stirred for 15 minutes, and then added to the proline resin. The resin was agitated at RT for 17 h. The solvent was drained, the resin was washed with N,N-dimethyl formamide (3×30 mL), dichloromethane (3×30 mL), methanol (3×30 mL), dichloromethane (2×30 mL), methanol (3×30 mL), and dried in vacuo for 48 h. A chloranil test performed on a few sample beads indicated that coupling had occurred. A small amount of resin was cleaved using the following procedure to verify attachment of the carboxylic acid, and analysed by LCMS. Calculated mass for $C_{18}H_{22}N_6O_6$ (MH$^+$): 419, found 419 by LCMS. Mass of resin: 3.66 g, 0.55 mmol/g, 82% in three steps.

General Cleavage Procedure for Analysis of HESM Resin:

A small amount of resin is suspended in a solution of 5-6 equivalents of m-chloroperbenzoic acid in dichloromethane and agitated for 7-8 hours at RT. The solution is then drained, and the resin is washed 5-6 times with fresh dichloromethane. Then resin is suspended in a solution of 4-5 equivalents of DBU in dichloromethane, and agitated at RT for 4-5 hours. The resin is then filtered and the solution is analyzed by LC/MS, HPLC or another method. The compounds are recovered from solution by rotary evaporation.

The adenosine-proline amide-derivatized resin from the previous resin-synthesis step (0.5 g, 0.275 mmol) was suspended in anhydrous N,N-dimethyl formamide (10 mL). Ethyl isocyanate was added (0.43 mL, 5.5 mmol), and the reaction mixture was heated in a capped vial at 55° C. for 16 h. The resin was then drained and washed with N,N-dimethyl formamide (3×10 mL), dichloromethane (3×10 mL), methanol (3×10 mL), dichloromethane (2×10 mL), methanol (3×10 mL), and the procedure was repeated once again then the resin dried in vacuo for 24 h. A negative chloranil test indicated complete reaction. A small amount of this resin (bound to the 5'-adenosine-(2', 3'-acetonide)-proline amide-derivatized as the 6-ethylurea) was cleaved by the procedure described for cleavage of HESM resin, and the isolated product was analyzed by LCMS. Mass calculated for $C_{21}H_{27}N_7O_7$ (MH+): 490, found 490 by LCMS. Loading 0.52 mmol/g, mass 0.52 g, 98%.

The procedure described above was also used to prepare $N^6$-ureas with $R_d$=—$C_6H_{11}$, —Ph, —$CH_2Ph$, —$CH_2CH_2Ph$, -cyclopentyl, and trans-2-phenyl-cycloprop-1-yl groups using the appropriate isocyanates.

1-{6-[6-(3-Ethyl-ureido)-purin-9-yl]-2-phenyl-tetrahydro-furo[3,4-d][1,3]dioxole-4-carbonyl}-pyrrolidine-2-carboxylic acid The resin described above (0.05 g, 0.026 mmol) was suspended in trifluoroacetic acid, then benzaldehyde (0.095 g, 0.9 mmol) was added all at once. The resin was agitated in a tightly closed vial for 24 h. The resin was drained, washed with dichloromethane (5×3 mL), 20% diisopropylethylamine/dichloromethane (2×3 mL), dichloromethane (3×3 mL), and methanol (5×3 mL), then dried in vacuo for 3 h. The resin was cleaved using the cleavage procedure described above, the crude product was collected, analyzed by LCMS and purified by preparative HPLC. Calculated MW for $C_{25}H_{27}N_7O_7$ (MH+): 538, found: 538 by LCMS.

The following analogs were prepared in a similar manner to that described above, using appropriate combinations of isocyanates and aldehydes. Compounds analyzed by LCMS.

$R_d$=ethyl, $R_a$=benzyl Calculated MW for C26H29N7O7: 552.55 (MH+), found: 552.4.
$R_d$=ethyl, $R_a$=4-biphenyl Calculated MW for C31H31N7O7: 614.62 (MH+), found: 614.3
$R_d$=ethyl, $R_a$=3-biphenyl Calculated MW for C31H31N7O7: 614.62 (MH+), found: 614.3
$R_d$=ethyl, $R_a$=2-naphthyl Calculated MW for C29H29N7O7: 588.58 (MH+), found: 588.1.
$R_d$=n-hexyl, $R_a$=phenyl Calculated MW for C29H35N7O7: 594.63 (MH+), found: 594.3.
$R_d$=n-hexyl, $R_a$=benzyl Calculated MW for C30H37N7O7: 608.65 (MH+), found: 608.2.
$R_d$=n-hexyl, $R_a$=4-biphenyl Calculated MW for C35H39N7O7: 670.73 (MH+), found: 670.3.
$R_d$=n-hexyl, $R_a$=3-biphenyl Calculated MW for C35H39N7O7: 670.73 (MH+), found: 670.3.
$R_d$=n-hexyl, $R_a$=2-naphthyl Calculated MW for C33H37N7O7: 644.69 (MH+), found: 644.3.
$R_d$=cyclopentyl, $R_a$=benzyl Calculated MW for C29H33N7O7: 592.62 (MH+), found: 592.3.
$R_d$=cyclopentyl, $R_a$=phenyl Calculated MW for C28H31N7O7: 578.59 (MH+), found: 578.3.
$R_d$=cyclopentyl, $R_a$=4-biphenyl Calculated MW for C34H35N7O7: 654.68 (MH+), found: 654.3.
$R_d$=cyclopentyl, $R_a$=3-biphenyl Calculated MW for C34H35N7O7: 654.68 (MH+), found: 654.3.
$R_d$=cyclopentyl, $R_a$=2-naphthyl Calculated MW for C32H33N7O7: 628.65 (MH+), found: 628.4.
$R_d$=benzyl, $R_a$=benzyl Calculated MW for C31H31N7O7: 614.62 (MH+), found: 614.3.
$R_d$=benzyl, $R_a$=phenyl Calculated MW for C30H29N7O7: 600.59 (MH+), found: 600.3.
$R_d$=benzyl, $R_a$=2-naphthyl Calculated MW for C34H31N7O7: 650.65 (MH+), found: 650.3.
$R_d$=benzyl, $R_a$=4-biphenyl Calculated MW for C36H33N7O7: 676.69 (MH+), found: 676.3.
$R_d$=benzyl, $R_a$=3-biphenyl Calculated MW for C36H33N7O7: 676.69 (MH+), found: 676.3.
$R_d$=ethylphenyl, $R_a$=benzyl Calculated MW for C32H33N7O7: 628.65 (MH+), found: 628.4.
$R_d$=ethylphenyl, $R_a$=phenyl Calculated MW for C31H31N7O7: 614.62 (MH+), found: 614.5.
$R_d$=ethylphenyl, $R_a$=4-biphenyl Calculated MW for C37H35N7O7: 690.72 (MH+), found: 690.4.
$R_d$=ethylphenyl, $R_a$=3-biphenyl Calculated MW for C37H35N7O7: 690.72 (MH+), found: 690.5.
$R_d$=ethylphenyl, $R_a$=2-naphthyl Calculated MW for C35H33N7O7: 664.68 (MH+), found: 664.4.
$R_d$=cyclopropyl-trans-2-phenyl, $R_a$=benzyl Calculated MW for C33H33N7O7: 640.66 (MH+), found: 640.3.
$R_d$=cyclopropyl-trans-2-phenyl, $R_a$=3-biphenyl Calculated MW for C38H35N7O7: 702.73 (MH+), found: 702.6.
$R_d$=cyclopropyl-trans-2-phenyl, $R_a$=2-naphthyl Calculated MW for C36H33N7O7: 676.69 (MH+), found: 676.6.
$R_d$=phenyl, $R_a$=benzyl Calculated MW for C30H29N7O7: 600.59 (MH+), found: 600.3.
$R_d$=phenyl, $R_a$=phenyl Calculated MW for C29H27N7O7: 586.57 (MH+), found: 586.2.
$R_d$=phenyl, $R_a$=2-naphthyl Calculated MW for C33H29N7O7: 636.63 (MH+), found: 636.5.
$R_d$=phenyl, $R_a$=4-biphenyl Calculated MW for C35H31N7O7: 662.66 (MH+), found: 662.5.
$R_d$=phenyl, $R_a$=3-biphenyl Calculated MW for C35H31N7O7: 662.66 (MH+), found: 662.5.
$R_d$=phenyl, $R_a$=3-thianaphthene Calculated MW for C31H27N7O7S: 642.65 (MH+), found: 642.0.
$R_d$=ethylphenyl, $R_a$=3-thianaphthene Calculated MW for C33H31N7O7S: 670.71 (ME+), found: 670.0.
$R_d$=ethylphenyl, $R_a$=3-thianaphthene Calculated MW for C32H29N7O7S: 656.68 (MH+), found: 656.1.
$R_d$=n-hexyl, $R_a$=3-thianaphthene Calculated MW for C31H35N7O7S: 650.72 (MH+), found: 650.2.
$R_d$=n-hexyl, $R_a$=CHCHPh Calculated MW for C31H37N7O7: 620.67 (MH+), found: 620.4.
$R_d$=n-hexyl, $R_a$=CCPh Calculated MW for C31H35N7O7: 618.65 (MH+), found: 618.0.
$R_d$=cyclopropyl-trans-2-phenyl, $R_a$=CCPh Calculated MW for C34H31N7O7: 650.65 (MH+), found: 650.1.
$R_d$=ethylphenyl, $R_a$=CCPh Calculated MW for C33H31N7O7: 638.64 (MH+), found: 638.1.
$R_d$=benzyl, $R_a$=CCPh Calculated MW for C32H29N7O7: 624.62 (MH+), found: 624.1.
$R_d$=ethyl, $R_a$=CCPh Calculated MW for C27H27N7O7: 562.55 (MH+), found: 562.0.
$R_d$=cyclopropyl-trans-2-phenyl, $R_a$=4-biphenyl Calculated MW for C38H35N7O7: 702.73 (MH+), found: 702.1.
$R_d$=cyclopropyl-trans-2-phenyl, $R_a$=phenyl Calculated MW for C32H31N7O7: 626.63 (MH+), found: 626.0.
$R_d$=cyclopropyl-trans-2-phenyl, $R_a$=CHCHPh Calculated MW for C34H33N7O7: 652.67 (MH+), found: 652.1.
$R_d$=ethylphenyl, $R_a$=CHCHPh Calculated MW for C33H33N7O7: 640.66 (MH+), found: 640.3.

Example 7

(See Scheme 8) 1-[9-(2-Benzyl-6-ureidomethyl-tetrahydro-furo[3,4-d][1,3]dioxol-4-yl)-9H-purin-6-yl]-3-phenyl-urea methylsulfonamide In a reaction vessel were combined 2', 3'-O-benzylidene-$N^6$-(phenylurea)adenosine (0.200 g, 0.409 mmol), p-toluene sulfonyl chloride (0.148 g, 0.778 mmol), and 4.0 mL of pyridine. The mixture was stirred for 4 h at RT. The solvent was removed in vacuo and the tosylate (0.260 g, 99%) was recovered as a yellow solid. MW calculated for $C_{32}H_{30}N_6O_7S$: 643.19 ($MH^+$), found 642.9.

This tosylate product (0.260 g, 0.409 mmol) was dissolved in 3 mL of anhydrous N,N-dimethyl formamide, sodium azide (0.266 g, 4.09 mmol) was added, and the mixture was heated at 80° C. in a closed vial for 7 h while being stirred. The mixture was diluted with 50 mL of dichloromethane and extracted with 5% sodium bicarbonate solution and brine. The organic layer was separated, dried over anhydrous sodium sulfate and solvent was removed in vacuo. The azide derivative was recovered (0.183 g, 87%) as a white solid. MW calculated for $C_{25}H_{23}N_9O_4$: 514.19 ($MH^+$), found 514.1.

This residue containing the azide (0.180 g, 0.351 mmol) was dissolved in 6 mL of tetrahydrofuran/water mixture (18:1), polystyrene-bound triphenylphosphine was added (2.19 mmol/g, 0.800 g, 1.75 mmol), and the reaction mixture was stirred at RT under argon for 24 h. The reaction mixture was then filtered, the solvent was removed in vacuo and the crude product was chromatographed on a silica gel column (2 cm×15 cm). The column was eluted with dichloromethane/methanol/triethylamine (88:10:2) to give 0.072 g (42%) of the amine as a white solid. MW calculated for $C_{25}H_{25}N_7O_4$: 488.20 ($MH^+$), found 488.0.

A portion of the amine product above (0.022 g, 0.046 mmol) was dissolved in 2 mL of dichloromethane (anhydrous) and methylsulfonylethylcarbamate (0.008 g, 0.046 mmol) was added. The reaction was stirred at RT under argon for 72 h. Solvent was then removed in vacuo, and the crude product was purified by preparative HPLC (acetonitrile/0.1% trifluoroacetic acid//water/0.1% trifluoroacetic acid buffer). 0.016 g (59%) of product was recovered as a white solid. MW calculated for $C_{27}H_{28}N_8O_7S$: 609.18 ($MH^+$), found 609.4. $^1H$ NMR (300 MHz, $CD_3SOCD_3$) δ 11.69 (br s, 1H), 10.22 (br s, 1H), 8.69 (s, 1H), 8.65 (s, 1H), 7.60 (d, J=7.8 Hz, 2H), 7.36-7.21 (m, 6H), 7.07 (t, J=7.5 Hz, 1H), 6.90-6.87 (m, 1H), 6.57 (s, 1H), 6.22 (d, J=2.4 Hz, 1H), 5.75 (s, 1H), 5.45 (dd, J1=6.3 Hz, J2=2.1 Hz, 1H), 5.31 (t, J=5.1 Hz, 1H), 4.92 (dd, J1=6.6 Hz, J2=3.3 Hz, 1H), 4.16-4.02 (m, 5 H), 3.11 (s, 3H).

Example 8

5'-Homologated Derivatives as in Scheme 11

3-{2,2-Dimethyl-6-[6-(3-phenyl-ureido)-purin-9-yl]-tetrahydro-furo[3,4-d][1,3]dioxol-4-yl}-acrylic acid methyl ester To a vial containing the starting compound, 1-[9-(6-Hydroxymethyl-2,2-dimethyl-tetrahydro-furo[3,4-d][1,3]dioxol-4-yl)-9H-purin-6-yl]-3-phenyl-urea (1.07 g, 2.5 mmol), in 10 ml of dimethylsulfoxide was added IBX (1.06 g, 3.75 mmol) in one portion at RT. The white solid gradually dissolved as the reaction proceeded. After stirring at RT for 2 hours, methyl(triphenylphosphorylidene) acetate (0.84 g, 2.5 mmol) was added in one portion. The reaction was run at RT overnight. To the reaction mixture was added ethyl acetate (100 ml), which was washed with saturated $NaHCO_3$, brine, and dried over $MgSO_4$. After removal of solvent, the residue was recrystallized with isopropyl alcohol to provide the title compound. MW calculated for $C_{23}H_{24}N_6O_6$ ($MH^+$) 481.5 found 481.3 by LCMS.

3-{2,2-Dimethyl-6-[6-(3-phenyl-ureido)-purin-9-yl]-tetrahydro-furo[3,4-d][1,3]dioxol-4-yl}-propionic acid To a round bottom flask containing product from the previous step (1.2 g, 2.5 mmol) and palladium on carbon (10% w/w, 10 mg) under nitrogen was added methanol (20 ml). After flushing with hydrogen gas, the reaction mixture was stirred under a hydrogen atmosphere using a hydrogen balloon overnight at RT. Upon filtration and removal of solvent, the crude white solid product was recrystallized from isopropyl alcohol to give the desired methyl ester compound. MW calculated for $C_{23}H_{26}N_6O_6$ ($MH^+$) 483.5 found 483.2.

The methyl ester (500 mg, 1.04 mmol) was dissolved in 4 ml of methanol and sodium hydroxide (83 mg, 2.1 mmol) was then added. The reaction was stirred overnight at RT. After removal of methanol, acetic acid (2.1 mmol, 120 mmol) was added and a white solid precipitated. The solvent was removed under vacuum. The residue was recrystallized from water to provide the pure desired product as a white solid (0.4 g, 83%). MW calculated for $C_{22}H_{24}N_6O_6$ (M−1) 467.5 found 467.4 by LCMS.

1-(3-12,2-Dimethyl-6-[6(3-phenyl-ureido)-purin-9-yl]-tetrahydro-furo[3,4-d][1,3]dioxol-4yl}-propion-1-yl)-pyrrolidine-2-carboxylic acid To a vial containing the carboxylic acid product from the previous step (0.117 g, 0.25 mmol), thionyl chloride (0.3 g, 2.5 mmol) was added at 0° C. After addition, the cold bath was removed followed by addition of two drops of N,N-dimethyl formamide. The reaction mixture was heated to 50° C. for 30 minutes. The excess of thionyl chloride was removed under vacuum and the solid residue was washed with ethyl ether to give the acid chloride. The acid chloride (61 mg, 0.125 mmol) was added to a vial containing L-proline methyl ester (23 mg, 0.138 mmol) and triethylamine (28 mg, 0.275 mmol) in 1 mL of dichloromethane at 0° C. The reaction was gradually warmed to RT overnight. To the reaction mixture was added ethyl acetate (75 ml), which was washed with 1 N hydrochloric acid, saturated sodium bicarbonate, and dried over magnesium sulfate. The residue was purified by elution from a silica column using 2% methanol in dichloromethane to give purified prolylmethyl ester product (10 mg, 14%). MW calculated for $C_{28}H_{33}N_7O_7$ ($MH^+$) 580.6 found 580.3 by LCMS. The prolylmethyl ester (6 mg, 0.010 mmol) was dissolved in tetrahydrofuran (0.1 ml) followed by addition of 6 μl of 15% sodium hydroxide. After stirring at RT for 2 hrs, ethyl acetate (50 ml) was added and enough 1 N hydrochloric acid was added to adjust the pH to 3. The organic layer was washed with brine and dried over magnesium sulfate. After removal of solvent, the title compound was obtained as a white powder. MW calculated for $C_{27}H_{31}N_7O_7$ ($MH^+$) 566.6 found 566.3 by LCMS.

Example 9

Enzymatic Synthesis of a Mixture of 1-Ethyl-3-[9-(6-hydroxymethyl-2-styryl-tetrahydro-furo[3,4-d][1,3]dioxol-4-yl)-9H-purin-6-yl]-Urea Isomers from the Corresponding Isomeric Mixture of 5'-AMP Acetal/Urea Derivatives The 2', 3'-(cinnamylacetal)-$N^6$-(ethylurea) derivative of AMP (0.750 g, 0.14 mmol) as a mixture of acetal diastereoisomers was dissolved in water (25 mL, 1.4 mol) in a round bottom flask and the pH was adjusted to 8.3 with NaOH. The temperature was adjusted to 35 C, and alkaline phosphatase (0.003 g, 0.00004 mol) was added. Within 15 minutes, the mixture became rather heterogenous, and methanol (20 mL, 0.5 mol) was added to resolubilize the nucleoside product. After 4 h the reaction was judged essentially complete by HPLC. The reaction was worked up by adding more MeOH (20 mL), heating to 60 C to denature the enzyme, and filtering through a 0.22 uM filter. The methanol was evaporated in vacuo, and a white, fine-particle solid precipitated from the remaining solvent. This mixture was cooled in an ice bath and filtered. Washing the material with water, followed by drying over $P_2O_5$ in a dessicator afforded the title product as a mixture of acetal diastereomers. Dry weight 440 mg (0.10 mmol, 71% yield).

Example 10

3-}6-[6-(3-Ethyl-ureido)-purin-9-yl]-2-styryl-tetrahydro-furo[3,4-d][1,3]dioxol-4-yl}-acrylic acid methyl ester 1-Ethyl-3-[9-(6-hydroxymethyl-2-styryl-tetrahydro-furo[3,4-d][1,3]dioxol-4-yl)-9H-purin-6-yl]-urea (5.0 g, 11 mmol) was suspended in dry acetonitrile (50 mL) and Dess-Martin periodinate (6.7 g, 16 mmol) was added. The suspension was stirred 2 h, after which time proton NMR of an aliquot showed complete conversion to the aldehyde. (Methoxycarbonylmethylene)triphenylphosphorane (3.9 g, 12 mmol) was added and stirring was continued overnight. The reaction mixture was then diluted with ethyl acetate (300 mL), washed with saturated sodium bicarbonate/thiosulfate solution (100 mL), dried with sodium sulfate and filtered. The filtrate was evaporated and the solid was dissolved in hot isopropyl alcohol (50 mL). It was allowed to cool, then heptane was added and it was stirred overnight. The resulting precipitate was washed with heptane and dried under vacuum, affording the desired product (2.9 g, 71%). $^1$H-NMR (300 MHz, d$_6$DMSO) δ1.15 (t, 3H, J=7 Hz), 3.21 (q, 2H, J=7 Hz), 3.59 (s, 3H), 4.98 (m, 1H), 5.28 (ψt, 1H, J=6 Hz), 5.51 (dd, 1H, J=6 Hz, <2 Hz), 5.70 (d, 1H, J=16 Hz), 5.90 (d, 1H, J=6 Hz), 6.30 (dd, 1H, J=6 Hz, 16 Hz), 6.45 (d, 1H, J<2 Hz), 6.95 (d, 1H, J=15 Hz), 7.35 (m, 3H), 7.45 (d, 2H, J=7 Hz), 8.50 (s, 1H), 8.60 (s, 1H), 9.30 (t, 1H, J=6 Hz), 9.60 (s, 1H).

Example 11

3-{6-[6(3-Ethyl-ureido)-purin-9-yl]-2-styryl-tetrahydro-furo[3,4-d][1,3]dioxol-4-yl}-propionic acid methyl ester 3-{6-[6-(3-Ethyl-ureido)-purin-9-yl]-2-styryl-tetrahydro-furo[3,4-d][1,3]dioxol-4-yl}-acrylic acid methyl ester (250 mg, 0.5 mmol) was dissolved in dry methanol (3 mL). Copper (II) sulfate (90 mg, 0.5 mmol) was added followed by sodium tetrahydroborate (90 mg, 2.5 mmol) and the reaction was stirred 48 h. The reaction was diluted with water, filtered, and concentrated in vacuo. The residue was dissolved in ethyl acetate and precipitated with heptane. The precipitate was dissolved in dichloromethane and was chromatographed on silica gel with dichloromethane-methanol (95:5) as eluent, affording the title compound (125 mg, 50%). $^1$H-NMR (300 MHz, d$_6$DMSO) δ1.15 (t, 3H, J=7 Hz), 1.90 (m, 2H), 2.19 (m, 2H), 3.21 (q, 2H, J=7 Hz), 3.55 (s, 3H), 4.20 (m, 1H), 4.98 (dd, 1H, J=4 Hz, 6 Hz), 5.45 (dd, 1H, J=3 Hz, 7 Hz), 5.85 (d, 1H, J=6 Hz), 6.25 (d, 1H, J=3 Hz), 6.27 (dd, 1H, J=6 Hz, 16 Hz), 6.90 (d, 1H, J16 Hz), 7.35 (m, 3H), 7.50 (d, 2H, J=7 Hz), 8.56 (s, 1H), 8.57 (s, 1H), 9.30 (t, 1H, J=5 Hz), 9.60 (s, 1H).

Example 12

3-{6-[6-(3-Ethyl-ureido)-purin-9-yl]-2-styryl-tetrahydro-furo[3,4-d][1,3]dioxol-4-yl}-propionic acid 3-{6-[6-(3-Ethyl-ureido)-purin-9-yl]-2-styryl-tetrahydro-furo[3,4-d][1,3]dioxol-4-yl}-propionic acid methyl ester (5.0 g, 10 mmol) was dissolved in tetrahydrofuran (300 mL). Water (100 mL) was added, followed by lithium hydroxide (1.0 g, 25 mmol). The solution was allowed to stir 16 h at room temperature. It was acidified to pH 5 with acetic acid, concentrated in vacuo, then extracted with chloroform (300 mL). The organic extract was evaporated, redissolved in ethyl acetate and precipitated with heptane to afford the final product (3.9 g, 80%). $^1$H-NMR (300 MHz, d$_6$DMSO) δ1.14 (t 3H, J=7 Hz), 1.90 (m, 2H), 2.19 (m, 2H), 3.26 (q, 2H, J=6 Hz), 4.17 (m, 1H), 4.93 (ψt, 1H, J=6 Hz), 5.43 (dd, 1H, J=3 Hz, 7 Hz), 5.84 (d 1H, J=6 Hz), 6.24 (d, 1H, J=3 Hz), 6.28 (dd, 1H, J=7 Hz, 13 Hz), 6.90 (d, 1H, J16 Hz), 7.35 (m, 3H), 7.51 (d, 2H, J=7 Hz), 8.56 (s, 1H), 8.61 (s, 1H), 9.30 (t, 1H, J=6 Hz).

Example 13

Effects of 6-(phenylureido)purine2', 3'-(4-ethylcyclohexylspiroketyl)-5'-nicotinyl-ribofuranoside (Compound A) and {6-[6(Cyclohexylmethyl-amino)-purin-9-yl]-2-isobutyl-tetrahydro-furo[3,4-d][1,3]dioxol-4-yl}-methanol (Compound B) on the Abdominal Constriction Assay for Visceral Pain in Mice This example demonstrates the effects of the above-mentioned two compounds in a model of acetic acid-induced abdominal constriction in mice, a model of visceral pain. The method employed is a modification of the abdominal constriction test described by Collier, et. al (Collier, et al., *Br. J. Pharmacol. Chemother.* 32: 295-310 (1968)). For the rest of the example, compound: 6-(phenylureido)purine-2', 3'-(4-ethylcyclohexylspiroketyl)-5'-nicotinyl-ribofuranoside is named "Compound A" and {6-[6-(Cyclohexylmethyl-amino)-purin-9-yl]-2-isobutyl-tetrahydro-furo[3,4-d][1,3]dioxol-4-yl}-methanol is named "Compound B".

Control Group Pain Response

Briefly, a group of eight mice is designated as the control group, and each of said mice in the group receives an intraperitoneal (i.p.) injection of physiological saline in a dose-volume: mouse-weight ratio of 5 mL/kg ten minutes prior to an i.p. injection of 0.9% acetic acid in physiological saline in a dose-volume: mouse-weight ratio of 10 mL/kg. Each of said mice in the control group is placed in its own observation chamber shortly after the acetic acid injection and is allowed to explore. Each testing period starts 5 minutes after the acetic acid injection into a mouse, and consists of 10 minutes of observation during which time the number of abdominal constrictions of the mouse are counted. Abdominal constriction is defined as a lengthwise stretching of the torso with concave arching of the back. An average number of total constrictions per mouse per observation time is calculated from mice in the control group, and this indicates a baseline level of pain response in the control group animals.

Inhibition of Pain Response by Compound A

Compound A is administered i.p., at a dose of 50 mg/kg suspended in a volume of physiological saline (5 mL/kg), 10 minutes prior to the administration of acetic acid, as described for the control group above. Eight animals are used in this group and observation of said group demonstrates a statistical difference between the number of averaged abdominal constrictions in the saline control group versus the Compound A group, where the number of averaged abdominal constrictions during the observation time interval is lower when Compound A is introduced, compared to saline control.

Inhibition of Pain Response by Compound B

Compound B is administered i.p., at a dose of 50 mg/kg suspended in a volume of physiological saline (5 mL/kg), 10 minutes prior to the administration of acetic acid, as described for the control group above. Eight animals are used in this group and observation of said group demonstrates a statistical difference between the number of averaged abdominal constrictions in the saline control group versus the Compound B group, where the number of averaged abdominal constrictions during the observation time interval is lower when Compound B is introduced, compared to saline control.

In similar studies, Compound A and Compound B demonstrate a dose dependent pharmacological effect over saline vehicle control in reducing the abdominal constrictions induced by 0.9% acetic acid. This example demonstrates that compounds of Formula I are effective in treating, preventing or reducing the incidence of visceral pain in animals.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of treating pain comprising administering to a subject in need thereof an effective amount of a compound of Formula III, a tautomer, or a pharmaceutically-acceptable salt, hydrate, or solvate thereof:

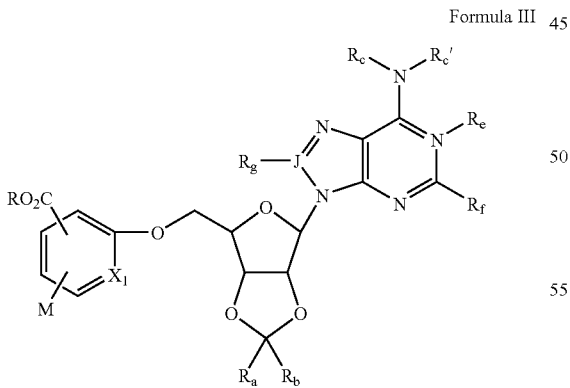

Formula III wherein $R_a$ and $R_b$ are each independently selected from the group consisting of: hydrogen, saturated or unsaturated $C_{1-8}$ alkyl, saturated or unsaturated $C_{3-7}$ cycloalkyl, aralkyl, aryl, and saturated or unsaturated $C_{2-6}$ heterocycle; or $R_a$ and $R_b$ are optionally taken together to form a ring of 3 to 7 members, with or without substitution, and with or without heteroatoms in place of ring carbon atoms;

$R_c$ and $R_c'$ are independently selected from the group consisting of: H, OR, saturated or unsaturated $C_{1-8}$ alkyl, saturated or unsaturated $C_{3-7}$ cycloalkyl, aralkyl, aryl, saturated or unsaturated heterocycle, and $-C(G)\Sigma$; wherein G=O, S or $NR_d$; and $\Sigma=L, R_d, OR_d$, or $N(R_d)_2$; except that $-NR_cR_c'$ cannot be $-N(OR)_2$; and $OR_d$ cannot be $-OH$;

each $R_d$ is independently selected from the group consisting of: H, saturated or unsaturated $C_{1-8}$ alkyl, saturated or unsaturated $C_{3-7}$ cycloalkyl, aralkyl, aryl, heteroaryl, and saturated or unsaturated $C_{2-6}$ heterocycle; or two $R_d$ groups are optionally taken together to form a ring of 4 to 7 members, with or without unsaturation and with or without heteroatoms in place of ring-carbon units; or one $R_d$ and one of $R_c$ or $R_c'$ are optionally taken together to form a ring of 4 to 7 members, with or without unsaturation and with or without heteroatoms in place of ring-carbon units;

R is selected from the group consisting of: H, saturated or unsaturated $C_{1-8}$ alkyl, saturated or unsaturated $C_{3-7}$ cycloalkyl, aryl, aralkyl, heteroaryl, and saturated or unsaturated $C_{2-6}$ heterocycle;

L is selected from the group consisting of: H, $-CF_3$, $-CF_2CF_3$, saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, saturated or unsaturated $C_{1-6}$ alkoxy, aralkoxy, aryloxy, N,N-disubstituted-amino, N-substituted amino, and unsubstituted-amino;

when L is N-substituted-amino, or N,N-disubstituted-amino, each substituent of said amino group of L is selected from the group consisting of: $C_{1-8}$ alkyl, $C_{3-7}$ cycloalkyl, aryl, aralkyl, heteroaryl, and saturated or unsaturated $C_{2-6}$ heterocycle;

when L is N,N-disubstituted-amino, the two substituents independently selected from the group above are optionally taken together to form a ring of 3 to 7 members, wherein said formed ring thereon bears the remaining features of said selected substituents before said ring formation;

$R_e$=O or absent;

$R_f$=H, halogen, saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, $-OH$, saturated or unsaturated $C_{1-6}$ alkoxy, aryloxy, $-SH$, $C_{1-6}$ thioalkyl, thioaryl, $-[(CO)OR]$, $-[(CO)NRR]$, amino, $-N$-substituted amino, or N,N-disubstituted amino; wherein each said substituent on said N-substituted-amino-group, or N,N-disubstituted-amino-group of $R_f$ is independently selected from the group consisting of: $C_{1-8}$ alkyl, $C_{3-7}$ cycloalkyl, aryl, aralkyl, heteroaryl, $C_{2-6}$ heterocycle, $-[(CO)R]$ and $-[(CO)-NRR]$; wherein each R is independently as defined above; or when $R_f$ is $-[(CO)NRR]$, $-[NH(CO)NRR]$, $-[N(C_{1-8}$ alkyl)(CO)NRR]$, $-[N(aryl)(CO)NRR]$, or $[N(aralkyl)(CO)NRR]$, the R groups of a said $-NRR$ unit in $R_f$ are optionally taken together such that a ring of 3 to 7 members is formed, with or without heteroatoms in place of the ring-carbon units;

J=N or C, with the proviso that when J=N, then $R_g$ is absent;

when J=C, $R_g$ is selected from the group consisting of: $-H$, halogen, saturated or unsaturated $C_{1-8}$ alkyl, saturated or unsaturated $C_{3-7}$ cycloalkyl, aralkyl, aryl, $-OH$, saturated or unsaturated $C_{1-6}$ alkoxy, aryloxy, —SH, $C_{1-6}$ thioalkyl, thioaryl, —[(CO)OR], —[(CO)NRR], and —NRR; wherein each R is independently as defined above; or when $R_g$ is —[(CO)NRR] or —NRR, the R groups of said —NRR unit in $R_g$ can be taken together such that a ring of 3 to 7 members is formed, with or without heteroatoms in place of the ring-carbon units;

$X_1$ is N, and

M is independently selected from the group consisting of: —H, halogen, $CF_3$, saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, —OH, $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, —[(CO)R], —[(CO)O—($C_{1-8}$ alkyl)], and —[(CO)—NRR]; and when M is —[(CO)NRR], —[NH(CO)NRR], —[N($C_{1-8}$ alkyl)(CO)NRR], —[N(aryl)(CO)NRR], or —[N(aralkyl)(CO)NRR], the R groups of any said -NRR unit in M are optionally taken together such that a ring of 3 to 7 members is formed, with or without heteroatoms in place of the ring-carbon units.

2. The method according to claim 1 wherein said compound is selected from the group consisting of: 6-{2,2-Dimethyl-6-[6-(3-phenyl-ureido)-purin-9-yl]-tetrahydro-furo [3,4-d][1,3]dioxol-4-ylmethoxy}-5-fluoro-nicotinic acid; 5-Chloro-6-{2,2-dimethyl-6-[6-( 3-phenyl-ureido)-purin-9-yl]-tetrahydro-furo [3,4-d][1,3]dioxol-4-ylmethoxy}-nicotinic acid; 2-{2,2-Dimethyl-6-[6-(3-phenyl-ureido)-purin-9-yl]-tetrahydro-furo [3,4-d][1,3]dioxol-4-ylmethoxy}-nicotinic acid; 6-Chloro-2-{2,2-dimethyl-6-[6-(3-phenyl-ureido)-purin-9-yl]-tetrahydro-furo [3,4-d][1,3]dioxol-4-ylmethoxy}-5-fluoro-nicotinic acid; 6-Chloro-2-(2,2-dimethyl-6-[6-(3-phenyl-ureido)-purin-9-yl]-tetrahydro-furo [3,4-d][1,3]dioxol-4-ylmethoxy}-5-flouro-nicotinic acid; 2-[6-[6-(3 Phenyl-ureido)-purin-9-yl]2-2-(2-trifluoromethyl-phenyl)-tetrahydro-furo [3,4-d][1,3]dioxol-4-ylmethoxy]-nicotinic acid; 2-{2-Phenyl-6-[6-(3-phenyl-ureido)-purin-9-yl]-tetrahydro-furo [3,4-d][1,3]dioxol-4-ylmethoxy}-nicotinic acid; 2-(2-Biphenyl-3-yl-6-[6-(3-phenyl-ureido)-purin-9-yl]-tetrahydro-furo [3,4-d][1,3]dioxol-4-ylmethoxy}-nicotinic acid; 2-{2-Naphthalen-2-yl-6-[6-(3-phenyl-ureido)-purin-9-yl]-tetrahydro-furo [3,4-d][1,3]dioxol-4-ylmethoxy}-nicotinic acid; 2-{2-Benzo[b]thiophen-3-yl-6-[6-(3-phenyl-ureido)-purin-9-yl]-tetrahydro-furo [3,4-d][1,3]dioxol-4-ylmethoxy}-nicotinic acid; 2-{6-[6-(3-Hexyl-ureido)-purin-9-yl]-2-phenyl-tetrahydro-furo [3,4-d][1,3]dioxol-4-ylmethoxy}-nicotinic acid; 2-{2,2-Dimethyl-6-[6-(3-phenyl-ureido)-purin-9-yl]-tetrahydro-furo [3,4-d][1,3]dioxo-spiroindan-4-ylmethoxy}-nicotinic acid; 2-(6-[6-(3-Ethyl-ureido)-purin-9-yl]-2-phenethyl-tetrahydro-furo [3,4-d][1,3]dioxol-4-ylmethoxy}-nicotinic acid; 2-{6-[6-(3-Ethyl-ureido)-purin-9-yl]-2-phenylethynyl-tetrahydro-furo [3,4-d][1,3]dioxol-4-ylmethoxy}-nicotinic acid; 2- (6-[6-(3-Ethyl-ureido)-purin-9-yl]-2-phenyl-tetrahydro-furo[3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo [3,4-d][1,3]dioxol-4-ylmethoxy}-nicotinic acid; 2-{6-[6-(3-Cyclopentyl-ureido)-purin-9-yl]-2-phenethyl-tetrahydro-furo [3,4-cl][1,3]dioxol-4-ylmethoxy}-nicotinic acid; 2-(6-[6-(3-Cyclopentyl-ureido)-purin-9-yl]-2, 2-(3,4-Dihydro-1 H-naphthalen)-tetrahydro-furo [3,4-yl][1,3]dioxol-4-ylmethoxy}-nicotinic acid; 2-{6-[6-(3-Cyclopentyl-ureido)-purin-9-yl]-2-p-tolyl-tetrahydro-furo [3,4-yl][1,3]dioxol-4-ylmethoxy}-nicotinic acid; 2-{2-Biphenyl-4-yl-6-[6-(3-hexyl-ureido)-purin-9-yl]-tetrahydro-furo [3,4-yl][1,3]dioxol-4-ylmethoxy}-nicotinic acid; 2-{2-(4-Acetylamino-phenyl)-6-[6-(3-cyclopentyl-ureido)-purin-9-yl]-tetrahydro-furo [3,4-yl][1,3]dioxol-4-ylmethoxy}-nicotinic acid; and 2-{2-tert-Butyl-6-[6-(3-phenyl-ureido)-purin-9-yl]-tetrahydro-furo [3,4-yl][1,3]dioxol-4-ylmethoxy}-nicotinic acid.

3. A method of treating pain comprising administering to a subject in need thereof a pharmaceutical composition comprising an effective amount of a compound of Formula IV, a tautomer, or a pharmaceutically acceptable salt, hydrate, or solvate thereof,

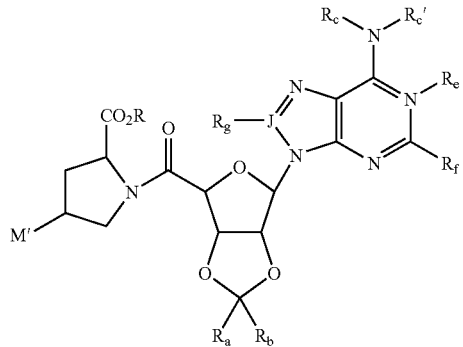

Formula IV wherein $R_a$, $R_b$, $R_c$, $R_c'$, $\Sigma$, R, L, $R_d$, $R_e$, $R_f$, J, $R_g$ are as defined in Formula I of claim 1;

M' is selected from the group consisting of: —H, halogen, $CF_3$, saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, —OH, $C_{1-6}$ alkoxy, aralkoxy, aryloxy, —SH, $C_{1-6}$ thioalkyl, thioaryl, —[(CO)OR], —[(CO)NRR], amino, —N-substituted amino, and N,N-disubstituted amino; wherein each said substituent on said amino of M is independently selected from the group consisting of: saturated or unsaturated $C_{1-8}$ alkyl, saturated or unsaturated $C_{3-7}$ cycloalkyl, aryl, aralkyl, heteroaryl, saturated or unsaturated $C_{2-6}$ heterocycle, —[(CO)R], —[(CO)O—($C_{1-8}$ alkyl)], and —[(CO)—NRR]; and when M' is —[(CO)NRR], —[NH(CO)NRR], —[N($C_{1-8}$ alkyl)(CO)NRR], —[N(aryl)(CO)NRR], or—[N(aralkyl)(CO)NRR], the R groups of any said —NRR unit in M' are optionally taken together such that a ring of 3 to 7 members is formed, with or without heteroatoms in place of the ring-carbon units;

the M' and —$CO_2R$ groups are independently attached to any carbon of the pyrrolidine ring; and M' is not a halogen, hydroxy, sulfhydryl, or amino group when M' is attached to a carbon that is bonded to the pyrollidine nitrogen atom at the alpha position.

4. The method according to claim 3, wherein said compound is selected from the group consisting of: 1-{2-Phenyl-6-[6-(3-phenyl-ureido)-purin-9-yl]-tetrahydro-furo [3,4-d][1,3]dioxole-4-carbonyl}-pyrrolidine-2-carboxylic acid; 1-{2-Phenyl-6-[6-(3-phenyl-ureido)-purin-9-yl]-tetrahydro-furo [3,4-d][1,3]dioxole-4-carbonyl}-pyrrolidine-2-carboxylic acid; 1-{2-Benzyl-6-[6-(3-ethyl-ureido)-purin-9-yl]-tetrahydro-furo [3,4-d][1,3]dioxole-4-carbonyl}- pyrrolidine-2-carboxylic acid; 1-(2-Phenyl-6-{6-[3-(2-phenyl-cyclopropyl)-ureido]-purin-9-yl}-tetrahydro-furo [3,4-d][1,3]dioxole-4-carbonyl)-pyrrolidine-2-carboxylic acid; 1-{6-[6-(3-Benzyl-ureido)-purin-9-yl]-2-phenyl-tetrahydro-furo [3,4-d][1,3]dioxole-4-carbonyl}-pyrrolidine-2-carboxylic acid; 1-{2-Benzo [b]thiophen-3-yl-6-[6-(3-hexyl-ureido)-purin-9-yl]-tetrahydro-furo [3,4-d][1,3]dioxole-4-carbonyl}-pyrrolidine-2-carboxylic acid; 1-{2-Benzyl-6-[6-(3-hexyl-ureido)-purin-9-yl]-tetrahydro-furo [3,4-d][1,3]dioxole-4-carbonyl}-pyrrolidine-2-carboxylic acid; 1-{6-[6-(3-Ethyl-ureido)-purin-9-yl]-2-naphthalen-2-yl-tetrahydro-furo [3,4-d][1,3]dioxole-4-carbonyl}-pyrrolidine-2-carboxylic acid; 1-{6-[6-(3-Hexyl-ureido)-purin-9-yl]-2-phenyl-tetrahydro-furo [3,4-d][1,3]dioxole-4-carbonyl}-pyrrolidine-2-carboxylic acid; 1-{6-[6-(3-Cyclopentyl-ureido)-purin-9-yl]-2-phenyl-tetrahydro-furo [3,4-d][1,3]dioxole-4-carbonyl}-pyrrolidine-2-carboxylic acid; and 1-(3-{2,2-Dimethyl-6-[6-(3-phenyl-ureido)-purin-9-yl]-tetrahydro-furo [3,4-d][1,3]dioxol-4-yl}-propionyl)-pyrrolidine-2-carboxylic acid.

5. The method according to claim 1, wherein said pain is traumatic pain, neuropathic pain, organ pain, or pain associated with diseases.

6. The method according to claim 3, wherein said traumatic pain is pain resulting from injury, burn, post-surgical pain or inflammatory pain.

7. The method according to claim 5, wherein said organ pain is ocular, corneal, bone, heart, skin, visceral, joint, dental or muscle pain.

8. The method according to claim 5, wherein said diseases are cancer, AIDS, arthritis, herpes, sickle cell anemia or migraine.

9. The method according to claim 1, wherein said pharmaceutical composition is administered topically to said subject.

10. The method according to claim 1, wherein said pharmaceutical composition is administered via injection to said subject.

11. The method according to claim 1, wherein said pharmaceutical composition is administered orally to said subject.

12. The method according to claim 1, wherein said pharmaceutical composition is administered by intranasal administration to said subject.

13. The method according to claim 1, wherein said pharmaceutical composition is administered to said subject in an inhaleable form.

14. The method according to claim 2, wherein said compound is included in a pharmaceutical composition.

15. The method according to claim 2, wherein said compound is selected from the group consisting of: 2-[6-[6-(3-Phenyl-ureido)-purin-9-yl]-2-(2-trifluoromethyl-phenyl)-tetrahydro-furo [3,4-d][1,3]dioxol-4-ylmethoxy]-nicotinic acid; 2-{2-Phenyl-6-[6-(3-phenyl-ureido)-purin-9-yl]-tetrahydro-furo [3,4-d][1,3]dioxol-4-ylmethoxy}-nicotinic acid; 2-{2-Biphenyl-3-yl-6-[6-(3-phenyl-ureido)-purin-9-yl]-tetrahydro-furo [3,4-d][1,3]dioxol-4-ylmethoxy}-nicotinic acid; 2-{2-Naphthalen-2-yl-6-[6-(3-phenyl-ureido)-purin-9-yl]-tetrahydro-furo [3,4-d][1,3]dioxol-4-ylmethoxy}-nicotinic acid; 2-{2-Benzo [b]thiophen-3-yl-6-[6-(3-phenyl-ureido)-purin-9-yl]-tetrahydro-furo [3,4-d][1,3]dioxo 1-4-ylmethoxy}-nicotinic acid; 2-{6-[6-(3-Hexyl-ureido)-purin-9-yl]-2-phenyl-tetrahydro-furo [3,4-d][1,3]dioxol-4-ylmethoxy}-nicotinic acid; 2-{2,2-Dimethyl-6-[6-(3-phenyl-ureido)-purin-9-yl]-tetrahydro-furo [3,4-d][1,3]dioxo-spiroindan-4-ylmethoxy}-nicotinic acid; 2-{6-[6-(3-Ethyl-ureido)-purin-9-yl]-2-phenethyl-tetrahydro-furo [3,4-d][1,3]dioxol-4-ylmethoxy}-nicotinic acid; 2-{6-[6-(3-Ethyl-ureido)-purin-9-yl]-2-phenylethynyl-tetrahydro-furo [3,4-d][1,3]dioxol-4-ylmethoxy}-nicotinic acid; 2-(6-[6-(3-Ethyl-ureido)-purin-9-yl]-2-phenyl-tetrahydro-furo [3,4-d][1,3]dioxol-4-ylmethoxy}-nicotinic acid; 2-{2-(2-Bromo-phenyl)-6-[6-(3-ethyl-ureido)-purin-9-yl]-tetrahydro-furo [3,4-d][1,3]dioxol-4-ylmethoxy}-nicotinic acid; 2-{6-[6-(3-Cyclopentyl-ureido)-purin-9-yl]-2-phenethyl-tetrahydro-furo [3,4-d][1,3]dioxol-4-ylmethoxy}-nicotinic acid; 2-{6-[6-(3-Cyclopentyl-ureido)-purin-9-yl]-2,2-(3,4-Dihydro-1H-naphthalen)-tetrahydro-furo [3,4-d][1,3]dioxol-4-ylmethoxy}-nicotinic acid; 2-{6-[6-(3-Cyclopentyl-ureido)-purin-9-yl]-2-p-tolyl-tetrahydro-furo [3,4-d][1,3]dioxol-4-ylmethoxy}-nicotinic acid; 2-{2-Biphenyl-4-yl-6-[6-(3-hexyl-ureido)-purin-9-yl]-tetrahydro-furo [3,4-d][1,3]dioxol-4-ylmethoxy}-nicotinic acid; 2-{2-(4-Acetylamino-phenyl)-6-[6-(3-cyclopentyl-ureido)-purin-9-yl]-tetrahydro-furo [3,4-d][1,3]dioxol-4-ylmethoxy}-nicotinic acid; and 2-{2-tert-Butyl-6-[6-(3-phenyl-ureido)-purin-9-yl]-tetrahydro-furo [3,4-d][1,3]dioxol-4-ylmethoxy}-nicotinic acid.

16. The method according to claim 2, wherein said compound is 2-{2-Biphenyl-4-yl-6-[6-(3-hexyl-ureido)-purin-9-yl]-tetrahydro-furo [3,4-d][1,3]dioxol-4-ylmethoxy}-nicotinic acid.

17. The method according to claim 1, wherein $R_c$ and $R_c'$ are independently selected from the group consisting of: H, OR, saturated or unsaturated $C_{1-8}$ alkyl, saturated or unsaturated $C_{3-7}$ cycloalkyl, aralkyl, aryl, and saturated or unsaturated heterocycle.

18. The method according to claim 17, wherein $R_a$ and $R_b$ are independently selected from the group consisting of: hydrogen, saturated or unsaturated $C_{1-8}$ alkyl, saturated or unsaturated $C_{3-7}$ cycloalkyl, aralkyl, aryl, and saturated or unsaturated $C_{2-6}$ heterocycle.

19. The method according to claim 3, wherein $R_c$ and $R_c'$ are independently selected from the group consisting of: H, OR, saturated or unsaturated $C_{1-8}$ alkyl, saturated or unsaturated $C_{3-7}$ cycloalkyl, aralkyl, aryl, and saturated or unsaturated heterocycle.

20. The method according to claim 19, wherein $R_a$ and $R_b$ are independently selected from the group consisting of: hydrogen, saturated or unsaturated $C_{1-8}$ alkyl, saturated or unsaturated $C_{3-7}$ cycloalkyl, aralkyl, aryl, and unsaturated $C_{2-6}$ heterocycle.

* * * * *